(12) United States Patent
Shultzaberger et al.

(10) Patent No.: US 12,352,745 B2
(45) Date of Patent: Jul. 8, 2025

(54) CIRCULATING RNA SIGNATURES SPECIFIC TO PREECLAMPSIA

(71) Applicant: Illumina, Inc., San Diego, CA (US)

(72) Inventors: Sarah E. Shultzaberger, San Diego, CA (US); Fiona Kaper, San Diego, CA (US); Sarah Kinnings, San Diego, CA (US); Suzanne Rohrback, San Diego, CA (US); Carlo Randise-Hinchliff, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/620,245

(22) PCT Filed: May 24, 2019

(86) PCT No.: PCT/US2019/033964
§ 371 (c)(1),
(2) Date: Dec. 6, 2019

(87) PCT Pub. No.: WO2019/227015
PCT Pub. Date: Nov. 28, 2019

(65) Prior Publication Data
US 2021/0148899 A1 May 20, 2021

Related U.S. Application Data

(60) Provisional application No. 62/848,219, filed on May 15, 2019, provisional application No. 62/676,436, filed on May 25, 2018.

(51) Int. Cl.
*G01N 33/53* (2006.01)
(52) U.S. Cl.
CPC ... *G01N 33/5308* (2013.01); *G01N 2800/368* (2013.01); *G01N 2800/50* (2013.01)
(58) Field of Classification Search
CPC .................................................. G01N 33/53
See application file for complete search history.

(56) References Cited

U.S. PATENT DOCUMENTS

| | | | |
|---|---|---|---|
| 9,657,342 B2 | 5/2017 | Rava et al. | |
| 10,240,199 B2 | 3/2019 | Lo et al. | |
| 2010/0273671 A1 | 10/2010 | Lauwerys et al. | |
| 2011/0171650 A1 | 7/2011 | Conrad et al. | |
| 2012/0270739 A1 | 10/2012 | Rava et al. | |
| 2014/0087967 A1 | 3/2014 | Goren et al. | |
| 2014/0243212 A1 | 8/2014 | Lo et al. | |
| 2016/0289762 A1* | 10/2016 | Koh | C12Q 1/6883 |
| 2017/0234874 A1* | 8/2017 | Adams | G01N 21/553 435/7.21 |
| 2023/0392207 A1 | 12/2023 | Shultzaberger et al. | |

FOREIGN PATENT DOCUMENTS

| | | |
|---|---|---|
| JP | 2006/515517 | 6/2006 |
| JP | 2008/524993 | 7/2008 |
| WO | 2004/065629 A1 | 8/2004 |
| WO | 065629 | 9/2004 |
| WO | 2006/097051 A1 | 9/2006 |
| WO | 097051 | 9/2006 |
| WO | 2014/132244 A1 | 9/2014 |
| WO | 132244 | 9/2014 |
| WO | 2016062893 A1 | 4/2016 |
| WO | 2019227015 A1 | 11/2019 |
| WO | 2021102236 A1 | 5/2021 |

OTHER PUBLICATIONS

Hansen et al., The Genetic Component of Preeclampsia: A Whole-Exome Sequencing Study, PLoS One, 2018, 1-16. (Year: 2018).*
Hansen et al., S1 Appendix, Supplementary Methods, the Genetic Component of Preeclampsia: A Whole-Exome Sequencing Study, PLoS One, 2018, 1-36. (Year: 2018).*
Textoris et al., Evaluation of Current and New Biomarkers in Severe Preeclampsia: A Microarray Approach Reveals the VSIG4 Gene as a Potential Blood Biomarker, PLoS One, 2013, 8(12), 1-8. (Year: 2013).*
Diaz et al., Performance of Streck cfDNA Blood Collection Tubes for Liquid Biopsy Testing, PLoS One, 2016, 11(11), 1-18. (Year: 2016).*
Hansen et al., PLoS One, the Genetic Component of Preeclampsia: A Whole-Exome Sequencing Study, May 2018, 1-16. (Year: 2018).*
Hansen et al., PLoS One, S1 Appendix, the Genetic Component of Preeclampsia: A Whole-Exome Sequencing Study, May 2018, 1-36. (Year: 2018).*
Textoris et al., Evaluation of Current and New Biomarkers in Severe Preeclampsia: A Microarray Approach Reveals the VSIG4 Gene as a Potential Blood Marker, PLoS One, 2013, 1-8. (Year: 2013).*
Diaz et al., Performance of Streck cfDNA Blood Collection Tubes for Liquid Biopsy Testing, PLoS One, 2016, 1-18. (Year: 2016).*
Lee et al., Clinical Exome Sequencing for Genetic Identification of Rare Mendelian Disorders, JAMA, 2014, 312(18), 1880-1887. (Year: 2014).*
Kaartokallio et al., Exome Sequencing in Pooled DNA Samples to Identify Maternal Preeclampsia Risk Variants, Scientific Reports, 2016, 6, 1-9. (Year: 2016).*
Kaartokallio et al., Supplemental Information, Exome Sequencing in Pooled DNA Samples to Identify Maternal Preeclampsia Risk Variants, Scientific Reports, 2016, 6, 1-4. (Year: 2016).*
UCLA Health System, UCLA Molecular Diagnostics Laboratories, Clinical Exome Sequencing V3, 2015, 1-98. (Year: 2015).*

(Continued)

*Primary Examiner* — Amy M Bunker
(74) *Attorney, Agent, or Firm* — Mueting Raasch Group

(57) ABSTRACT

The present invention includes methods and materials for use in the detection preeclampsia and/or determining an increased risk for preeclampsia in a pregnant female, the method including identifying in a biosample obtained from the pregnant women a plurality of circulating RNA (C-RNA) molecules.

12 Claims, 31 Drawing Sheets

(56) References Cited

OTHER PUBLICATIONS

UCLA Health, Common Tests During Pregnancy, UCLA Health, 2000-2003, 1-6; obtained online at https://www.uclahealth.org/departments/pathology/outreach/services/molecular-diagnostics-laboratories pathology outreach on Feb. 11, 2023. (Year: 2000).*
Rouillard et al., Hypertension Gene Set, Harmonizome, 2016, 1-2; obtained at: https://maayanlab.cloud/Harmonizome/gene_set/Hypertension/CTD+Gene-Disease+Associations harmonize on Feb. 11, 2023. (Year: 2016).*
Rouillard et al., Supplemental Gene Set, Hypertension Gene Set, Harmonizome, 2016, 1-2; obtained at: https://maayanlab.cloud/Harmonizome/gene_set/Hypertension/CTD+Gene-Disease+Associations harmonize on Feb. 11, 2023. (Year: 2016).*
SinoBiological, SKIL Research Reagents, SinoBiological, 2024, 1-7. Obtained online at: https://www.sinobiological.com/category/skil SKIL Research Reagents | SinoBiological on Aug. 19, 2024. (Year: 2024).*
ThermoFisher, Plasma and Serum Prepation, ThermoFisher Scientific, 2007, 1-2. Obtained at: https://www.thermofisher.com/us/en/home/references/protocols/cell-and-tissue-analysis/elisa-protocol/elisa-sample-preparation-protocols/plasma-and-serum-preparation.html#:~:text=Plasma%20is%20produced%20when%20.*
GenBank, *Homo sapiens* a disintegrin-like and metalloprotease (reprolysin type) with thrombospondin type 1 motif, 2 (ADAMTS2), mRNA, NCBI Reference Sequence: NM_014244.1, Apr. 26, 2000, 3 pages.
Textoris et al., "Evaluation of Current and New Biomarkers in Severe Preeclampsia: A Microarray Approach Reveals the VSIG4 Gene as a Potential Blood Biomarker", PLOS ONE, Dec. 2013, vol. 8, e82638.
Japanese Office Action for Application No. 2019-566953 dated May 9, 2022, with English translation, 6 pages.
"Preeclampsia-Symptoms and Causes" Mayo Clinic [On-Line]. https://www.mayoclinic.org/diseases-conditions/preeclampsia/symptoms-causes/syc-20355745?p=1. 5 pgs.
"Reviewing Maternal Deaths is First Step in Preventing Them," Mar. 6, 2018 [On Line]: https://www.preeclampsia.org/the=news/138-latest-news/677-reviewing-maternal-deaths-is-first-step-in-preventing-them?tmpl=component&print=1&page=] Obtained—May 17, 2018: 1 pg.
"TruSeq® DNA Sample Preparation Guide" Illumina Proprietary, Part # 15026486 Rev. C, Jul. 2012; 148 pgs.
"TruSeq® RNA Sample Preparation v2 Guide," Illumina Proprietary, RS-122-9001DOC, Part # 15026495 Rev. F, Mar. 2014; 132 pgs.
"TruSeqTM Exome Enrichment Guide" Illumina Proprietary, Catalog # FC-930-1012, Part # 15013230 Rev B, Nov. 2010; 56 pgs.
Chen et al., "Personal Omics Profiling Reveals Dynamic Molecular and Medical Phenotypes," Cell, Mar. 16, 2012; 148:1293-1307.
Chen et al., "Whole-Exome Enrichment with the Agilent SureSelect Human All Exon Platform," Cold Spring Harb Protoc, Mar. 11, 2015: 626-633.
Chen et al., "Whole-Exome Enrichment with the Illumina TruSeq Exome Enrichment Platform," Cold Spring Harb Protoc, Mar. 11, 2015: 642-648.
Chen et al., "Whole-Exome Enrichment with the Roche NimbleGen SeqCap EZ Exome Library SR Platform," Cold Spring Harb Protoc, 2015(7): 11 pgs.
Chim et al., "Detection and Characterization of Placental MicroRNAs in Maternal Plasma," Clin Chem, 2008;54(3):482-490.
Conover et al., "Pregnancy-Associated Plasma Protein-A2 (PAPP-A2): Tissue Expression and biological Consequences of Gene Knockout in Mice," Endocrinology, Jul. 2011;152(7):2837-2844.
Crosley et al., "First-Trimester Levels of Pregnancy-Associated Plasma Protein A2 (PAPP-A2) in the Maternal Circulation are Elevated in Pregnancies that Subsequently Develop Preeclampsia," Reproductive Sciences, 2014;21(6):754-760.
Diaz et al., "Performance of Streck cfDNA Blood Collection Tubes for Liquid Biopsy Testing," PLOS One, Nov. 10, 2016; 18 pgs.
Farina et al., :Quantitative distribution of a panel of circulating mRNA in preeclampsia versus controls, Prenatal Diagnosis, 2006;26:1115-1120.
Go et al., "Detection of Placental Transcription Factor mRNA in Maternal Plasma," Clinical Chemistry, 2004;50(8):1413-1414.
Huang et al., "Characterization of Human plasma-derived exosomal RNAs by deep sequencing," BMC Genomics, 2013;14:319:14 pgs.
International Search Report and Written Opinion for PCT/US2019/033964, issued by the European Patent Office on Aug. 28, 2019; 16 pgs.
International Search Report and Written Opinion for PCT/US2020/061466, issued by the European Patent Office on Feb. 23, 2021; 13 pgs.
Karumanchi et al., "Preeclampsia and Pregnancy-Related Hypertensive Disorders," Hypertension, 2016;67:238-242.
Kishikawa et al., "Circulating RNAs as new biomarkers for detecting pancreatic cancer," World J Gastroenterol, Jul. 2015;28(21):8527-8540.
Koh et al., "Noninvasive in vivo monitoring of tissue-specific global gene expression in humans," PNAS, May 20, 2014;111(20):7361-7366.
Koh et al., Corrections for "Noninvasive in vivo monitoring of tissue-specific global gene expression in humans," PNAS, Jul. 29, 2014;111(30):11223.
Li et al., "Role of exosomal proteins in cancer diagnosis," Molecular Cancer, 2017;16;145: 12 pgs.
Lun et al., "Noninvasive prenatal Methylomic Analysis by Genomewide Bisulfite Sequencing of maternal Plasma DNA," ClinChem, 2013;59(11):1583-1594.
Maron et al., "Gene expression analysis in pregnant women and their infants identifies unique fetal biomarkers that circulate in maternal blood," JClinRes, Oct. 2007;117(10):3007-3019.
McCarthy and Smyth, "Testing significance relative to a fold-change threshold is a Treat," Bioinformatics, 2009;25(6):765-771.
Muchel et al., "Circulating transcripts in maternal blood reflect a molecular signature of early-onset preeclampsia," SciTranslMed, Jul. 1, 2020;12(eaaz0131):12 pgs.
Ng et al., "The Concentration of Circulating Corticotropin-releasing Hormone mRNA in Maternal Plasma Is Increased in Preeclampsia," ClinicalChemistry, 2003;49(5):727-731.
Ng et al., mRNA of placental origin is readily detectable in maternal plasma, PNAS, Apr. 15, 2003;100(8):4748-4753.
Ngo et al., "Noninvasive blood tests for fetal development predict gestational age and preterm delivery," Science, Jun. 8, 2018; 360:1133-1136.
Poon et al., "Presence of Fetal RNA in Maternal Plasma," ClinChem, 2000;46(11):1832-1834.
Purwosunu et al., "Cell-Free mRNA Concentrations of Plasminogen Activator Inhibitor-I and tissue-Type Plasminogen Activator Are Increased in the Plasma of Pregnant Women with Preeclampsia," ClinicalChemistry, 2007;53:3:399-404.
Qin et al., "A novel blood collection device stabilizes cell-free RNA in blood during sample shipping and storage," BMC Research Notes, 2013:6;380:8 pgs.
Qin et al., "High-Throughput sequencing of human plasma RNA by using thermostable group II intron reverse transcriptases," RNA, 22:111-128.
Quinn et al., "Reprogramming of the Transcriptome in a Novel Chromosome 3 Transfer Tumor Suppressor Ovarian Cancer Cell Line Model Affected Molecular Networks That Are Characteristic of Ovarian Cancer," MolCarcinogenesis, 2009;48:648-661.
Robinson et al., "edgeR: a Bioconductor package for differential expression analysis of digital gene expression data," Bioinformatics, 2010;26(1):139-140.
Rolnik et al., "Aspirin versus Placebo in Pregnancies at High Risk for Preterm Preeclampsia," NewEnglJMed, Aug. 17, 2017;377(7):613-622.
Sato-Kuwabara et al., "The fusion of two worlds: Non-coding RNAs and extracellular vesicles-diagnostic and therapeutic implications (Review)" Intl J of Oncology, 2015;46:17-27.

(56) References Cited

OTHER PUBLICATIONS

Smets et al., "Novel Biomarkers in preeclampsia," ClinicaChimicaActa, 2006;364:22-32.
Steinbrecher et al., "Pregnancy-Associated Plasma Protein-A2 and Anthropometry, Lifestyle, and Biochemical Factors in a Human Adult Population," SciRepts, 2005;7:10455.
Townsend et al., "Current best practice in the management of hypertensive disorders in pregnancy," IntBloodPressControl, 2016;9:79-94.
Tsang et al., "Integrative single-cell and cell-free plasma RNA transcriptomics elucidates placental cellular dynamics," PNAS, Aug. 22, 2017; E7786-E7795.
Tsui et al., "Maternal Plasma RNA Sequencing for Genome-Wide Transcriptomic Profiling and Identification of Pregnancy-Associated Transcripts," ClinChem, 2014; 60(7):954-962.
Tsui et al., "Systematic micro-array based identification of placental mRNA in maternal plasma: towards non-invasive prenatal gene expression profiling," J Med Genet, 2004;41:461-467.
U.S. Appl. No. 62/578,360, filed Oct. 27, 2017, Quake et al., "A Noninvasive Molecular Clock for Fetal Development Predicts Gestational Age and Preterm Delivery-II".
Umu et al., "A comprehensive profile of circulating RNAs in human serum," RNABiology, 2018;15(2):242-250.
Wagner et al., "Regulation of pregnancy-associated plasma protein A2 (PAPPA2) in a human placental trophoblast cell line (BeWo)," RepBioEndo, 2011;9(4):7 pgs.
Yoffe et al., "Early Detection of Preeclampsia Using Circulating Small non-coding RNA," Scientific Reports, 2018;8:3401: 11 pgs.
Gormley et al., "Preeclampsia: novel insights from global RNA profiling of trophoblast subpopulations," Aug. 2017, Am J Obstet Gynecol, 217(2):17 pages.
Hui et al., "Cell-free fetal nucleic acids in amniotic fluid," Oct. 5, 2010, Human Reproduction Update, 17(3):362-71.
Paquette et al, "Comparative analysis of gene expression in maternal peripheral blood and monocytes during spontaneous preterm labor," Mar. 2018, Am J Obstet Gynecol, 218(3): page count here.
Cao, et al., "Decreased Levels of UBE2Q1 and CHIP in the placentas of infection related preterm birth", Clin. Exp. Obstet. Gynecol., XLV, No. 5, 2018.
Cheung, et al., "Natural variation in human gene expression assessed in lymphoblastoid cells", Nature Genetics, vol. 33, Mar. 2003.
UBE2Q1 tissue expression data from NCBI, 2 pages printed from the world wide web at ncbi.nlm.nih.gov/gene/55585/?report_expression on May 24, 2022.
UCLA Health System (UCLA Molecular Diagnostics Laboratories, 2012, 1-36, 119 and 509.
"GeneChip Human Genome, U133 Plus 2.0 Array", Applied Biosystems Products Information Sheet, pp. 1-2, Nov. 17, 2017.
Wikipedia definition of Exome Sequencing retrieved from https://en.wikipedia.org/w/index.php?title+Exome_sequencing&oldid+1079651064 on Mar. 27, 2022, 10 pages.

Hu et al., "Competing endogenous RNA expression profiling in pre-eclampsia identifies hsa_circ_0036877 as a potential novel blood biomarker for early pre-eclampsia," Clinical Epigenetics, 2018, vol. 10, No. 48, pp. 1-12.
Purwosuno et al., "Cell-free mRNA concentrations of CRH, PLAC1, and selectin-P are increased in the plasma of pregant women with preeclampsia," Prenatal Diagnosis, 2007, vol. 27, No. 8, pp. 772-777.
Purwosuno et al., "Prediction of preeclampsia by analysis of cell-free messenger RNA in maternal plasma," American Journal of Obstetrics and Gynecology, 2009, vol. 200, No. 4, pp. 386.e1-386.e7.
Banzola et al., Performance of a panel of maternal serum markers in predicting preeclampsia at 11-15 weeks' gestation, Prenatal Diagnosis, 2007, vol. 27, pp. 1005-1010.
Hosikawa et al., "Hypoxia induces different genes in the lungs of rats compared with mice", 2003, Physiol. Genomics, 12:209-219.
PALM2AKAP2 PALM2 and AKAP2 fusion [*Homo sapiens* (human)], National Library of Medicine, Updated Jan. 25, 2024, Retrieved from the Internet <URL: from https://www.ncbi.nlm.nih.gov>, 2 pages.
Sitras et al., "Differential placental gene expression in severe preeclampsia," Placenta, May 2009, vol. 30, No. 5, pp. 424-433.
Knight et al., "Characterization of gene expression changes over healthy term pregnancies," Oct. 10, 2018, *PLoS One*, 13(10), 12 pages.
Mayo Clinic, "Preeclampsia Diagnosis & Treatment," from mayoclinic.org, © 1998-2024, [online]. Retrieved from the Internet: <URL: https://www.mayoclinic.org/diseases-conditions/preeclampsia/diagnosis-treatment/drc-20355751>, 11 pages, [retrieved on Sep. 12, 2024].
NICHD, "What are the treatments for preeclampsia, eclampsia, & HELLP syndrome?" from www.nichd.nih.gov, Office of Communications last reviewed Nov. 19, 2018, [online]. Retrieved from the Internet: <URL: https://www.nichd.nih.gov/health/topics/preeclampsia/conditioninfo/treatments>; 4 pages, [retrieved on Sep. 12, 2024].
"Preterm birth" World Health Organization Definition from WHO website, dated May 10, 2023, [online]. Retrieved from the Internet: <URL: https://www.who.int/news-room/fact-sheets/detail/preterm-birth>; 4 pages, [retrieved on Sep. 12, 2024].
Quinn et al, "Preterm birth: Case definition & guidelines for data collection, analysis, and presentation of immunization safety data," 2016, *Vaccine*, 34:6047-56.
United States Patent & Trademark Office's Example 29 "Subject Matter Eligibility Examples: Life Sciences," May 2016, 9 pages.
United States Patent & Trademark Office's Memorandum, "Recent Subject Matter Eligibility Decision: *Vanda Pharmaceuticals Inc.* v. *West-Ward Pharmaceuticals*," Jun. 7, 2018, 3 pages.
Buckberry S., "An Integrative Analysis of the Human Placental Transcriptome", The University of Adelaide, Doctoral Thesis, Jul. 2015, pp. 142-174.

\* cited by examiner

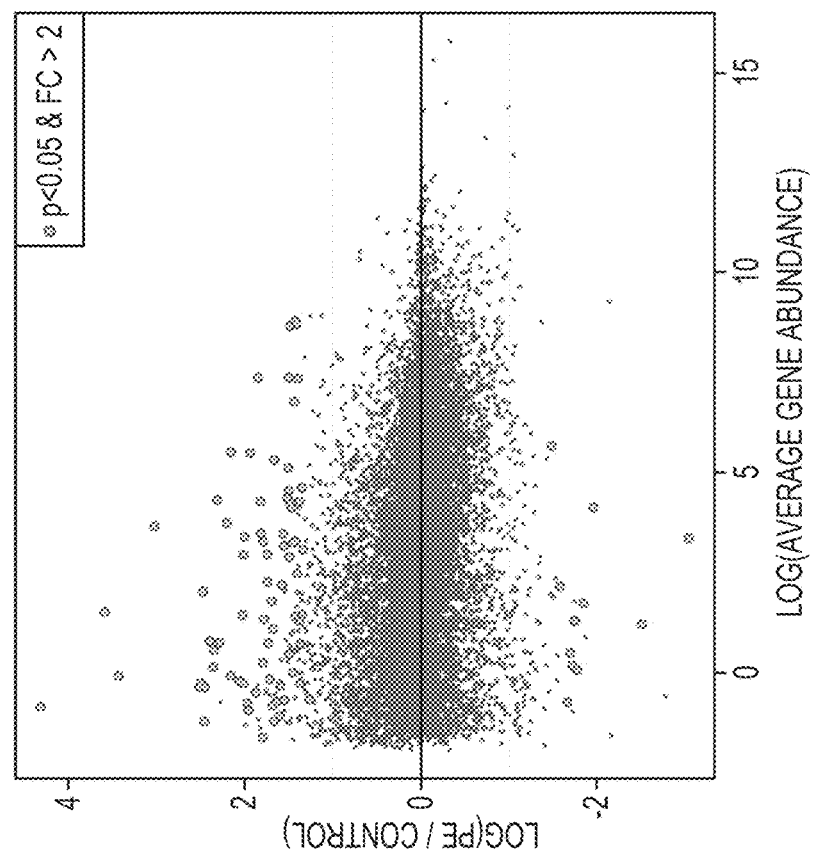
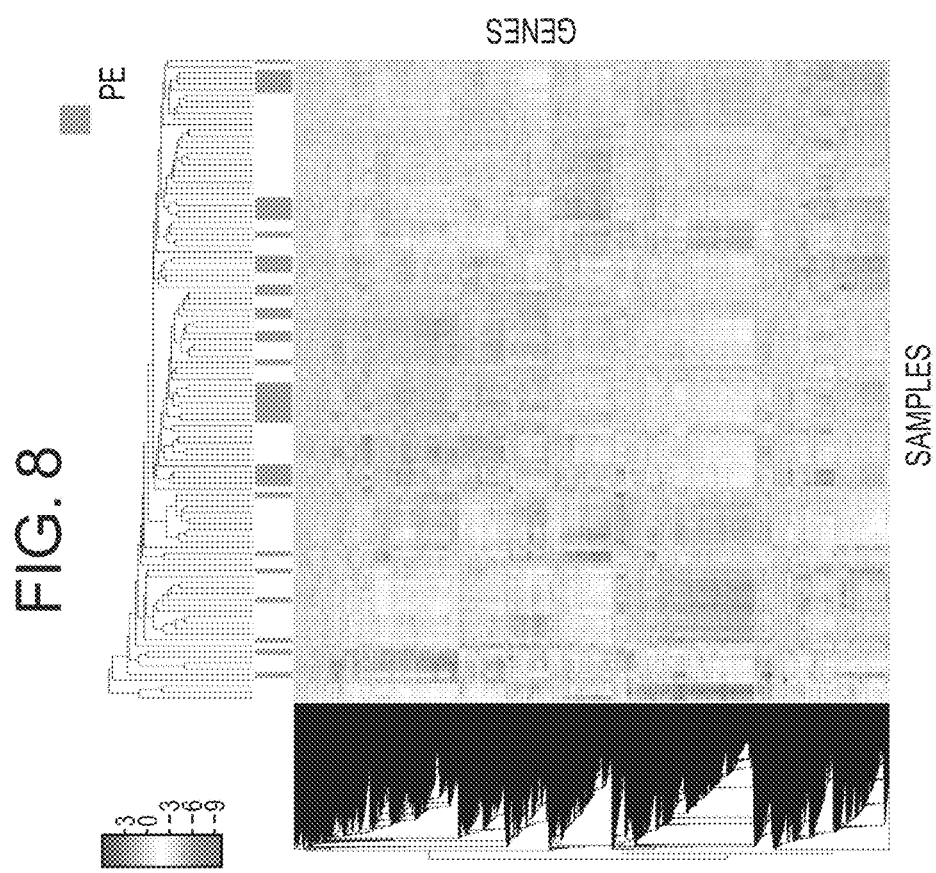
FIG. 8

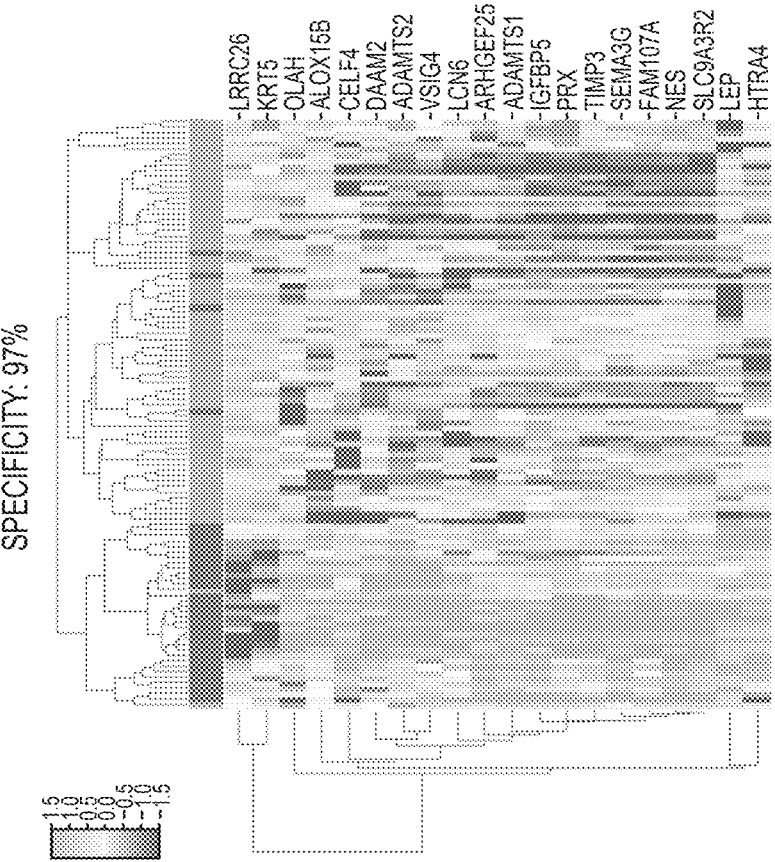
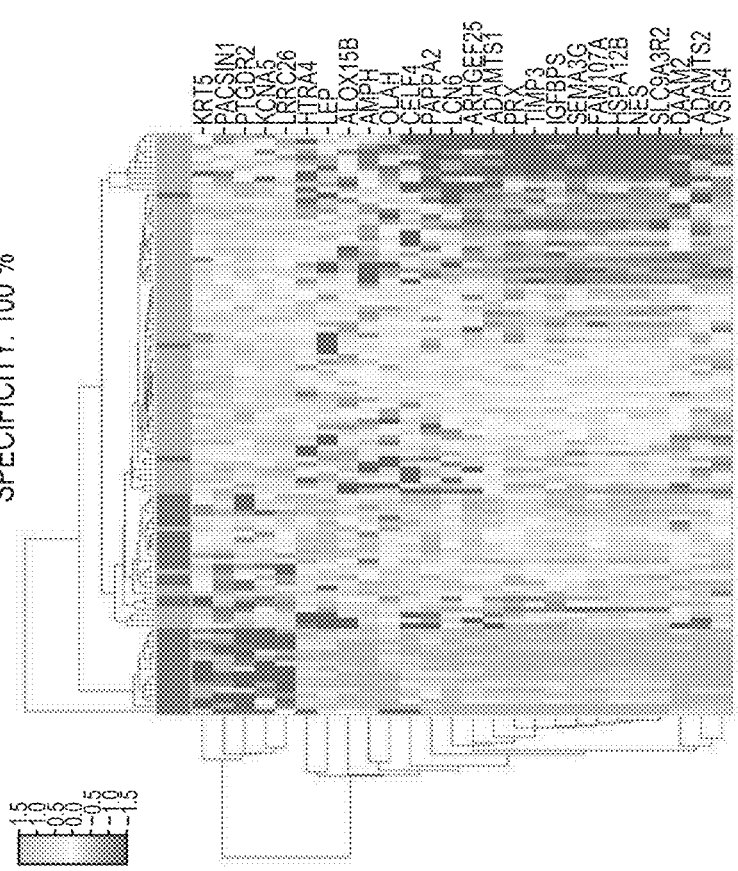
FIG. 20

Gestational Age (weeks)

FIG. 23A
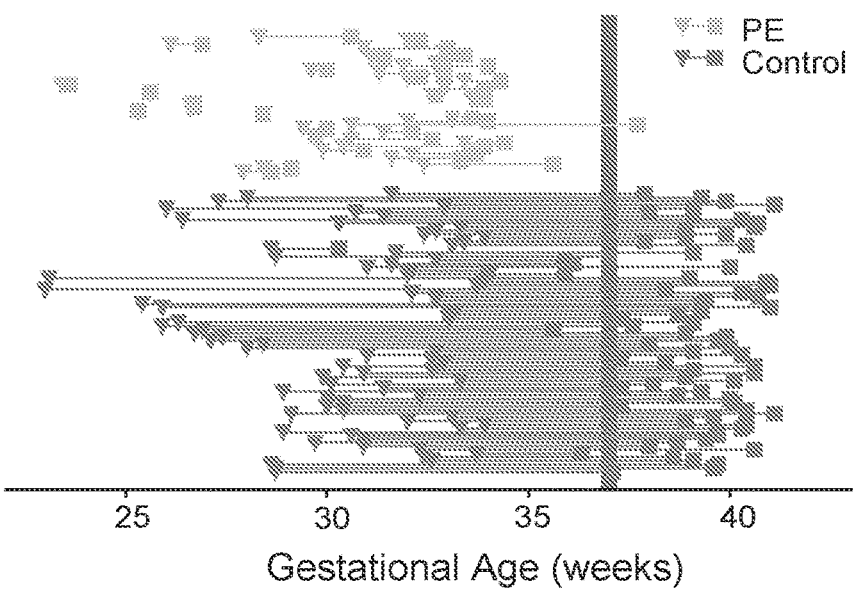
FIG. 23B
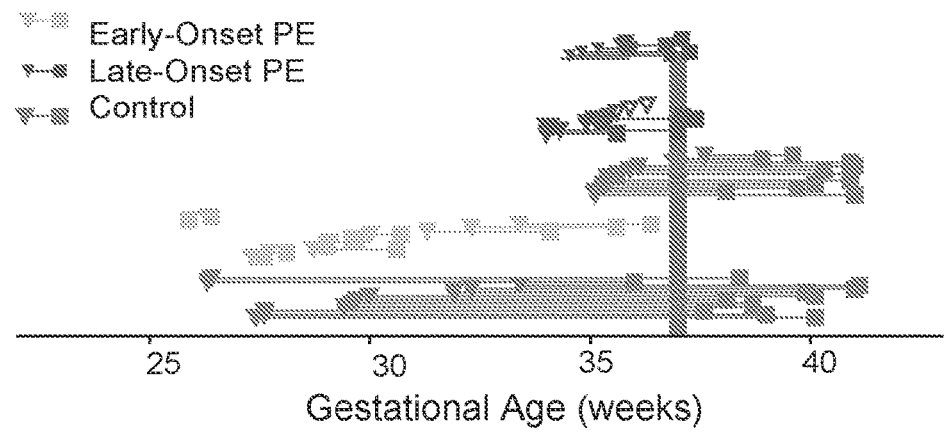
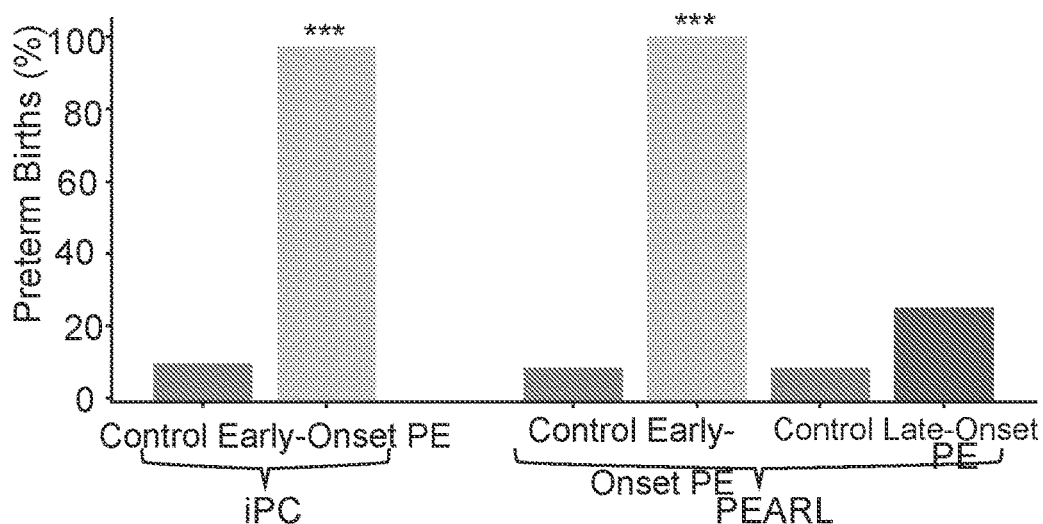
FIG. 23C

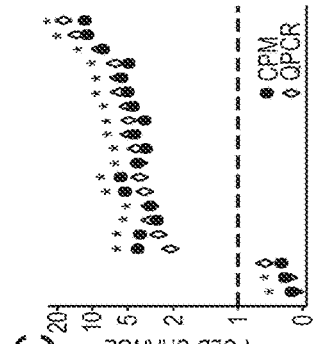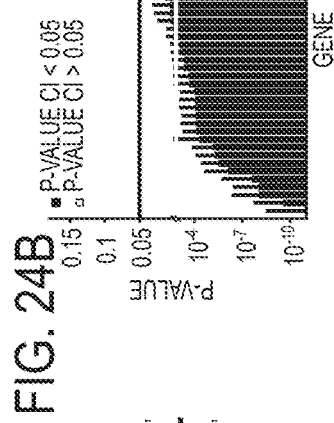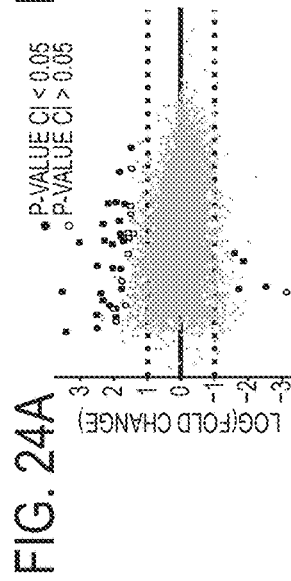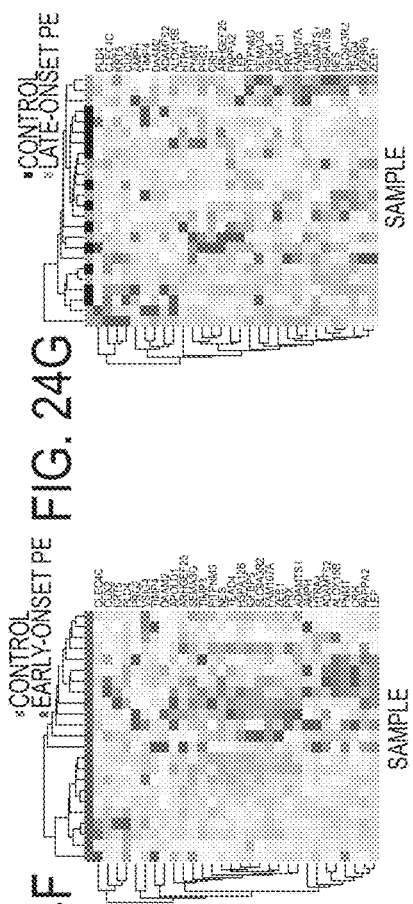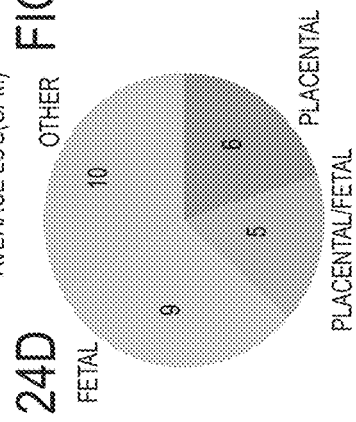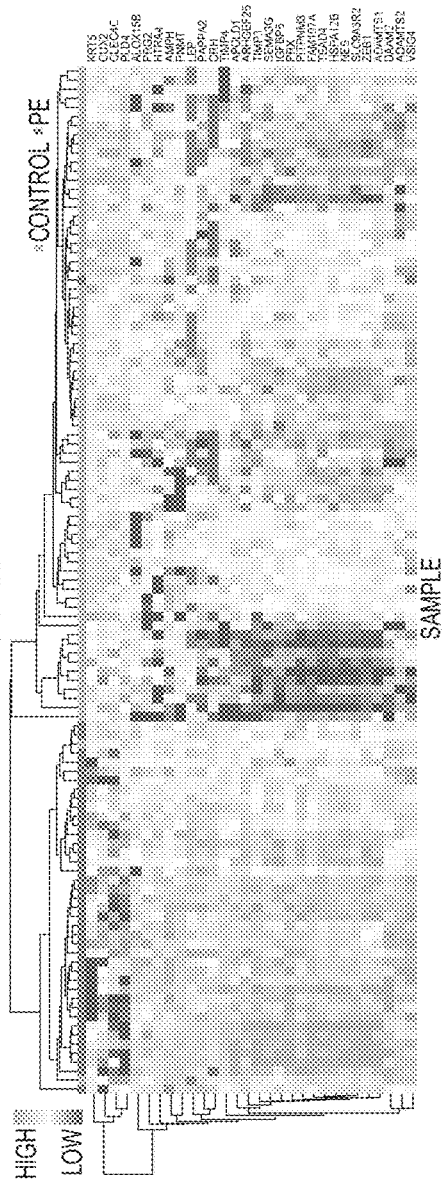
FIG. 24A FIG. 24B FIG. 24C FIG. 24D FIG. 24E FIG. 24F FIG. 24G

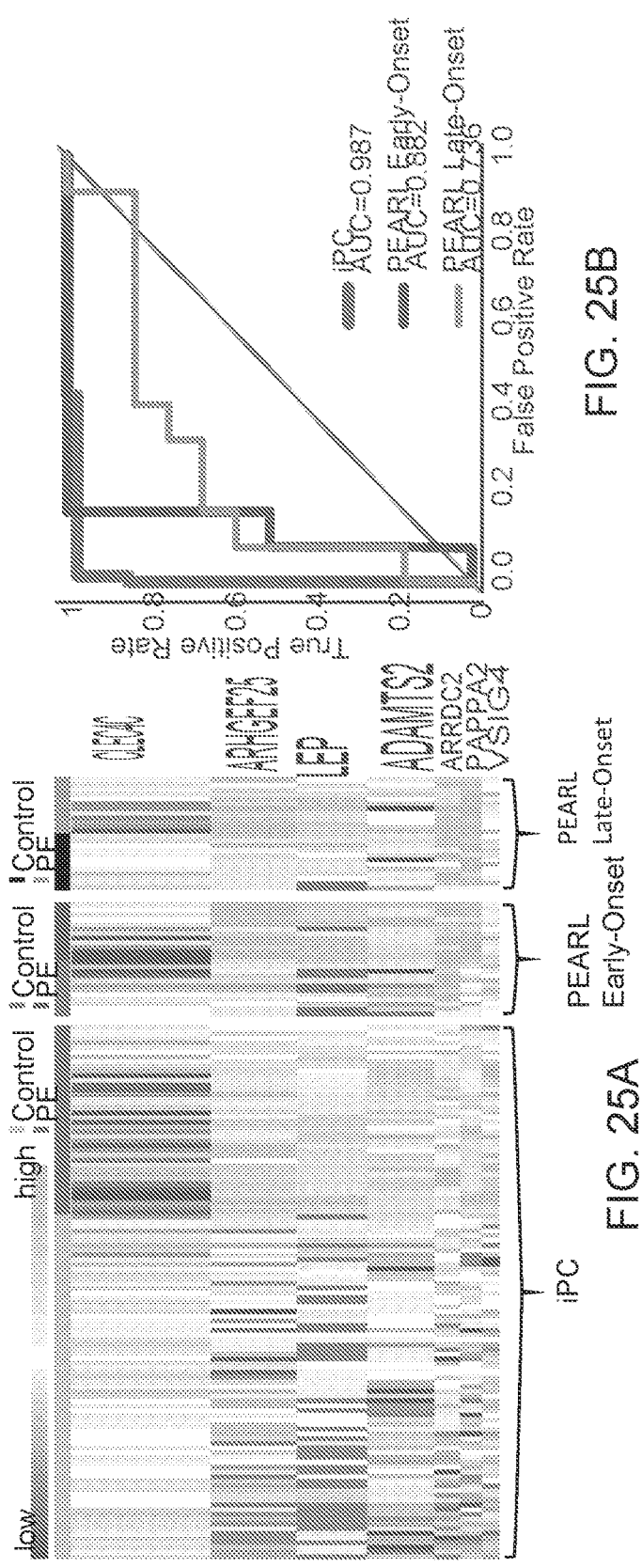
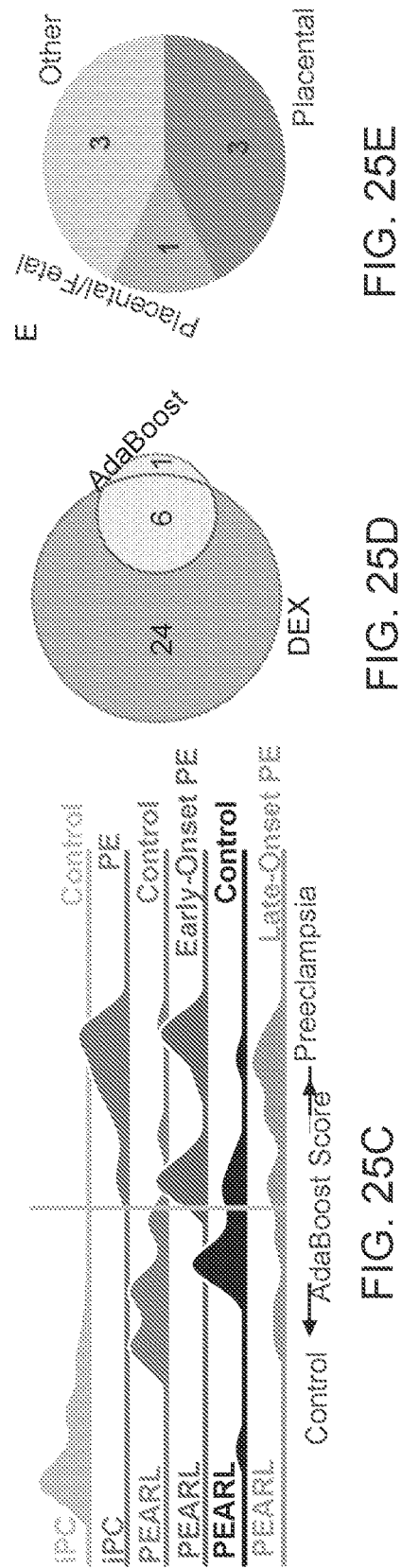
FIG. 25A
FIG. 25B
FIG. 25C
FIG. 25D
FIG. 25E

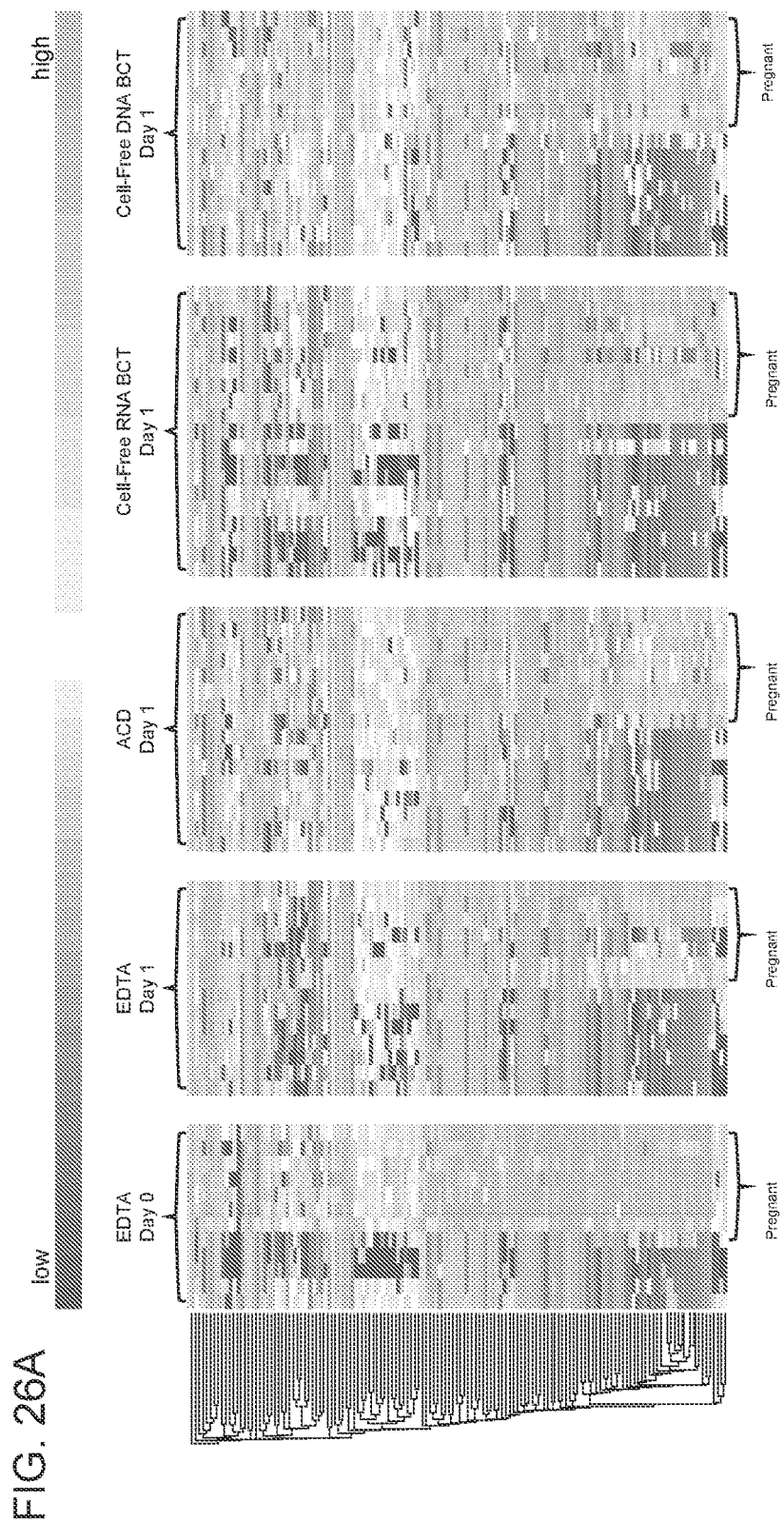
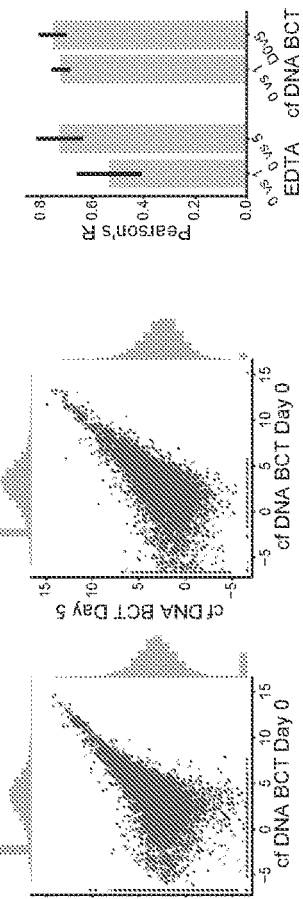
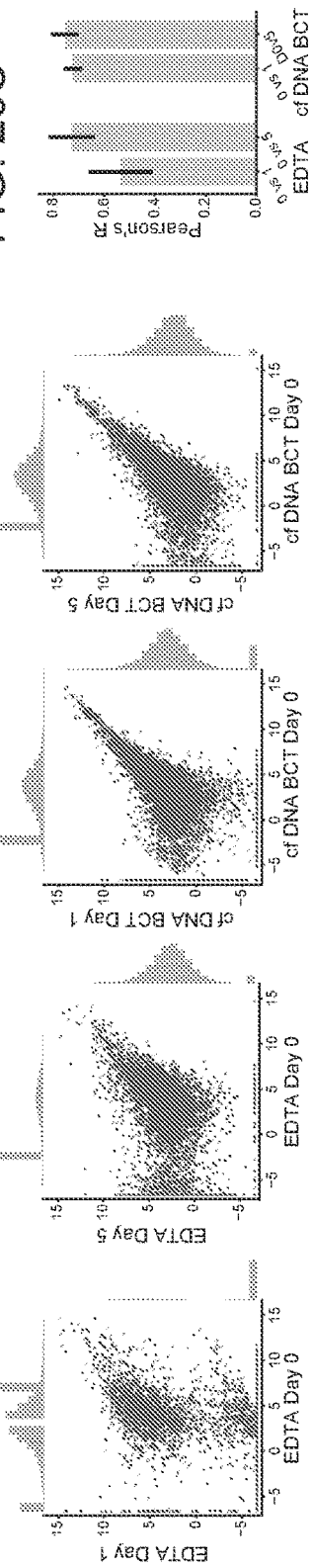

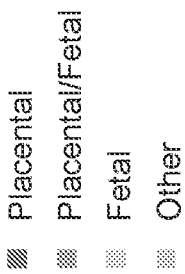
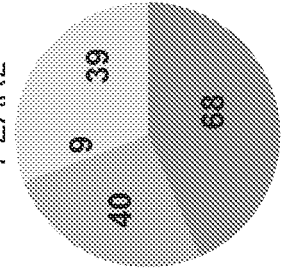
FIG. 28A
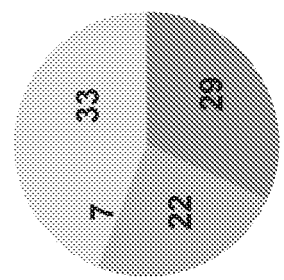
FIG. 28B
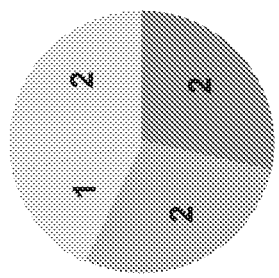
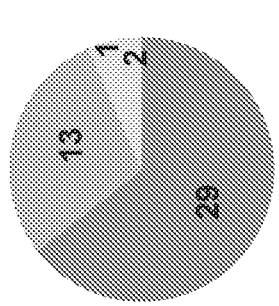
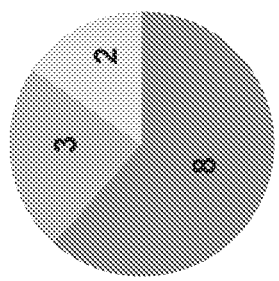
FIG. 28C

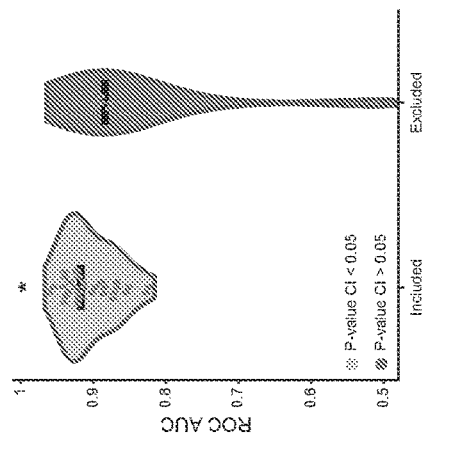
FIG. 29A
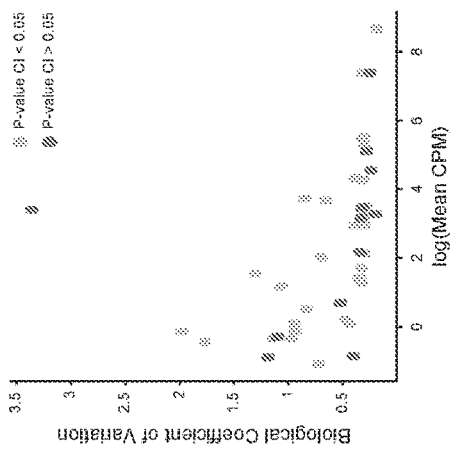
FIG. 29B
FIG. 29C
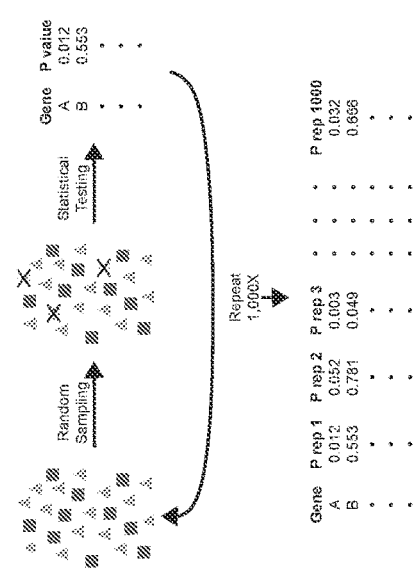
FIG. 29D
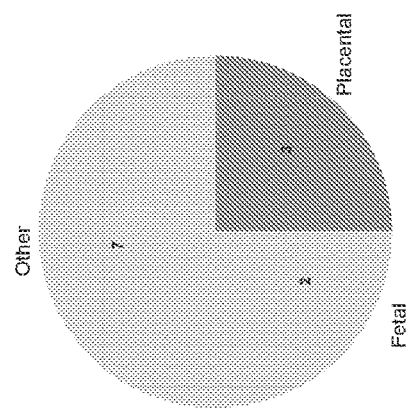
FIG. 29E
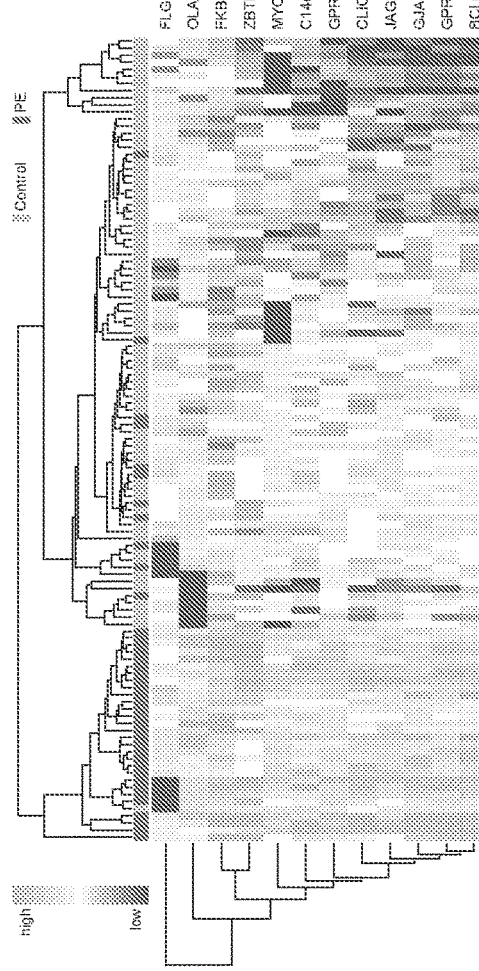

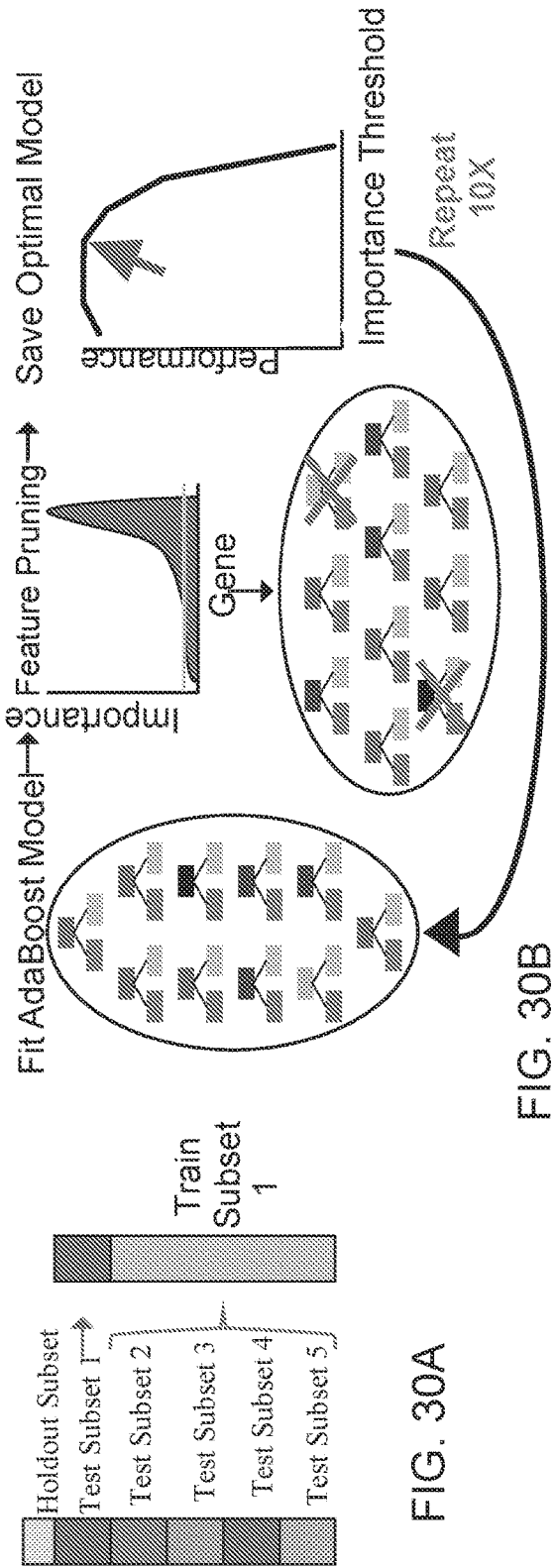
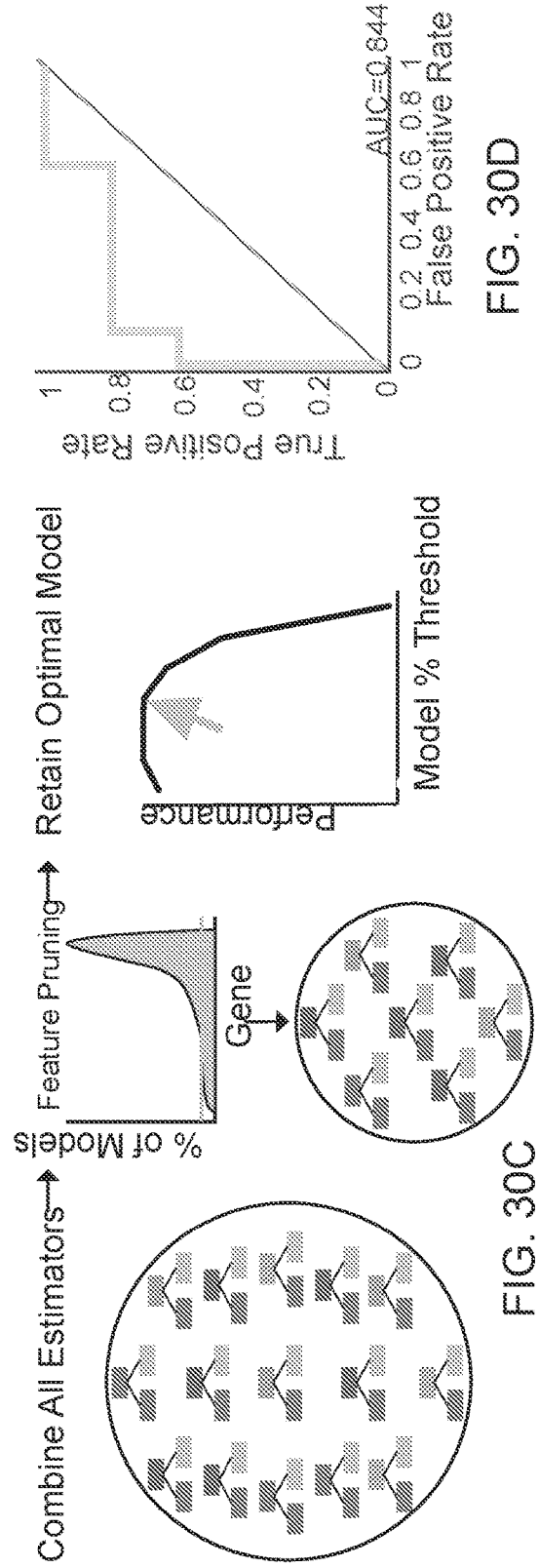
FIG. 30A
FIG. 30B
FIG. 30C
FIG. 30D

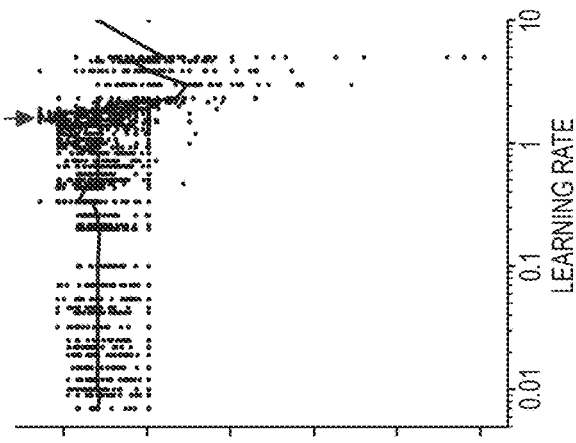
FIG. 31B
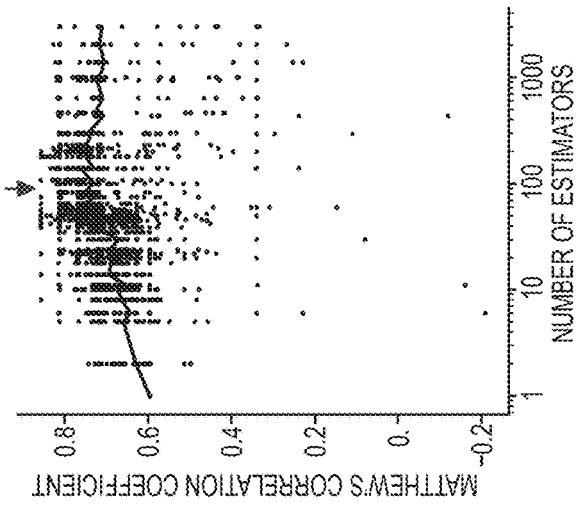
FIG. 31A
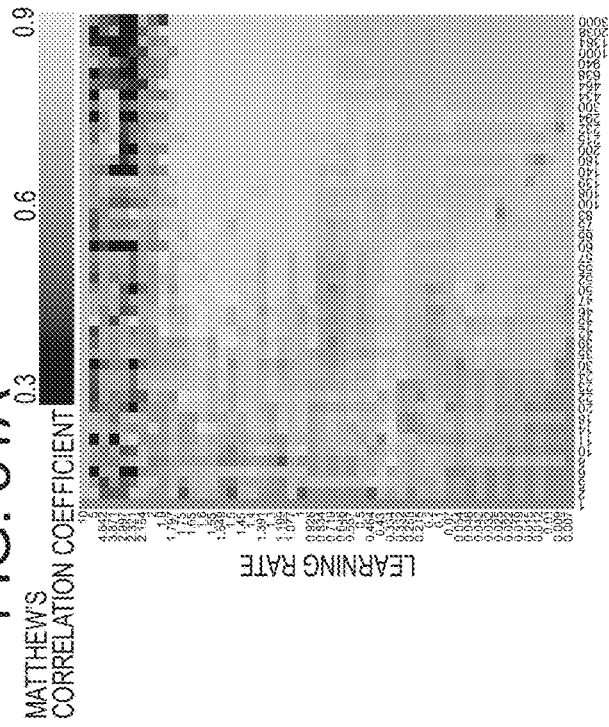
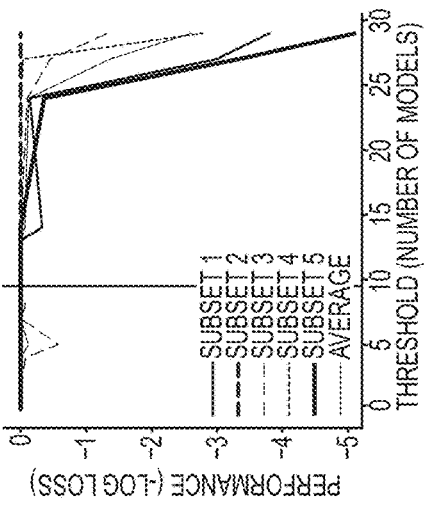
FIG. 31F
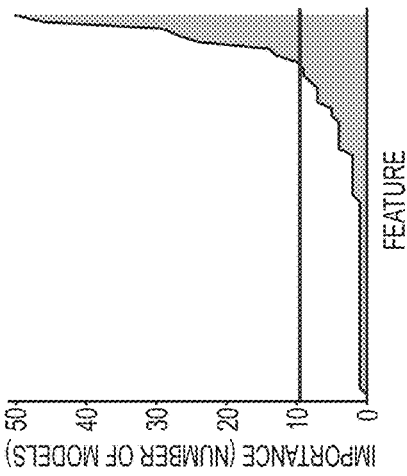
FIG. 31D
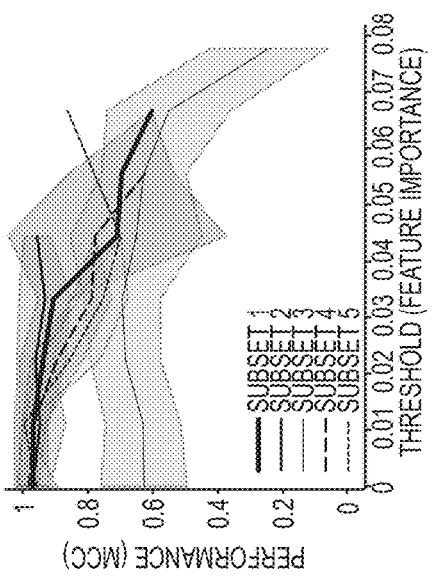
FIG. 31C

US 12,352,745 B2

CIRCULATING RNA SIGNATURES SPECIFIC TO PREECLAMPSIA

CONTINUING APPLICATION DATA

This application is the $371 U.S. National Stage of International Application No. PCT/US2019/033964, filed 24 May 2019, which claims the benefit of U.S. Provisional Application No. 62/676,436 filed May 25, 2018, and U.S. Provisional Application Ser. No. 62/848,219 filed May 15, 2019, the disclosures of which are incorporated by reference herein in their entireties.

FIELD OF INVENTION

The present invention relates generally to methods and materials for use in the detection and early risk assessment for the pregnancy complication preeclampsia.

BACKGROUND

Preeclampsia is a condition that occurs only during pregnancy, affecting 5% to 8% of all pregnancies. It is the direct cause of 10%-15% of maternal deaths and 40% of fetal deaths. The three main symptoms of preeclampsia may include high blood pressure, swelling of hands and feet, and excess protein in the urine (proteinuria), occurring after week 20 of pregnancy. Other signs and symptoms of preeclampsia may include severe headaches, changes in vision (including temporary loss of vision, blurred vision or light sensitivity), nausea or vomiting, decreased urine output, decreased platelets levels (thrombocytopenia), impaired liver function, and shortness of breath, caused by fluid in the lung.

The more severe the preeclampsia and the earlier it occurs in pregnancy, the greater the risks for mother and baby. Preeclampsia may require induced labor and delivery or delivery by cesarean delivery. Left untreated, preeclampsia can lead to serious, even fatal, complications for both the mother and baby. Complications of preeclampsia include fetal growth restriction, low birth weight, preterm birth, placental abruption, HELLP syndrome (hemolysis, elevated liver enzymes, and low platelet count syndrome), eclampsia (a severe form of preeclampsia that leads to seizures), organ damage, including kidney, liver, lung, heart, or eye damage, stroke or other brain injury. See, for example, "Preeclampsia—Symptoms and causes—Mayo Clinic," Apr. 3, 2018, available at on the worldwide web at mayoclinic.org/diseases-conditions/preeclampsia/symptoms-causes/syc-20355745.

With early detection and treatment, most women can deliver a healthy baby if preeclampsia is detected early and treated with regular prenatal care. Although various protein biomarkers display changed levels in maternal serum at presymptomatic stages, these biomarkers lack discriminative and predictive power in individual patients (Karumanchi and Granger, 2016, *Hypertension;* 67(2): 238-242). Thus, the identification of biomarkers for the early detection of preeclampsia is critical for the early diagnosis and treatment of preeclampsia.

SUMMARY OF THE INVENTION

The present invention includes a method of detecting preeclampsia and/or determining an increased risk for preeclampsia in a pregnant female, the method including:

identifying in a biosample obtained from the pregnant women a plurality of circulating RNA (C-RNA) molecules;

wherein a plurality of C-RNA molecules is selected from:
(a) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or
(b) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or
(c) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5; or (d) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) a plurality of C-RNA molecules encoding at least a portion of a protein selected from any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1 is indicative of preeclampsia and/or an increased risk for preeclampsia in the pregnant women.

The present invention includes a method of detecting preeclampsia and/or determining an increased risk for preeclampsia in a pregnant female, the method including:
obtaining a biosample from the pregnant female;
purifying a population of circulating RNA (C-RNA) molecules from the biosample;
identifying protein coding sequences encoded by the C-RNA molecules within the purified population of C-RNA molecules;
wherein protein coding sequences encoded by the C-RNA molecules encoding at least a portion of a protein is selected from:
(a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy or more, or all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy-five or more, any one hundred or more, or all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5; or (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1 is indicative of preeclampsia and/or an increased risk for preeclampsia in the pregnant women.

In some aspects, identifying protein coding sequences encoded by C-RNA molecules within the biosample includes hybridization, reverse transcriptase PCR, microarray chip analysis, or sequencing.

In some aspects, identifying protein coding sequences encoded by the C-RNA molecules within the biosample includes sequencing, including, for example, massively parallel sequencing of clonally amplified molecules and/or RNA sequencing.

In some aspects, the method further includes removing intact cells from the biosample; treating the biosample with a deoxynuclease (DNase) to remove cell free DNA (cfDNA); synthesizing complementary DNA (cDNA) from C-RNA molecules in the biosample; and/or enriching the cDNA sequences for DNA sequences that encode proteins by exome enrichment prior to identifying protein coding sequence encoded by the circulating RNA (C-RNA) molecules.

The present invention includes a method of detecting preeclampsia and/or determining an increased risk for preeclampsia in a pregnant female, the method including:
  obtaining a biological sample from the pregnant female;
  removing intact cells from the biosample;
  treating the biosample with a deoxynuclease (DNase) to remove cell free DNA (cfDNA);
  synthesizing complementary DNA (cDNA) from RNA molecules in the biosample;
  enriching the cDNA sequences for DNA sequences that encode proteins (exome enrichment);
  sequencing the resulting enriched cDNA sequences; and
  identifying protein coding sequences encoded by enriched C-RNA molecules;
  wherein protein coding sequences encoded by the C-RNA molecules encoding at least a portion of a protein selected from:
  (a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or
  (b) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or
  (c) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5; or
  (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1 is indicative of preeclampsia and/or an increased risk for preeclampsia in the pregnant women.

The present invention includes a method of identifying a circulating RNA signature associated with an increased risk of preeclampsia, the method including obtaining a biological sample from the pregnant female; removing intact cells from the biosample; treating the biosample with a deoxynuclease (DNase) to remove cell free DNA (cfDNA); synthesizing complementary DNA (cDNA) from RNA molecules in the biosample; enriching the cDNA sequences for DNA sequences that encode proteins (exome enrichment); sequencing the resulting enriched cDNA sequences; and identifying protein coding sequences encoded by enriched C-RNA molecules.

The present invention includes a method including:
  obtaining a biological sample from the pregnant female;
  removing intact cells from the biosample;
  treating the biosample with a deoxynuclease (DNase) to remove cell free DNA (cfDNA); synthesizing complementary DNA (cDNA) from RNA molecules in the biosample;
  enriching the cDNA sequences for DNA sequences that encode proteins (exome enrichment);
  sequencing the resulting enriched cDNA sequences; and
  identifying protein coding sequences encoded by the enriched C-RNA molecules;
  wherein the protein coding sequences include at least a portion of a protein selected from:
  (a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five up to all seventy-five ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5; or (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or any one or more, any two or more, any three or more, any four or more, (f) any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1.

In some aspects, the biosample includes plasma.

In some aspects, the biosample is obtained from a pregnant female at less than 16 weeks gestation or at less than 20 weeks gestation.

In some aspects, the biosample is obtained from a pregnant female at greater than 20 weeks gestation.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy or more, up to all seventy-five ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4.

The present invention includes a circulating RNA (C-RNA) signature for an elevated risk of preeclampsia, the C-RNA signature encoding a least a portion of a plurality of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES, including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1.

The present invention includes a solid support array comprising a plurality of agents capable of binding and/or identifying a C-RNA signature as described herein.

The present invention includes a kit comprising a plurality of probes capable of binding and/or identifying a C-RNA signature as described herein.

The present invention includes a kit comprising a plurality of primers for selectively amplifying a C-RNA signature as described herein.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "template" and "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, "amplify," "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the target nucleic acid molecule. The target nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as Mg' or Mn' and can also include various modifiers of ionic strength.

As used herein, the term "polymerase chain reaction" (PCR) refers to the method of K. B. Mullis U.S. Pat. Nos. 4,683,195 and 4,683,202, which describes a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double-stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified." In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or antisense) and double-stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the terms "library" and "sequencing library" refer to a collection or plurality of template molecules which share common sequences at their 5' ends and common sequences at their 3' ends. The collection of template molecules containing known common sequences at their 3' and 5' ends may also be referred to as a 3' and 5' modified library.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, PCR, rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complimentary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "sensitivity" as used herein is equal to the number of true positives divided by the sum of true positives and false negatives.

The term "specificity" as used herein is equal to the number of true negatives divided by the sum of true negatives and false positives.

The term "enrich" herein refers to the process of amplifying nucleic acids contained in a portion of a sample. Enrichment includes specific enrichment that targets specific sequences, e.g., polymorphic sequences, and non-specific enrichment that amplifies the whole genome of the DNA fragments of the sample.

As used herein, the term "each," when used in reference to a collection of items, is intended to identify an individual item in the collection but does not necessarily refer to every item in the collection unless the context clearly dictates otherwise.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 8. Classification of PE without any selection of genes, relying of entire data set.

FIG. 20. Identifying C-RNA signatures specific to preeclampsia in Nextera Flex generated libraries using standard TREAT analysis and jackknifing approach.

FIG. 22A is a schematic of the sequencing library preparation method; all steps after blood collection can be performed in a centralized processing lab. Temporal changes of transcripts altered throughout the course of pregnancy (FIG. 22B). Overlap of genes identified in C-RNA pregnancy progression studies (FIG. 22C). Tissues expressing the 91 genes unique to the pregnancy time course study (FIG. 22D).

FIGS. 23A-23C. Sample collection for PE clinical studies. Panels illustrate the time of blood collection (triangles) and gestational age at birth (squares) for each individual in the iPC study (FIG. 23A) and the PEARL study (FIG. 23B). The red line indicates the threshold for term birth. Preterm birth rates are significantly elevated in early-onset PE cohorts (FIG. 23C). *** $p<0.001$ by Fisher's exact test.

FIGS. 24A-24G. Differential analysis of C-RNA identifies preeclampsia biomarkers. Fold change and abundance of transcripts altered in PE (FIG. 24A). One-sided confidence p-value intervals were calculated after jackknifing for each gene detected by standard analysis methods (FIG. 24B). Transcript abundance fold-change determined by whole exome sequencing and by qPCR for (21) genes (FIG. 24C). * $p<0.05$ by Student's T-test. Tissue distribution of affected genes (FIG. 24D). Hierarchical clustering of iPC samples (average linkage, squared Euclidean distance) (FIG. 24E). Clustering of early-onset PE (FIG. 24F) and late-onset PE (FIG. 24G) samples from the PEARL study.

FIGS. 25A-25E. AdaBoost classifies preeclampsia samples across cohorts. Heatmap illustrating the relative abundance of the transcripts used by machine learning in each cohort (FIG. 25A). The height of each block reflects each gene's importance. ROC curves for each dataset (FIG. 25B). Distributions (KDE) of AdaBoost Scores. The orange line indicates the optimal boundary to discriminate PE and control samples (FIG. 25C). Concordance of genes identified by differential analysis and those used in AdaBoost (FIG. 25D). Tissue distribution of AdaBoost genes (FIG. 25E).

FIGS. 26A-26C. C-RNA data integrity when blood is stored in different collection tubes. Comparing the abundance of previously detected C-RNA pregnancy markers from blood stored overnight in different tube types to immediate processing after collection in EDTA tubes (FIG. 26A). Scatterplots comparing transcript FPKM values for C-RNA prepared from the same individual after different blood storage durations (FIG. 26B). Pearson's correlation coefficient, R, is more variable when using EDTA tubes (cf, Cell-Free) (FIG. 26C).

FIGS. 28A-28C. Pregnancy marker tissue specificity. Pie charts showing tissue specificity of the genes detected in pregnancy by three independent studies, using either the full set of altered genes (FIG. 28A), the transcripts unique to each study (FIG. 28B), or intersecting gene sets (FIG. 28C).

FIGS. 29A-29E. Jackknifing excludes genes that are not universally altered in preeclampsia. Schematic of the jackknifing approach used to determine how consistently transcripts were altered across PE samples (FIG. 29A). Average abundance and noise for each differentially abundant gene (FIG. 29B). ROC area under the curve values for each affected transcript provide a measure of how separated C-RNA transcript abundance distributions are for control and PE samples (FIG. 29C). * p<0.05 by Mann-Whitney U test. Hierarchical clustering of iPC samples using the genes excluded after jackknifing (FIG. 29D). Tissue distribution of excluded transcripts (FIG. 29E). The decreased contribution of the fetus and placenta may suggest the maternal component of PE is most variable between individuals.

FIGS. 30A-30D. AdaBoost model development strategy. The RGH014 dataset was divided into 6 pieces (FIG. 30A). The "Holdout Subset" contained 10% of the samples (randomly selected) as well as the 3 samples which were incorrectly clustered when using differentially abundant genes (as with FIG. 24C) and was fully excluded from model building. The remaining samples were divided at random into 5 evenly sized "Test Subsets." For each test subset, training data was composed of all non-holdout and non-testing samples. Gene counts for training and testing data were TMM-normalized in edgeR, and then standardized to mean 0 and standard deviation 1 for each gene. For each train/test sample set, AdaBoost models (90 estimators, 1.6 learning rate) were built 10 times from the training data (FIG. 30B). Feature pruning was performed, removing genes below an incrementally increasing importance threshold and assessing performance by Matthew's correlation coefficient when predicting testing data. The model with the best performance—and fewest genes, in the case of a tie—was retained. Estimators from all 50 independent models were combined into a single AdaBoost model (FIG. 30C). Feature pruning was performed on the resulting ensemble, this time using the percent of models which used a gene to set threshold values and performance measured by average log loss value across test subsets. ROC curve after applying the final AdaBoost model to the holdout data (FIG. 30D). All samples segregated correctly, except for two of the three samples which also misclustered by HCA.

FIGS. 31A-31E. The effect of hyperparameter selection and feature pruning on machine learning performance. Heatmap of a grid search to identify the optimal hyperparameters for AdaBoost (FIG. 31A). Matthew's correlation coefficient was used as a measure of performance. Flattened views of performance for each hyperparameter (FIG. 31B). Arrows indicate the values selected for model construction. FIG. 31C shows the impact of pruning individual AdaBoost models on performance (as in FIG. 30B). Solid lines are the average for all 10 models, and the shaded region shows the standard deviation. The number of AdaBoost models using each gene observed in the pre-pruned ensemble (FIG. 31D). Model performance when pruning the combined AdaBoost ensemble (FIG. 31E). The orange lines in FIG. 31D and FIG. 31E show the threshold applied to generate the final AdaBoost model.

Figure 1:
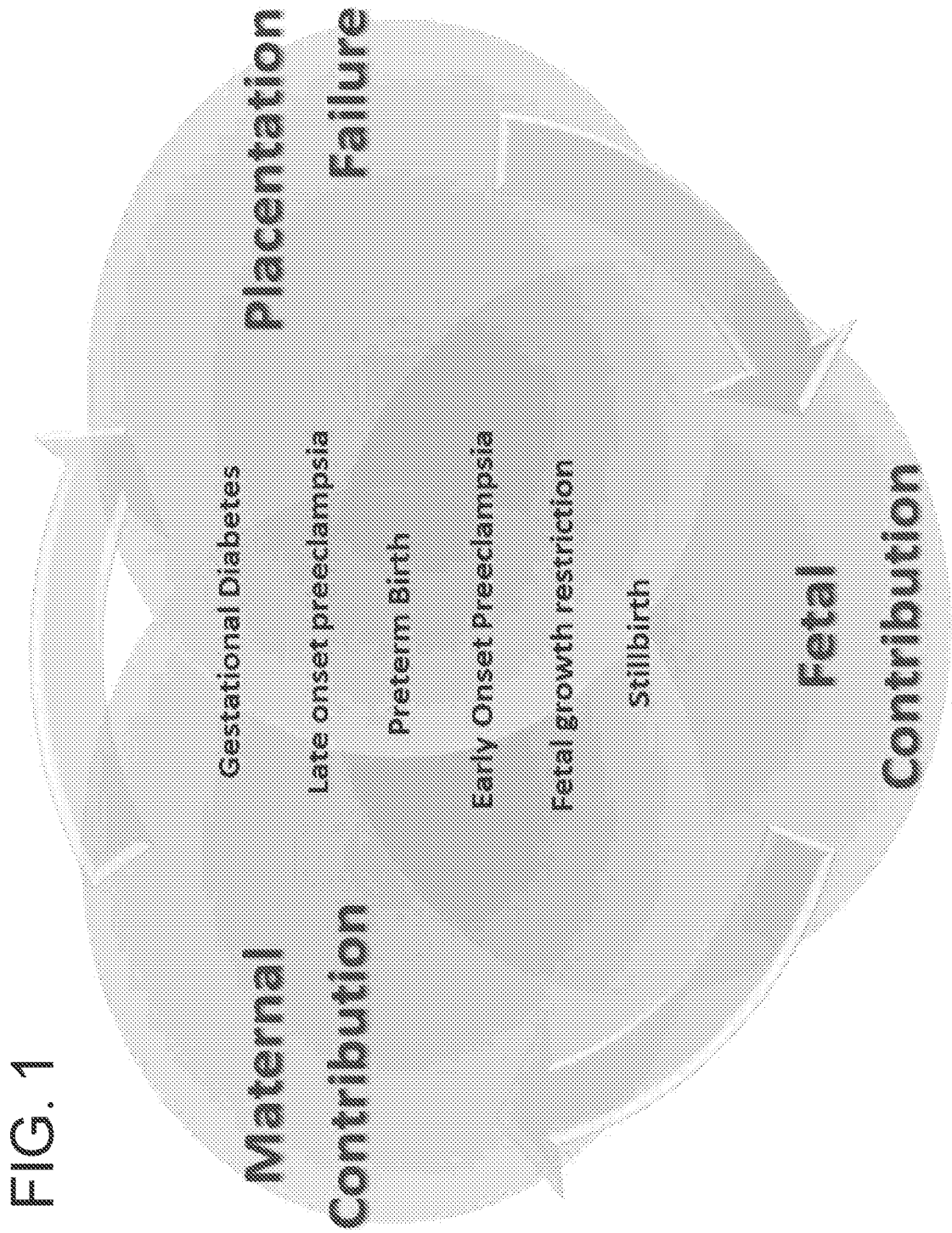
FIG. 1. A schematic of the relationships between placental health, maternal response, and fetal response.

The schematic drawings are not necessarily to scale. Like numbers used in the figures may refer to like components. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Provided herein are signatures of circulating RNA found in the maternal circulation that are specific to preeclampsia and the use of such signatures in noninvasive methods for the diagnosis of preeclampsia and the identification of pregnant women at risk for developing preeclampsia.

While most of the DNA and RNA in the body is located within cells, extracellular nucleic acids can also be found circulating freely in the blood. Circulating RNA, also referred to herein as "C-RNA," refers to extracellular segments of RNA found in the bloodstream. C-RNA molecules originate predominately from two sources: one, released into the circulation from dying cells undergoing apoptosis, and two, contained within exosomes shed by living cells into the circulation. Exosomes are small membranous vesicles about 30-150 nm of diameter released from many cell types into the extracellular space and are found in a wide variety of body fluids, including serum, urine, and breast milk and carrying protein, mRNA, and microRNA. The lipid bilayer structure of exosomes protects the RNAs contained within from degradation by RNases, providing for stability in blood. See, for example, Huang et al., 2013, *BMC Genomics;* 14:319; And Li et al., 2017, *Mol Cancer;* 16:145). Evidence is accumulating that exosomes have specialized functions and play a role in such processes as coagulation, intercellular signaling, and waste management (van der Pol et al., 2012, *Pharmacol Rev;* 64(3):676-705). See, also, Samos et al., 2006, *Ann N Y Acad Sci;* 1075:165-173; Zernecke et al., 2009, *Sci Signal;* 2:ra81; Ma et al., 2012, *J Exp Clin Cancer Res;* 31:38; and Sato-Kuwabara et al., 2015, *Int J Oncol;* 46:17-27.

With the methods described herein, the C-RNA molecules found in maternal circulation function as biomarkers of fetal, placental, and maternal health and provide a window into the progression of pregnancy. Described herein are C-RNA signatures within the maternal circulation that are indicative of pregnancy, C-RNA signatures within the maternal circulation that are temporally associated with the gestational stage of pregnancy, and C-RNA signatures within the maternal circulation that are indicative of the pregnancy complication preeclampsia.

A C-RNA signature within the maternal circulation indicative of preeclampsia includes a plurality of C-RNA molecules encoding at least a portion of a plurality of proteins selected from ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3. This C-RNA signature is the Adaboost General signature obtained with the TruSeq library prep method shown in Table 1 below, also referred to herein as "list (a)" or "(a)."

A C-RNA signature within the maternal circulation indicative of preeclampsia includes a plurality of C-RNA molecules encoding at least a portion of a plurality of proteins selected from TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4. This C-RNA signature is the Bootstrapping signature obtained with the TruSeq library prep method shown in Table 1 below, also referred to herein as "list (b)" or "(b)."

A C-RNA signature within the maternal circulation indicative of preeclampsia includes a plurality of C-RNA molecules encoding at least a portion of a protein selected from CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5. This C-RNA signature is the Standard DEX Treat signature obtained with the TruSeq library prep method shown in Table 1 below, also referred to herein as "list (c)" or "(c)."

A C-RNA signature within the maternal circulation indicative of preeclampsia includes a plurality of C-RNA molecules encoding at least a portion of a protein selected from VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4. This C-RNA signature is the Jacknifing signature obtained with the TruSeq library prep method shown in Table 1 below, also referred to herein as "list (d)" or "(d)."

A C-RNA signature within the maternal circulation indicative of preeclampsia includes a plurality of C-RNA molecules encoding at least a portion of a protein selected from ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4. This C-RNA signature is the Standard DEX Treat signature obtained with the Nextera Flex for Enrichment library prep method shown in Table 1 below, also referred to herein as "list (e)" or "(e)."

A C-RNA signature within the maternal circulation indicative of preeclampsia includes a plurality of C-RNA molecules encoding at least a portion of a protein selected from ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4. This C-RNA signature is the Jacknifing signature obtained with the Nextera Flex for Enrichment library prep method shown in Table 1 below, also referred to herein as "list (f)" or "(f)."

A C-RNA signature within the maternal circulation indicative of preeclampsia includes a plurality of C-RNA molecules encoding at least a portion of a protein selected from CLEC4C, ARHGEF25, ADAMTS2, LEP, ARRDC2, SKIL, PAPPA2, VSIG4, ARRDC4, CRH, and NES. This C-RNA signature is the Adaboost Refined TruSeq signature obtained with the TruSeq library prep method shown in Table 1 below, also referred to herein as "AdaBoost Refined 1," "list (g)," or "(g)."

In some embodiments, a C-RNA signature within the maternal circulation indicative of preeclampsia includes C-RNA molecules encoding at least a portion of a protein selected from ADAMTS2, ARHGEF25, ARRDC2, CLEC4C, LEP, PAPPA2, and VSIG4 (also referred to herein as "AdaBoost Refined 2"), ADAMTS2, ARHGEF25, ARRDC2, CLEC4C, LEP, PAPPA2, SKIL, and VSIG4 (also referred to herein as "AdaBoost Refined 3"), ADAMTS2, ARHGEF25, ARRDC4, CLEC4C, LEP, NES, SKIL, and VSIG4 (also referred to herein as "AdaBoost Refined 4"), ADAMTS2, ARHGEF25, ARRDC2, ARRDC4, CLEC4C, CRH, LEP, PAPPA2, SKIL, and VSIG4 (also referred to herein as "AdaBoost Refined 5"), ADAMTS2, ARHGEF25, ARRDC2, CLEC4C, LEP, and SKIL (also referred to herein as "AdaBoost Refined 6"), or ADAMTS2, ARHGEF25, ARRDC2, ARRDC4, CLEC4C, LEP, PAPPA2, and SKIL (also referred to herein as "AdaBoost Refined 7").

A C-RNA signature within the maternal circulation indicative of preeclampsia includes a plurality of C-RNA molecules encoding at least a portion of a protein selected from LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1. This C-RNA signature is the Adaboost Refined Nextera Flex signature obtained with the Nextera Flex for Enrichment library prep method shown in Table 1 below, also referred to herein as "list (h)" or "(h)."

In some embodiments, a C-RNA signature within the maternal circulation indicative of preeclampsia includes a plurality of C-RNA molecules encoding at least a portion of a protein selected from of any one or more of any of (a), (b), (c), (d), (e), (f), (g), and/or (h) in combination with any one or more of any of (a), (b), (c), (d), (e), (f), (g), and/or (h).

The Examples provided herewith describe the eight gene lists summarized above that distinguish preeclampsia and control pregnancies. Each was identified by using different analysis methods and/or distinct datasets. However, there is a high degree of concordance between many of these gene sets. Identifying a transcript as altered in preeclampsia C-RNA with multiple approaches indicates that said transcript has higher predictive value for classification of this disease. Thus, the importance of the transcripts identified by all differential expression analyses and by all AdaBoost models was combined and ranked. Genes assigned lower ranks are not unimportant or uninformative, but they may be less robust for classification of preeclampsia across cohorts and sample preparations.

First, the transcripts identified when using all differential expression analyses (Standard DEX Treat, bootstrapping and the jackknifing) for both library preparation methods (TruSeq and Nextera Flex for Enrichment) were combined. Table 2 below shows the relative importance for all of the 125 transcripts identified by the different analysis methods. Transcripts identified across every analysis method and both library preparations are the strongest classifiers and assigned an importance ranking of 1. Transcripts that were identified by three or more analysis methods and were detected with both library preparations were given an importance ranking of 2. Transcripts identified by the most stringent analysis method, jackknifing but only one of the library preparations were assigned an importance ranking of 3. Transcripts identified in two of the five analysis methods were given an importance ranking of 4. Transcripts that were only identified in the Standard DEX Treat method, the most broad and inclusive analysis, were given the lowest importance ranking of 5.

Then, the 91 transcripts identified across all AdaBoost models (AdaBoost General and AdaBoost Refined) and both library preparations (Table 3 below) were combined. When generating the refined AdaBoost models for each library preparation, observed slight variations had been observed in the gene set obtained each time a model was built from the same data. This is a natural result of randomness used by AdaBoost to search through the large whole-exome C-RNA data. To obtain a representative list of genes, model building for refined AdaBoost was run a minimum of nine separate times and all genes used by one or more models reported. The percent of models that included each transcript are reported in Table 3 (Frequency Used By AdaBoost). AdaBoost assigns its own "importance" value to each transcript, which reflects how much the abundance of that transcript influences determining whether a sample is from a preeclampsia patient. These AdaBoost importance values were averaged across each refined AdaBoost model a given transcript was used by (Table 3, Average AdaBoost Model Importance).

Transcripts identified across all AdaBoost analyses and library preparations were assigned the highest importance ranking of 1. Transcripts identified in the refined AdaBoost model for a single library preparation method with over 90% frequency used by AdaBoost were assigned an importance ranking of 2. Generally, these transcripts also have higher AdaBoost model importance, consistent with increased predictive capabilities. Transcripts identified in the refined AdaBoost model for a single library preparation method but used by less than 90% of AdaBoost models were assigned an importance ranking of 3. Transcripts identified only in the general AdaBoost model for a single library preparation were given the lowest importance ranking of 4.

Table 2 lists every gene identified by DEX analysis across all analysis approaches and library preps. Rank 1=Transcript identified across every analysis method and library prep method. Rank 2=Transcript identified both library preps, and 3/5 analysis methods. Rank 3=Identified in one library prep method, in jacknifing, are most stringent analysis. Rank 4=identified in 2/5 analyses. And, Rank 5=Only identified in Standard DEX Treat method, our most relaxed analysis method.

Table 3 lists every gene identified by Adaboost analysis across both library preps. Rank 1=identified in both library prep methods and the refined adaboost models. Rank 2=Identified in one library prep method, present in refined adaboost model with high model importance and frequency. Rank 3=identified in one library prep method, present in refined adaboost model with medium model importance and frequency. And, Rank 4=Identified in one library prep, not present in the refined adaboost model.

Table 4 below is a glossary of all of the various genes recited herein. The information was obtained from the HUGO Gene Nomenclature Committee at the European Bioinformatics Institute.

TABLE 1

Composite Gene Listing

| | DIFFERENTIAL EXPRESSION APPROACHES | | | | | Machine Learning Approaches | | |
|---|---|---|---|---|---|---|---|---|
| Standard DEX TREAT Library Prep: TruSeq Broadest DEX list for TST170 122 genes | Bootstrapping Library Prep: TruSeq Refined subset of Standard DEX TREAT 27 genes | Jackknifing Library Prep: TruSeq Refined subset of Standard DEX TREAT 30 genes | Standard DEX TREAT Library Prep: Nextera Flex for Enrichment Broadest DEX list for Nextera 26 genes | Jackknifing Library Prep: Nextera Flex for Enrichment Refined subset of Standard DEX TREAT for Nextera 22 genes | Adaboost General Library Prep: TruSeq Broadest adaboost 75 genes | Adaboost Refined Library Prep: TruSeq Imrpoved model building for Adaboost, to improve unverisal signal 11 genes | Adaboost Refined Nextera Flex Library Prep: Nextera Flex for Enrichment Imrpoved model building for Adaboost, to improve unverisal signal 24 genes |
| FLG | FLG | VSIG4 | ADAMTS1 | ADAMTS1 | ARHGEF25 | CLEC4C | LEP |
| KRT5 | KRT5 | ADAMTS2 | ADAMTS2 | ADAMTS2 | CLEC4C | ARHGEF25 | PAPPA2 |
| HBG2 | CLEC4C | NES | ALOX15B | ALOX15B | CRH | ADAMTS2 | KCNA5 |
| NXF3 | TEAD4 | FAM107A | AMPH | ARHGEF25 | CUX2 | LEP | ADAMTS2 |
| CLEC4C | SEMA3G | LEP | ARHGEF25 | CELF4 | LEP | ARRDC2 | MYOM3 |
| BPIFB3 | ADAMTS1 | DAAM2 | CELF4 | DAAM2 | NES | SKIL | ATP13A3 |
| LAMP5 | IGFBP5 | ARHGEF25 | DAAM2 | FAM107A | PAPPA2 | PAPPA2 | ARHGEF25 |
| CADM2 | HSPA12B | TIMP3 | FAM107A | HTRA4 | PRG2 | VSIG4 | ADA |
| CUX2 | SLC9A3R2 | PRX | HSPA12B | IGFBP5 | ACY3 | ARRDC4 | HTRA4 |
| PACSIN1 | PRX | ALOX15B | HTRA4 | KCNA5 | ADA | CRH | NES |
| PTGDR2 | TIMP3 | HSPA12B | IGFBP5 | KRT5 | ADAM17 | NES | CRH |
| PLD4 | ARHGEF25 | IGFBP5 | KCNA5 | LCN6 | ARFGAP3 | | ACY3 |
| NOMO1 | HTRA4 | CLEC4C | KRT5 | LEP | ARRDC2 | | PLD4 |
| SH3RF2 | NES | SLC9A3R2 | LCN6 | LRRC26 | ARRDC3 | | SCT |
| ZNF366 | TIMP4 | ADAMTS1 | LEP | NES | ASTE1 | | NOX4 |
| SH3PXD2A | PAPPA2 | SEMA3G | LRRC26 | OLAH | ATOH8 | | PACSIN1 |
| SULT2A1 | FAM107A | KRT5 | NES | PRX | ATP13A3 | | SERPINF1 |
| FAM219A | PRG2 | AMPH | OLAH | PTGDR2 | C10orf2 | | SKIL |

TABLE 1-continued

Composite Gene Listing

|  | DIFFERENTIAL EXPRESSION APPROACHES | | | | Machine Learning Approaches | | |
|---|---|---|---|---|---|---|---|
| Standard DEX TREAT Library Prep: TruSeq Broadest DEX list for TST170 122 genes | Bootstrapping Library Prep: TruSeq Refined subset of Standard DEX TREAT 27 genes | Jackknifing Library Prep: TruSeq Refined subset of Standard DEX TREAT 30 genes | Standard DEX TREAT Library Prep: Nextera Flex for Enrichment Broadest DEX list for Nextera 26 genes | Jackknifing Library Prep: Nextera Flex for Enrichment Refined subset of Standard DEX TREAT for Nextera 22 genes | Adaboost General Library Prep: TruSeq Broadest adaboost 75 genes | Adaboost Refined TruSeq Library Prep: TruSeq Imrpoved model building for Adaboost, to improve unverisal signal 11 genes | Adaboost Refined Nextera Flex Library Prep: Nextera Flex for Enrichment Imrpoved model building for Adaboost, to improve unverisal signal 24 genes |
| PPP1R3C | AMPH | PRG2 | PACSIN1 | SEMA3G | C22orf39 |  | SEMA3G |
| NFE2L1 | DAAM2 | PAPPA2 | PAPPA2 | SLC9A3R2 | CCDC151 |  | TIPARP |
| PODXL | LCN6 | TEAD4 | PRX | TIMP3 | CD63 |  | LRRC26 |
| HTRA1 | ALOX15B | CRH | PTGDR2 | VSIG4 | CKAP4 |  | PHEX |
| EMP1 | CRH | PITPNM3 | SEMA3G |  | CLCN1 |  | LILRA4 |
| H19 | VSIG4 | TIMP4 | SLC9A3R2 |  | CLEC4M |  | PER1 |
| IGIP | LEP | PNMT | TIMP3 |  | CLIC5 |  |  |
| SSUH2 | ADAMTS2 | ZEB1 | VSIG4 |  | CNFN |  |  |
| C6 | ARMS2 | APOLD1 |  |  | CPAMD8 |  |  |
| ARHGEF15 |  | PLD4 |  |  | DDI2 |  |  |
| IRF6 |  | CUX2 |  |  | EBI3 |  |  |
| NPR1 |  | HTRA4 |  |  | ELMO3 |  |  |
| ALPK3 |  |  |  |  | ENC1 |  |  |
| ZCCHC24 |  |  |  |  | ETV3 |  |  |
| SAMD4A |  |  |  |  | FAR2 |  |  |
| STAG3 |  |  |  |  | FOS |  |  |
| RP1L1 |  |  |  |  | FSTL3 |  |  |
| A1CF |  |  |  |  | GATSL2 |  |  |
| MN1 |  |  |  |  | GBP2 |  |  |
| CD34 |  |  |  |  | GINS4 |  |  |
| MYH14 |  |  |  |  | GSTA3 |  |  |
| TENC1 |  |  |  |  | HEATR9 |  |  |
| FSTL3 |  |  |  |  | HEG1 |  |  |
| PRDM16 |  |  |  |  | HIPK2 |  |  |
| FMO3 |  |  |  |  | JUN |  |  |
| UACA |  |  |  |  | LILRA4 |  |  |
| TEK |  |  |  |  | MRPS35 |  |  |
| SOX17 |  |  |  |  | MTRNR2L6 |  |  |
| FLNC |  |  |  |  | ORAI3 |  |  |
| TMC7 |  |  |  |  | PARN |  |  |
| KIF1C |  |  |  |  | PDE8B |  |  |
| CLIC5 |  |  |  |  | PI4KAP1 |  |  |
| SYNPO |  |  |  |  | PPP1R17 |  |  |
| CACNA1C |  |  |  |  | PSMD11 |  |  |
| ERG |  |  |  |  | RGP1 |  |  |
| PTPN21 |  |  |  |  | RNF6 |  |  |
| NTRK2 |  |  |  |  | SCAMP1 |  |  |
| WWTR1 |  |  |  |  | SERPINF1 |  |  |
| CYP26B1 |  |  |  |  | SKIL |  |  |
| ZEB1 |  |  |  |  | SLC26A2 |  |  |
| AIF1L |  |  |  |  | SLC4A3 |  |  |
| C8B |  |  |  |  | SLIT3 |  |  |
| KIF26A |  |  |  |  | SMPD3 |  |  |
| ZBTB16 |  |  |  |  | SPDYE5 |  |  |
| BCL6B |  |  |  |  | ST6GALNAC3 |  |  |
| FKBP5 |  |  |  |  | THTPA |  |  |
| FN1 |  |  |  |  | TIPARP |  |  |
| AQP7 |  |  |  |  | TMEM108 |  |  |
| IL1R2 |  |  |  |  | TMEM11 |  |  |
| ERRFI1 |  |  |  |  | TNFRSF21 |  |  |
| SRPX |  |  |  |  | TPCN1 |  |  |
| GJA5 |  |  |  |  | TPST1 |  |  |
| GPR116 |  |  |  |  | TRAF3IP1 |  |  |
| JAG2 |  |  |  |  | TRUB1 |  |  |
| MYL2 |  |  |  |  | TTC21A |  |  |
| ADCY1 |  |  |  |  | USP54 |  |  |
| NRG3 |  |  |  |  | ZMYM6 |  |  |
| GPR4 |  |  |  |  |  |  |  |
| PITPNM3 |  |  |  |  |  |  |  |
| SERPINA3 |  |  |  |  |  |  |  |
| CPB2 |  |  |  |  |  |  |  |
| ADRA2C |  |  |  |  |  |  |  |

TABLE 1-continued

Composite Gene Listing

| Standard DEX TREAT Library Prep: TruSeq Broadest DEX list for TST170 122 genes | DIFFERENTIAL EXPRESSION APPROACHES ||| | Machine Learning Approaches |||
|---|---|---|---|---|---|---|---|
| | Bootstrapping Library Prep: TruSeq Refined subset of Standard DEX TREAT 27 genes | Jackknifing Library Prep: TruSeq Refined subset of Standard DEX TREAT 30 genes | Standard DEX TREAT Library Prep: Nextera Flex for Enrichment Broadest DEX list for Nextera 26 genes | Jackknifing Library Prep: Nextera Flex for Enrichment Refined subset of Standard DEX TREAT for Nextera 22 genes | Adaboost General Library Prep: TruSeq Broadest adaboost 75 genes | Adaboost Refined TruSeq Library Prep: TruSeq Imrpoved model building for Adaboost, to improve unverisal signal 11 genes | Adaboost Refined Nextera Flex Library Prep: Nextera Flex for Enrichment Imrpoved model building for Adaboost, to improve unverisal signal 24 genes |
| ANO1 | | | | | | | |
| CA3 | | | | | | | |
| C14orf37 | | | | | | | |
| TEAD4 | | | | | | | |
| TAT | | | | | | | |
| LEAP2 | | | | | | | |
| HAO2 | | | | | | | |
| SEMA3G | | | | | | | |
| ADAMTS1 | | | | | | | |
| APOLD1 | | | | | | | |
| IGFBP5 | | | | | | | |
| HSPA12B | | | | | | | |
| GATA5 | | | | | | | |
| SLC9A3R2 | | | | | | | |
| RSPO3 | | | | | | | |
| AQP7P1 | | | | | | | |
| PRX | | | | | | | |
| PNMT | | | | | | | |
| MYOM3 | | | | | | | |
| HRG | | | | | | | |
| TIMP3 | | | | | | | |
| ARHGEF25 | | | | | | | |
| HTRA4 | | | | | | | |
| SCN5A | | | | | | | |
| OLAH | | | | | | | |
| NES | | | | | | | |
| TIMP4 | | | | | | | |
| PAPPA2 | | | | | | | |
| AZGP1 | | | | | | | |
| FAM107A | | | | | | | |
| PRG2 | | | | | | | |
| AMPH | | | | | | | |
| AP3B2 | | | | | | | |
| KRT17 | | | | | | | |
| DAAM2 | | | | | | | |
| LCN6 | | | | | | | |
| ALOX15B | | | | | | | |
| CRH | | | | | | | |
| VSIG4 | | | | | | | |
| LEP | | | | | | | |
| ADAMTS2 | | | | | | | |
| ARMS2 | | | | | | | |

TABLE 2

DEX Analysis

| | | TruSeq ||||| Nextera Flex for enrichment |||
|---|---|---|---|---|---|---|---|---|---|
| | | Standard |||| | | | |
| Gene | Importance Ranking | DEX TREAT | Fold Change | Bootstrapping | Jackknifing | Standard DEX | Fold Change | Jackknifing |
| ADAMTS1 | 1 | Y | 1.79 | Y | Y | Y | +3.2 | Y |
| ADAMTS2 | 1 | Y | 3.61 | Y | Y | Y | +12.2 | Y |
| ALOX15B | 1 | Y | 2.51 | Y | Y | Y | +5.3 | Y |
| ARHGEF25 | 1 | Y | 2.02 | Y | Y | Y | +3.8 | Y |
| DAAM2 | 1 | Y | 2.48 | Y | Y | Y | +5.4 | Y |

TABLE 2-continued

DEX Analysis

| | | TruSeq | | | | | | |
|---|---|---|---|---|---|---|---|---|
| | | Standard | | | | Nextera Flex for enrichment | | |
| Gene | Importance Ranking | DEX TREAT | Fold Change | Bootstrapping | Jackknifing | Standard DEX | Fold Change | Jackknifing |
| FAM107A | 1 | Y | 2.31 | Y | Y | Y | +4.3 | Y |
| HTRA4 | 1 | Y | 2.03 | Y | Y | Y | +4.0 | Y |
| IGFBP5 | 1 | Y | 1.81 | Y | Y | Y | +3.4 | Y |
| KRT5 | 1 | Y | −2.52 | Y | Y | Y | −4.8 | Y |
| LEP | 1 | Y | 3.48 | Y | Y | Y | +8.1 | Y |
| NES | 1 | Y | 2.15 | Y | Y | Y | +4.2 | Y |
| PRX | 1 | Y | 1.93 | Y | Y | Y | +3.3 | Y |
| SEMA3G | 1 | Y | 1.78 | Y | Y | Y | +3.5 | Y |
| SLC9A3R2 | 1 | Y | 1.85 | Y | Y | Y | +3.4 | Y |
| TIMP3 | 1 | Y | 2.01 | Y | Y | Y | +3.7 | Y |
| VSIG4 | 1 | Y | 3.03 | Y | Y | Y | +8.2 | Y |
| PAPPA2 | 2 | Y | 2.20 | Y | Y | Y | +4.2 | N |
| AMPH | 2 | Y | 2.37 | Y | Y | Y | +4.1 | N |
| HSPA12B | 2 | Y | 1.82 | Y | Y | Y | +3.2 | N |
| PTGDR2 | 2 | Y | −1.67 | N | N | Y | −3.5 | Y |
| LCN6 | 2 | Y | 2.49 | Y | N | Y | +4.4 | Y |
| OLAH | 2 | Y | 2.07 | N | N | Y | +5.2 | Y |
| APOLD1 | 3 | Y | 1.80 | N | Y | N | NA | N |
| CUX2 | 3 | Y | −1.73 | N | Y | N | NA | N |
| PITPNM3 | 3 | Y | 1.66 | N | Y | N | NA | N |
| PLD4 | 3 | Y | −1.59 | N | Y | N | NA | N |
| PNMT | 3 | Y | 1.98 | N | Y | N | NA | N |
| CLEC4C | 3 | Y | −1.86 | Y | Y | N | NA | N |
| CRH | 3 | Y | 2.54 | Y | Y | N | NA | N |
| PRG2 | 3 | Y | 2.36 | Y | Y | N | NA | N |
| TEAD4 | 3 | Y | 1.74 | Y | Y | N | NA | N |
| TIMP4 | 3 | Y | 2.17 | Y | Y | N | NA | N |
| CELF4 | 3 | N | NA | N | N | Y | +5.3 | Y |
| KCNA5 | 3 | N | NA | N | N | Y | −4.0 | Y |
| LRRC26 | 3 | N | NA | N | N | Y | −4.4 | Y |
| ARMS2 | 4 | Y | 4.43 | Y | N | N | NA | N |
| FLG | 4 | Y | −3.05 | Y | N | N | NA | N |
| PACSIN1 | 4 | Y | −1.70 | N | N | Y | −3.4 | N |
| A1CF | 5 | Y | 1.37 | N | N | N | NA | N |
| ADCY1 | 5 | Y | 1.62 | N | N | N | NA | N |
| ADRA2C | 5 | Y | 1.69 | N | N | N | NA | N |
| AIF1L | 5 | Y | 1.48 | N | N | N | NA | N |
| ALPK3 | 5 | Y | 1.35 | N | N | N | NA | N |
| ANO1 | 5 | Y | 1.69 | N | N | N | NA | N |
| AP3B2 | 5 | Y | 2.40 | N | N | N | NA | N |
| AQP7 | 5 | Y | 1.51 | N | N | N | NA | N |
| AQP7P1 | 5 | Y | 1.88 | N | N | N | NA | N |
| ARHGEF15 | 5 | Y | 1.33 | N | N | N | NA | N |
| AZGP1 | 5 | Y | 2.27 | N | N | N | NA | N |
| BCL6B | 5 | Y | 1.50 | N | N | N | NA | N |
| BPIFB3 | 5 | Y | −1.80 | N | N | N | NA | N |
| C14orf37 | 5 | Y | 1.73 | N | N | N | NA | N |
| C6 | 5 | Y | 1.33 | N | N | N | NA | N |
| C8B | 5 | Y | 1.49 | N | N | N | NA | N |
| CA3 | 5 | Y | 1.72 | N | N | N | NA | N |
| CACNA1C | 5 | Y | 1.42 | N | N | N | NA | N |
| CADM2 | 5 | Y | −1.76 | N | N | N | NA | N |
| CD34 | 5 | Y | 1.37 | N | N | N | NA | N |
| CLIC5 | 5 | Y | 1.41 | N | N | N | NA | N |
| CPB2 | 5 | Y | 1.69 | N | N | N | NA | N |
| CYP26B1 | 5 | Y | 1.48 | N | N | N | NA | N |
| EMP1 | 5 | Y | 1.30 | N | N | N | NA | N |
| ERG | 5 | Y | 1.43 | N | N | N | NA | N |
| ERRFI1 | 5 | Y | 1.54 | N | N | N | NA | N |
| FAM219A | 5 | Y | 1.24 | N | N | N | NA | N |
| FKBP5 | 5 | Y | 1.50 | N | N | N | NA | N |
| FLNC | 5 | Y | 1.40 | N | N | N | NA | N |
| FMO3 | 5 | Y | 1.39 | N | N | N | NA | N |
| FN1 | 5 | Y | 1.51 | N | N | N | NA | N |
| FSTL3 | 5 | Y | 1.38 | N | N | N | NA | N |
| GATA5 | 5 | Y | 1.82 | N | N | N | NA | N |
| GJA5 | 5 | Y | 1.55 | N | N | N | NA | N |
| GPR116 | 5 | Y | 1.56 | N | N | N | NA | N |
| GPR4 | 5 | Y | 1.65 | N | N | N | NA | N |
| H19 | 5 | Y | 1.32 | N | N | N | NA | N |
| HAO2 | 5 | Y | 1.75 | N | N | N | NA | N |

TABLE 2-continued

DEX Analysis

| | | TruSeq Standard | | | | Nextera Flex for enrichment | | |
|---|---|---|---|---|---|---|---|---|
| Gene | Importance Ranking | DEX TREAT | Fold Change | Bootstrapping | Jackknifing | Standard DEX | Fold Change | Jackknifing |
| HBG2 | 5 | Y | −2.15 | N | N | N | NA | N |
| HRG | 5 | Y | 1.99 | N | N | N | NA | N |
| HTRA1 | 5 | Y | 1.29 | N | N | N | NA | N |
| IGIP | 5 | Y | 1.32 | N | N | N | NA | N |
| IL1R2 | 5 | Y | 1.53 | N | N | N | NA | N |
| IRF6 | 5 | Y | 1.34 | N | N | N | NA | N |
| JAG2 | 5 | Y | 1.57 | N | N | N | NA | N |
| KIF1C | 5 | Y | 1.41 | N | N | N | NA | N |
| KIF26A | 5 | Y | 1.49 | N | N | N | NA | N |
| KRT17 | 5 | Y | 2.47 | N | N | N | NA | N |
| LAMP5 | 5 | Y | −1.77 | N | N | N | NA | N |
| LEAP2 | 5 | Y | 1.74 | N | N | N | NA | N |
| MN1 | 5 | Y | 1.37 | N | N | N | NA | N |
| MYH14 | 5 | Y | 1.38 | N | N | N | NA | N |
| MYL2 | 5 | Y | 1.60 | N | N | N | NA | N |
| MYOM3 | 5 | Y | 1.99 | N | N | N | NA | N |
| NFE2L1 | 5 | Y | 1.26 | N | N | N | NA | N |
| NOMO1 | 5 | Y | −1.49 | N | N | N | NA | N |
| NPR1 | 5 | Y | 1.34 | N | N | N | NA | N |
| NRG3 | 5 | Y | 1.62 | N | N | N | NA | N |
| NTRK2 | 5 | Y | 1.45 | N | N | N | NA | N |
| NXF3 | 5 | Y | −1.96 | N | N | N | NA | N |
| PODXL | 5 | Y | 1.27 | N | N | N | NA | N |
| PPP1R3C | 5 | Y | 1.25 | N | N | N | NA | N |
| PRDM16 | 5 | Y | 1.38 | N | N | N | NA | N |
| PTPN21 | 5 | Y | 1.44 | N | N | N | NA | N |
| RP1L1 | 5 | Y | 1.36 | N | N | N | NA | N |
| RSPO3 | 5 | Y | 1.87 | N | N | N | NA | N |
| SAMD4A | 5 | Y | 1.35 | N | N | N | NA | N |
| SCN5A | 5 | Y | 2.03 | N | N | N | NA | N |
| SERPINA3 | 5 | Y | 1.67 | N | N | N | NA | N |
| SH3PXD2A | 5 | Y | 1.23 | N | N | N | NA | N |
| SH3RF2 | 5 | Y | 1.18 | N | N | N | NA | N |
| SOX17 | 5 | Y | 1.40 | N | N | N | NA | N |
| SRPX | 5 | Y | 1.55 | N | N | N | NA | N |
| SSUH2 | 5 | Y | 1.33 | N | N | N | NA | N |
| STAG3 | 5 | Y | 1.36 | N | N | N | NA | N |
| SULT2A1 | 5 | Y | 1.23 | N | N | N | NA | N |
| SYNPO | 5 | Y | 1.42 | N | N | N | NA | N |
| TAT | 5 | Y | 1.74 | N | N | N | NA | N |
| TEK | 5 | Y | 1.39 | N | N | N | NA | N |
| TENC1 | 5 | Y | 1.38 | N | N | N | NA | N |
| TMC7 | 5 | Y | 1.40 | N | N | N | NA | N |
| UACA | 5 | Y | 1.39 | N | N | N | NA | N |
| WWTR1 | 5 | Y | 1.47 | N | N | N | NA | N |
| ZBTB16 | 5 | Y | 1.50 | N | N | N | NA | N |
| ZCCHC24 | 5 | Y | 1.35 | N | N | N | NA | N |
| ZEB1 | 5 | Y | 1.48 | N | Y | N | NA | N |
| ZNF366 | 5 | Y | 1.23 | N | N | N | NA | N |

TABLE 3

Adaboost Analysis

| | Importance Ranking | Fold Change in Preeclampsia | | Frequency Used By Adaboost | | Average AdaBoost Model Importance | |
|---|---|---|---|---|---|---|---|
| | | TruSeq | Nextera Flex | TruSeq | Nextera Flex | TruSeq | Nextera Flex |
| ADAMTS2 | 1 | +11.6 | +12.2 | 100% | 100% | 9% | 8% |
| ARHGEF25 | 1 | +4.1 | +3.8 | 100% | 100% | 11% | 5% |
| CRH | 1 | +5.7 | +3.9 | 14% | 100% | 2% | 4% |
| LEP | 1 | +10.7 | +8.1 | 100% | 100% | 8% | 17% |
| NES | 1 | +4.5 | +4.2 | 7% | 100% | 4% | 4% |
| PAPPA2 | 1 | +4.9 | +4.2 | 64% | 100% | 3% | 8% |
| SKIL | 1 | +1.5 | +1.4 | 86% | 78% | 3% | 3% |
| ACY3 | 2 | ND | −2.3 | ND | 100% | ND | 3% |
| ADA | 2 | ND | −1.6 | ND | 100% | ND | 5% |

TABLE 3-continued

Adaboost Analysis

| | Importance Ranking | Fold Change in Preeclampsia | | Frequency Used By Adaboost | | Average AdaBoost Model Importance | |
|---|---|---|---|---|---|---|---|
| | | TruSeq | Nextera Flex | TruSeq | Nextera Flex | TruSeq | Nextera Flex |
| ARRDC2 | 2 | +1.8 | ND | 93% | ND | 3% | ND |
| ATP13A3 | 2 | ND | +1.5 | ND | 100% | ND | 5% |
| CLEC4C | 2 | −3.6 | ND | 100% | ND | 18% | ND |
| HTRA4 | 2 | ND | +4.0 | ND | 100% | ND | 5% |
| KCNA5 | 2 | ND | −4.0 | ND | 100% | ND | 8% |
| MYOM3 | 2 | ND | +4.2 | ND | 100% | ND | 7% |
| NOX4 | 2 | ND | −1.8 | ND | 100% | ND | 2% |
| PACSIN1 | 2 | ND | −3.4 | ND | 100% | ND | 2% |
| PLD4 | 2 | ND | −2.7 | ND | 100% | ND | 3% |
| SCT | 2 | ND | −3.3 | ND | 100% | ND | 3% |
| SERPINF1 | 2 | ND | −1.6 | ND | 100% | ND | 2% |
| VSIG4 | 3 | +8.1 | ND | 43% | ND | 3% | ND |
| ARRDC4 | 3 | +2.0 | ND | 36% | ND | 4% | ND |
| LILRA4 | 3 | ND | −2.7 | ND | 33% | ND | 1% |
| LRRC26 | 3 | ND | −4.4 | ND | 56% | ND | 2% |
| PER1 | 3 | ND | +2.2 | ND | 33% | ND | 1% |
| PHEX | 3 | ND | −2.2 | ND | 56% | ND | 2% |
| SEMA3G | 3 | ND | +3.5 | ND | 67% | ND | 5% |
| TIPARP | 3 | ND | +1.2 | ND | 67% | ND | 2% |
| ADAM17 | 4 | ND | ND | ND | ND | ND | ND |
| ARFGAP3 | 4 | ND | ND | ND | ND | ND | ND |
| ARRDC3 | 4 | ND | ND | ND | ND | ND | ND |
| ASTE1 | 4 | ND | ND | ND | ND | ND | ND |
| ATOH8 | 4 | ND | ND | ND | ND | ND | ND |
| C10orf2 | 4 | ND | ND | ND | ND | ND | ND |
| C22orf39 | 4 | ND | ND | ND | ND | ND | ND |
| CCDC151 | 4 | ND | ND | ND | ND | ND | ND |
| CD63 | 4 | ND | ND | ND | ND | ND | ND |
| CKAP4 | 4 | ND | ND | ND | ND | ND | ND |
| CLCN1 | 4 | ND | ND | ND | ND | ND | ND |
| CLEC4M | 4 | ND | ND | ND | ND | ND | ND |
| CLIC5 | 4 | ND | ND | ND | ND | ND | ND |
| CNFN | 4 | ND | ND | ND | ND | ND | ND |
| CPAMD8 | 4 | ND | ND | ND | ND | ND | ND |
| CUX2 | 4 | ND | ND | ND | ND | ND | ND |
| DDI2 | 4 | ND | ND | ND | ND | ND | ND |
| EBI3 | 4 | ND | ND | ND | ND | ND | ND |
| ELMO3 | 4 | ND | ND | ND | ND | ND | ND |
| ENC1 | 4 | ND | ND | ND | ND | ND | ND |
| ETV3 | 4 | ND | ND | ND | ND | ND | ND |
| FAR2 | 4 | ND | ND | ND | ND | ND | ND |
| FOS | 4 | ND | ND | ND | ND | ND | ND |
| FSTL3 | 4 | ND | ND | ND | ND | ND | ND |
| GATSL2 | 4 | ND | ND | ND | ND | ND | ND |
| GBP2 | 4 | ND | ND | ND | ND | ND | ND |
| GINS4 | 4 | ND | ND | ND | ND | ND | ND |
| GSTA3 | 4 | ND | ND | ND | ND | ND | ND |
| HEATR9 | 4 | ND | ND | ND | ND | ND | ND |
| HEG1 | 4 | ND | ND | ND | ND | ND | ND |
| HIPK2 | 4 | ND | ND | ND | ND | ND | ND |
| JUN | 4 | ND | ND | ND | ND | ND | ND |
| MRPS35 | 4 | ND | ND | ND | ND | ND | ND |
| MTRNR2L6 | 4 | ND | ND | ND | ND | ND | ND |
| ORAI3 | 4 | ND | ND | ND | ND | ND | ND |
| PARN | 4 | ND | ND | ND | ND | ND | ND |
| PDE8B | 4 | ND | ND | ND | ND | ND | ND |
| PI4KAP1 | 4 | ND | ND | ND | ND | ND | ND |
| PPP1R17 | 4 | ND | ND | ND | ND | ND | ND |
| PRG2 | 4 | ND | ND | ND | ND | ND | ND |
| PSMD11 | 4 | ND | ND | ND | ND | ND | ND |
| RGP1 | 4 | ND | ND | ND | ND | ND | ND |
| RNF6 | 4 | ND | ND | ND | ND | ND | ND |
| SCAMP1 | 4 | ND | ND | ND | ND | ND | ND |
| SLC26A2 | 4 | ND | ND | ND | ND | ND | ND |
| SLC4A3 | 4 | ND | ND | ND | ND | ND | ND |
| SLIT3 | 4 | ND | ND | ND | ND | ND | ND |
| SMPD3 | 4 | ND | ND | ND | ND | ND | ND |
| SPDYE5 | 4 | ND | ND | ND | ND | ND | ND |
| ST6GALNAC3 | 4 | ND | ND | ND | ND | ND | ND |
| THTPA | 4 | ND | ND | ND | ND | ND | ND |
| TMEM108 | 4 | ND | ND | ND | ND | ND | ND |
| TMEM11 | 4 | ND | ND | ND | ND | ND | ND |
| TNFRSF21 | 4 | ND | ND | ND | ND | ND | ND |

TABLE 3-continued

Adaboost Analysis

| | Importance Ranking | Fold Change in Preeclampsia | | Frequency Used By Adaboost | | Average AdaBoost Model Importance | |
|---|---|---|---|---|---|---|---|
| | | TruSeq | Nextera Flex | TruSeq | Nextera Flex | TruSeq | Nextera Flex |
| TPCN1 | 4 | ND | ND | ND | ND | ND | ND |
| TPST1 | 4 | ND | ND | ND | ND | ND | ND |
| TRAF3IP1 | 4 | ND | ND | ND | ND | ND | ND |
| TRUB1 | 4 | ND | ND | ND | ND | ND | ND |
| TTC21A | 4 | ND | ND | ND | ND | ND | ND |
| USP54 | 4 | ND | ND | ND | ND | ND | ND |
| ZMYM6 | 4 | ND | ND | ND | ND | ND | ND |

TABLE 4

Gene Glossary

| Gene Symbol Used in Patent | Official Gene Symbol | Approved Name | HGNC ID | Location |
|---|---|---|---|---|
| KRT5 | KRT5 | keratin 5 | HGNC:6442 | 12q13.13 |
| CUX2 | CUX2 | cut like homeobox 2 | HGNC:19347 | 12q24.11-q24.12 |
| CLEC4C | CLEC4C | C-type lectin domain family 4 member C | HGNC:13258 | 12p13.31 |
| PLD4 | PLD4 | phospholipase D family member 4 | HGNC:23792 | 14q32.33 |
| ALOX15B | ALOX15B | arachidonate 15-lipoxygenase type B | HGNC:434 | 17p13.1 |
| PRG2 | PRG2 | proteoglycan 2, pro eosinophil major basic protein | HGNC:9362 | 11q12.1 |
| HTRA4 | HTRA4 | HtrA serine peptidase 4 | HGNC:26909 | 8p11.22 |
| AMPH | AMPH | amphiphysin | HGNC:471 | 7p14.1 |
| PNMT | PNMT | phenylethanolamine N-methyltransferase | HGNC:9160 | 17q12 |
| LEP | LEP | leptin | HGNC:6553 | 7q32.1 |
| PAPPA2 | PAPPA2 | pappalysin 2 | HGNC:14615 | 1q25.2 |
| CRH | CRH | corticotropin releasing hormone | HGNC:2355 | 8q13.1 |
| TIMP4 | TIMP4 | TIMP metallopeptidase inhibitor 4 | HGNC:11823 | 3p25.2 |
| APOLD1 | APOLD1 | apolipoprotein L domain containing 1 | HGNC:25268 | 12p13.1 |
| ARHGEF25 | ARHGEF25 | Rho guanine nucleotide exchange factor 25 | HGNC:30275 | 12q13.3 |
| TIMP3 | TIMP3 | TIMP metallopeptidase inhibitor 3 | HGNC:11822 | 22q12.3 |
| SEMA3G | SEMA3G | semaphorin 3G | HGNC:30400 | 3p21.1 |
| IGFBP5 | IGFBP5 | insulin like growth factor binding protein 5 | HGNC:5474 | 2q35 |
| PRX | PRX | periaxin | HGNC:13797 | 19q13.2 |
| PITPNM3 | PITPNM3 | PITPNM family member 3 | HGNC:21043 | 17p13.2-p13.1 |
| FAM107A | FAM107A | family with sequence similarity 107 member A | HGNC:30827 | 3p14.3-p14.2 |
| TEAD4 | TEAD4 | TEA domain transcription factor 4 | HGNC:11717 | 12p13.33 |
| HSPA12B | HSPA12B | heat shock protein family A (Hsp70) member 12B | HGNC:16193 | 20p13 |
| NES | NES | nestin | HGNC:7756 | 1q23.1 |
| SLC9A3R2 | SLC9A3R2 | SLC9A3 regulator 2 | HGNC:11076 | 16p13.3 |
| ZEB1 | ZEB1 | zinc finger E-box binding homeobox 1 | HGNC:11642 | 10p11.22 |
| ADAMTS1 | ADAMTS1 | ADAM metallopeptidase with thrombospondin type 1 motif 1 | HGNC:217 | 21q21.3 |
| DAAM2 | DAAM2 | dishevelled associated activator of morphogenesis 2 | HGNC:18143 | 6p21.2 |
| ADAMTS2 | ADAMTS2 | ADAM metallopeptidase with thrombospondin type 1 motif 2 | HGNC:218 | 5q35.3 |
| VSIG4 | VSIG4 | V-set and immunoglobulin domain containing 4 | HGNC:17032 | Xq12 |
| ARRDC2 | ARRDC2 | arrestin domain containing 2 | HGNC:25225 | 19p13.11 |
| SKIL | SKIL | SKI like proto-oncogene | HGNC:10897 | 3q26.2 |
| ARRDC4 | ARRDC4 | arrestin domain containing 4 | HGNC:28087 | 15q26.2 |
| KCNA5 | KCNA5 | potassium voltage-gated channel subfamily A member 5 | HGNC:6224 | 12p13.32 |
| MYOM3 | MYOM3 | myomesin 3 | HGNC:26679 | 1p36.11 |
| ATP13A3 | ATP13A3 | ATPase 13A3 | HGNC:24113 | 3q29 |
| ADA | ADA | adenosine deaminase | HGNC:186 | 20q13.12 |
| ACY3 | ACY3 | aminoacylase 3 | HGNC:24104 | 11q13.2 |
| SCT | SCT | secretin | HGNC:10607 | 11p15.5 |
| NOX4 | NOX4 | NADPH oxidase 4 | HGNC:7891 | 11q14.3 |
| PACSIN1 | PACSIN1 | protein kinase C and casein kinase substrate in neurons 1 | HGNC:8570 | 6p21.3 |
| SERPINF1 | SERPINF1 | serpin family F member 1 | HGNC:8824 | 17p13.3 |
| TIPARP | TIPARP | TCDD inducible poly(ADP-ribose) polymerase | HGNC:23696 | 3q25.31 |
| LRRC26 | LRRC26 | leucine rich repeat containing 26 | HGNC:31409 | 9q34.3 |
| PHEX | PHEX | phosphate regulating endopeptidase homolog X-linked | HGNC:8918 | Xp22.11 |
| LILRA4 | LILRA4 | leukocyte immunoglobulin like receptor A4 | HGNC:15503 | 19q13.42 |
| PER1 | PER1 | period circadian regulator 1 | HGNC:8845 | 17p13.1 |
| CELF4 | CELF4 | CUGBP Elav-like family member 4 | HGNC:14015 | 18q12.2 |
| LCN6 | LCN6 | lipocalin 6 | HGNC:17337 | 9q34.3 |
| OLAH | OLAH | oleoyl-ACP hydrolase | HGNC:25625 | 10p13 |
| PTGDR2 | PTGDR2 | prostaglandin D2 receptor 2 | HGNC:4502 | 11q12.2 |
| JUN | JUN | Jun proto-oncogene, AP-1 transcription factor subunit | HGNC:6204 | 1p32.1 |
| PDE8B | PDE8B | phosphodiesterase 8B | HGNC:8794 | 5q13.3 |
| GSTA3 | GSTA3 | glutathione S-transferase alpha 3 | HGNC:4628 | 6p12.2 |
| RGP1 | RGP1 | RGP1 homolog, RAB6A GEF complex partner 1 | HGNC:21965 | 9p13.3 |

TABLE 4-continued

Gene Glossary

| Gene Symbol Used in Patent | Official Gene Symbol | Approved Name | HGNC ID | Location |
|---|---|---|---|---|
| USP54 | USP54 | ubiquitin specific peptidase 54 | HGNC:23513 | 10q22.2 |
| MRPS35 | MRPS35 | mitochondrial ribosomal protein S35 | HGNC:16635 | 12p11.22 |
| HEATR9 | HEATR9 | HEAT repeat containing 9 | HGNC:26548 | 17q12 |
| FSTL3 | FSTL3 | follistatin like 3 | HGNC:3973 | 19p13.3 |
| DDI2 | DDI2 | DNA damage inducible 1 homolog 2 | HGNC:24578 | 1p36.21 |
| ZMYM6 | ZMYM6 | zinc finger MYM-type containing 6 | HGNC:13050 | 1p34.3 |
| ST6GALNAC3 | ST6GALNAC3 | ST6 N-acetylgalactosaminide alpha-2,6-sialyltransferase 3 | HGNC:19343 | 1p31.1 |
| GBP2 | GBP2 | guanylate binding protein 2 | HGNC:4183 | 1p22.2 |
| ETV3 | ETV3 | ETS variant 3 | HGNC:3492 | 1q23.1 |
| ADAM17 | ADAM17 | ADAM metallopeptidase domain 17 | HGNC:195 | 2p25.1 |
| ATOH8 | ATOH8 | atonal bHLH transcription factor 8 | HGNC:24126 | 2p11.2 |
| SLC4A3 | SLC4A3 | solute carrier family 4 member 3 | HGNC:11029 | 2q35 |
| TRAF3IP1 | TRAF3IP1 | TRAF3 interacting protein 1 | HGNC:17861 | 2q37.3 |
| TTC21A | TTC21A | tetratricopeptide repeat domain 21A | HGNC:30761 | 3p22.2 |
| HEG1 | HEG1 | heart development protein with EGF like domains 1 | HGNC:29227 | 3q21.2 |
| ASTE1 | ASTE1 | asteroid homolog 1 | HGNC:25021 | 3q22.1 |
| TMEM108 | TMEM108 | transmembrane protein 108 | HGNC:28451 | 3q22.1 |
| ENC1 | ENC1 | ectodermal-neural cortex 1 | HGNC:3345 | 5q13.3 |
| SCAMP1 | SCAMP1 | secretory carrier membrane protein 1 | HGNC:10563 | 5q14.1 |
| ARRDC3 | ARRDC3 | arrestin domain containing 3 | HGNC:29263 | 5q14.3 |
| SLC26A2 | SLC26A2 | solute carrier family 26 member 2 | HGNC:10994 | 5q32 |
| SLIT3 | SLIT3 | slit guidance ligand 3 | HGNC:11087 | 5q34-q35.1 |
| CLIC5 | CLIC5 | chloride intracellular channel 5 | HGNC:13517 | 6p21.1 |
| TNFRSF21 | TNFRSF21 | TNF receptor superfamily member 21 | HGNC:13469 | 6p12.3 |
| PPP1R17 | PPP1R17 | protein phosphatase 1 regulatory subunit 17 | HGNC:16973 | 7p14.3 |
| TPST1 | TPST1 | tyrosylprotein sulfotransferase 1 | HGNC:12020 | 7q11.21 |
| GATSL2 | CASTOR2 | cytosolic arginine sensor for mTORC1 subunit 2 | HGNC:37073 | 7q11.23 |
| SPDYE5 | SPDYE5 | speedy/RINGO cell cycle regulator family member E5 | HGNC:35464 | 7q11.23 |
| HIPK2 | HIPK2 | homeodomain interacting protein kinase 2 | HGNC:14402 | 7q34 |
| MTRNR2L6 | MTRNR2L6 | MT-RNR2 like 6 | HGNC:37163 | 7q34 |
| CLCN1 | CLCN1 | chloride voltage-gated channel 1 | HGNC:2019 | 7q34 |
| GINS4 | GINS4 | GINS complex subunit 4 | HGNC:28226 | 8p11.21 |
| C10orf2 | TWNK | twinkle mtDNA helicase | HGNC:1160 | 10q24.31 |
| TRUB1 | TRUB1 | TruB pseudouridine synthase family member 1 | HGNC:16060 | 10q25.3 |
| FAR2 | FAR2 | fatty acyl-CoA reductase 2 | HGNC:25531 | 12p11.22 |
| CD63 | CD63 | CD63 molecule | HGNC:1692 | 12q13.2 |
| CKAP4 | CKAP4 | cytoskeleton associated protein 4 | HGNC:16991 | 12q23.3 |
| TPCN1 | TPCN1 | two pore segment channel 1 | HGNC:18182 | 12q24.13 |
| RNF6 | RNF6 | ring finger protein 6 | HGNC:10069 | 13q12.13 |
| THTPA | THTPA | thiamine triphosphatase | HGNC:18987 | 14q11.2 |
| FOS | FOS | Fos proto-oncogene, AP-1 transcription factor subunit | HGNC:3796 | 14q24.3 |
| PARN | PARN | poly(A)-specific ribonuclease | HGNC:8609 | 16p13.12 |
| ORAI3 | ORAI3 | ORAI calcium release-activated calcium modulator 3 | HGNC:28185 | 16p11.2 |
| ELMO3 | ELMO3 | engulfment and cell motility 3 | HGNC:17289 | 16q22.1 |
| SMPD3 | SMPD3 | sphingomyelin phosphodiesterase 3 | HGNC:14240 | 16q22.1 |
| TMEM11 | TMEM11 | transmembrane protein 11 | HGNC:16823 | 17p11.1 |
| PSMD11 | PSMD11 | proteasome 26S subunit, non-ATPase 11 | HGNC:9556 | 17q11.2 |
| EBI3 | EBI3 | Epstein-Barr virus induced 3 | HGNC:3129 | 19p13.3 |
| CLEC4M | CLEC4M | C-type lectin domain family 4 member M | HGNC:13523 | 19p13.2 |
| CCDC151 | CCDC151 | coiled-coil domain containing 151 | HGNC:28303 | 19p13.2 |
| CPAMD8 | CPAMD8 | C3 and PZP like alpha-2-macroglobulin domain containing 8 | HGNC:23228 | 19p13.11 |
| CNFN | CNFN | cornifelin | HGNC:30183 | 19q13.2 |
| C22orf39 | C22orf39 | chromosome 22 open reading frame 39 | HGNC:27012 | 22q11.21 |
| PI4KAP1 | PI4KAP1 | phosphatidylinositol 4-kinase alpha pseudogene 1 | HGNC:33576 | 22q11.21 |
| ARFGAP3 | ARFGAP3 | ADP ribosylation factor GTPase activating protein 3 | HGNC:661 | 22q13.2 |
| FLG | FLG | filaggrin | HGNC:3748 | 1q21.3 |
| ARMS2 | ARMS2 | age-related maculopathy susceptibility 2 | HGNC:32685 | 10q26.13 |
| CYP26B1 | CYP26B1 | cytochrome P450 family 26 subfamily B member 1 | HGNC:20581 | 2p13.2 |
| IRF6 | IRF6 | interferon regulatory factor 6 | HGNC:6121 | 1q32.2 |
| MYH14 | MYH14 | myosin heavy chain 14 | HGNC:23212 | 19q13.33 |
| PODXL | PODXL | podocalyxin like | HGNC:9171 | 7q32.3 |
| PPP1R3C | PPP1R3C | protein phosphatase 1 regulatory subunit 3C | HGNC:9293 | 10q23.32 |
| SH3RF2 | SH3RF2 | SH3 domain containing ring finger 2 | HGNC:26299 | 5q32 |
| TMC7 | TMC7 | transmembrane channel like 7 | HGNC:23000 | 16p12.3 |
| ZNF366 | ZNF366 | zinc finger protein 366 | HGNC:18316 | 5q13.1 |
| ADCY1 | ADCY1 | adenylate cyclase 1 | HGNC:232 | 7p12.3 |
| C6 | C6 | complement C6 | HGNC:1339 | 5p13.1 |
| FAM219A | FAM219A | family with sequence similarity 219 member A | HGNC:19920 | 9p13.3 |
| HAO2 | HAO2 | hydroxyacid oxidase 2 | HGNC:4810 | 1p12 |
| IGIP | IGIP | IgA inducing protein | HGNC:33847 | 5q31.3 |
| IL1R2 | IL1R2 | interleukin 1 receptor type 2 | HGNC:5994 | 2q11.2 |
| NTRK2 | NTRK2 | neurotrophic receptor tyrosine kinase 2 | HGNC:8032 | 9q21.33 |
| SH3PXD2A | SH3PXD2A | SH3 and PX domains 2A | HGNC:23664 | 10q24.33 |
| SSUH2 | SSUH2 | ssu-2 homolog | HGNC:24809 | 3p25.3 |
| SULT2A1 | SULT2A1 | sulfotransferase family 2A member 1 | HGNC:11458 | 19q13.33 |

TABLE 4-continued

Gene Glossary

| Gene Symbol Used in Patent | Official Gene Symbol | Approved Name | HGNC ID | Location |
|---|---|---|---|---|
| FMO3 | FMO3 | flavin containing dimethylaniline monoxygenase 3 | HGNC:3771 | 1q24.3 |
| GATA5 | GATA5 | GATA binding protein 5 | HGNC:15802 | 20q13.33 |
| HTRA1 | HTRA1 | HtrA serine peptidase 1 | HGNC:9476 | 10q26.13 |
| C8B | C8B | complement C8 beta chain | HGNC:1353 | 1p32.2 |
| H19 | H19 | H19 imprinted maternally expressed transcript | HGNC:4713 | 11p15.5 |
| MN1 | MN1 | MN1 proto-oncogene, transcriptional regulator | HGNC:7180 | 22q12.1 |
| NFE2L1 | NFE2L1 | nuclear factor, erythroid 2 like 1 | HGNC:7781 | 17q21.3 |
| PRDM16 | PRDM16 | PR/SET domain 16 | HGNC:14000 | 1p36.32 |
| AP3B2 | AP3B2 | adaptor related protein complex 3 subunit beta 2 | HGNC:567 | 15q25.2 |
| EMP1 | EMP1 | epithelial membrane protein 1 | HGNC:3333 | 12p13.1 |
| FLNC | FLNC | filamin C | HGNC:3756 | 7q32.1 |
| STAG3 | STAG3 | stromal antigen 3 | HGNC:11356 | 7q22.1 |
| CPB2 | CPB2 | carboxypeptidase B2 | HGNC:2300 | 13q14.13 |
| TENC1 | TNS2 | tensin 2 | HGNC:19737 | 12q13.13 |
| RP1L1 | RP1L1 | RP1 like 1 | HGNC:15946 | 8p23.1 |
| A1CF | A1CF | APOBEC1 complementation factor | HGNC:24086 | 10q11.23 |
| NPR1 | NPR1 | natriuretic peptide receptor 1 | HGNC:7943 | 1q21.3 |
| TEK | TEK | TEK receptor tyrosine kinase | HGNC:11724 | 9p21.2 |
| ERRFI1 | ERRFI1 | ERBB receptor feedback inhibitor 1 | HGNC:18185 | 1p36.23 |
| ARHGEF15 | ARHGEF15 | Rho guanine nucleotide exchange factor 15 | HGNC:15590 | 17p13.1 |
| CD34 | CD34 | CD34 molecule | HGNC:1662 | 1q32.2 |
| RSPO3 | RSPO3 | R-spondin 3 | HGNC:20866 | 6q22.33 |
| ALPK3 | ALPK3 | alpha kinase 3 | HGNC:17574 | 15q25.3 |
| SAMD4A | SAMD4A | sterile alpha motif domain containing 4A | HGNC:23023 | 14q22.2 |
| ZCCHC24 | ZCCHC24 | zinc finger CCHC-type containing 24 | HGNC:26911 | 10q22.3 |
| LEAP2 | LEAP2 | liver enriched antimicrobial peptide 2 | HGNC:29571 | 5q31.1 |
| MYL2 | MYL2 | myosin light chain 2 | HGNC:7583 | 12q24.11 |
| NRG3 | NRG3 | neuregulin 3 | HGNC:7999 | 10q23.1 |
| ZBTB16 | ZBTB16 | zinc finger and BTB domain containing 16 | HGNC:12930 | 11q23.2 |
| SERPINA3 | SERPINA3 | serpin family A member 3 | HGNC:16 | 14q32.13 |
| AQP7 | AQP7 | aquaporin 7 | HGNC:640 | 9p13.3 |
| SRPX | SRPX | sushi repeat containing protein X-linked | HGNC:11309 | Xp11.4 |
| UACA | UACA | uveal autoantigen with coiled-coil domains and ankyrin repeats | HGNC:15947 | 15q23 |
| ANO1 | ANO1 | anoctamin 1 | HGNC:21625 | 11q13.3 |
| FKBP5 | FKBP5 | FKBP prolyl isomerase 5 | HGNC:3721 | 6p21.31 |
| SCN5A | SCN5A | sodium voltage-gated channel alpha subunit 5 | HGNC:10593 | 3p22.2 |
| PTPN21 | PTPN21 | protein tyrosine phosphatase non-receptor type 21 | HGNC:9651 | 14q31.3 |
| CACNA1C | CACNA1C | calcium voltage-gated channel subunit alpha1 C | HGNC:1390 | 12p13.33 |
| ERG | ERG | ETS transcription factor ERG | HGNC:3446 | 21q22.2 |
| SOX17 | SOX17 | SRY-box 17 | HGNC:18122 | 8q11.23 |
| WWTR1 | WWTR1 | WW domain containing transcription regulator 1 | HGNC:24042 | 3q25.1 |
| AIF1L | AIF1L | allograft inflammatory factor 1 like | HGNC:28904 | 9q34.12-q34.13 |
| CA3 | CA3 | carbonic anhydrase 3 | HGNC:1374 | 8q21.2 |
| HRG | HRG | histidine rich glycoprotein | HGNC:5181 | 3q27.3 |
| TAT | TAT | tyrosine aminotransferase | HGNC:11573 | 16q22.2 |
| AQP7P1 | AQP7P1 | aquaporin 7 pseudogene 1 | HGNC:32048 | 9q13 |
| ADRA2C | ADRA2C | adrenoceptor alpha 2C | HGNC:283 | 4p16.3 |
| SYNPO | SYNPO | synaptopodin | HGNC:30672 | 5q33.1 |
| FN1 | FN1 | fibronectin 1 | HGNC:3778 | 2q35 |
| GPR116 | ADGRF5 | adhesion G protein-coupled receptor F5 | HGNC:19030 | 6p12.3 |
| KRT17 | KRT17 | keratin 17 | HGNC:6427 | 17q21.2 |
| AZGP1 | AZGP1 | alpha-2-glycoprotein 1, zinc-binding | HGNC:910 | 7q22.1 |
| BCL6B | BCL6B | BCL6B transcription repressor | HGNC:1002 | 17p13.1 |
| KIF1C | KIF1C | kinesin family member 1C | HGNC:6317 | 17p13.2 |
| GPR4 | GPR4 | G protein-coupled receptor 4 | HGNC:4497 | 19q13.32 |
| GJA5 | GJA5 | gap junction protein alpha 5 | HGNC:4279 | 1q21.2 |
| C14orf37 | ARMH4 | armadillo like helical domain containing 4 | HGNC:19846 | 14q23.1 |
| JAG2 | JAG2 | jagged canonical Notch ligand 2 | HGNC:6189 | 14q32.33 |
| KIF26A | KIF26A | kinesin family member 26A | HGNC:20226 | 14q32.33 |
| HBG2 | HBG2 | hemoglobin subunit gamma 2 | HGNC:4832 | 11p15.4 |
| CADM2 | CADM2 | cell adhesion molecule 2 | HGNC:29849 | 3p12.1 |
| LAMP5 | LAMP5 | lysosomal associated membrane protein family member 5 | HGNC:16097 | 20p12.2 |
| NOMO1 | NOMO1 | NODAL modulator 1 | HGNC:30060 | 16p13.11 |
| NXF3 | NXF3 | nuclear RNA export factor 3 | HGNC:8073 | Xq22.1 |
| BPIFB3 | BPIFB3 | BPI fold containing family B member 3 | HGNC:16178 | 20q11.21 |
| CGB8 | CGB8 | chorionic gonadotropin subunit beta 8 | HGNC:16453 | 19q13.33 |
| CGB5 | CGB5 | chorionic gonadotropin subunit beta 5 | HGNC:16452 | 19q13.33 |
| ZSCAN23 | ZSCAN23 | zinc finger and SCAN domain containing 23 | HGNC:21193 | 6p22.1 |
| HSPA1A | HSPA1A | heat shock protein family A (Hsp70) member 1A | HGNC:5232 | 6p21.33 |
| PMAIP1 | PMAIP1 | phorbol-12-myristate-13-acetate-induced protein 1 | HGNC:9108 | 18q21.32 |
| C8orf4 | TCIM | transcriptional and immune response regulator | HGNC:1357 | 8p11.21 |
| ITM2B | ITM2B | integral membrane protein 2B | HGNC:6174 | 13q14.2 |
| IFIT2 | IFIT2 | interferon induced protein with tetratricopeptide repeats 2 | HGNC:5409 | 10q23.31 |
| CD74 | CD74 | CD74 molecule | HGNC:1697 | 5q33.1 |
| HSPA6 | HSPA6 | heat shock protein family A (Hsp70) member 6 | HGNC:5239 | 1q23.3 |

TABLE 4-continued

Gene Glossary

| Gene Symbol Used in Patent | Official Gene Symbol | Approved Name | HGNC ID | Location |
|---|---|---|---|---|
| TFAP2A | TFAP2A | transcription factor AP-2 alpha | HGNC:11742 | 6p24.3 |
| TRPV6 | TRPV6 | transient receptor potential cation channel subfamily V member 6 | HGNC:14006 | 7q34 |
| EXPH5 | EXPH5 | exophilin 5 | HGNC:30578 | 11q22.3 |
| CAPN6 | CAPN6 | calpain 6 | HGNC:1483 | Xq23 |
| ALDH3B2 | ALDH3B2 | aldehyde dehydrogenase 3 family member B2 | HGNC:411 | 11q13.2 |
| RAB3B | RAB3B | RAB3B, member RAS oncogene family | HGNC:9778 | 1p32.3 |
| MUC15 | MUC15 | mucin 15, cell surface associated | HGNC:14956 | 11p14.3 |
| GRHL2 | GRHL2 | grainyhead like transcription factor 2 | HGNC:2799 | 8q22.3 |
| CSHL1 | CSHL1 | chorionic somatomammotropin hormone like 1 | HGNC:2442 | 17q23.3 |
| CSH2 | CSH2 | chorionic somatomammotropin hormone 2 | HGNC:2441 | 17q23.3 |
| KISS1 | KISS1 | KiSS-1 metastasis suppressor | HGNC:6341 | 1q32.1 |
| CGA | CGA | glycoprotein hormones, alpha polypeptide | HGNC:1885 | 6q14.3 |
| PLAC4 | PLAC4 | placenta enriched 4 | HGNC:14616 | 21q22.2 |
| PSG1 | PSG1 | pregnancy specific beta-1-glycoprotein 1 | HGNC:9514 | 19q13.2 |
| GH2 | GH2 | growth hormone 2 | HGNC:4262 | 17q23.3 |
| PSG3 | PSG3 | pregnancy specific beta-1-glycoprotein 3 | HGNC:9520 | 19q13.2 |
| PSG4 | PSG4 | pregnancy specific beta-1-glycoprotein 4 | HGNC:9521 | 19q13.31 |
| PSG7 | PSG7 | pregnancy specific beta-1-glycoprotein 7 (gene/pseudogene) | HGNC:9524 | 19q13.31 |
| PSG11 | PSG11 | pregnancy specific beta-1-glycoprotein 11 | HGNC:9516 | 19q13.31 |
| CSH1 | CSH1 | chorionic somatomammotropin hormone 1 | HGNC:2440 | 17q23.3 |
| PSG2 | PSG2 | pregnancy specific beta-1-glycoprotein 2 | HGNC:9519 | 19q13.31 |
| HSD3B1 | HSD3B1 | hydroxy-delta-5-steroid dehydrogenase, 3 beta- and steroid delta-isomerase 1 | HGNC:5217 | 1p12 |
| LGALS14 | LGALS14 | galectin 14 | HGNC:30054 | 19q13.2 |
| FCGR1C | FCGR1CP | Fc fragment of IgG receptor Ic, pseudogene | HGNC:3615 | 1q21.1 |
| PSG5 | PSG5 | pregnancy specific beta-l-glycoprotein 5 | HGNC:9522 | 19q13.31 |
| LAGALS13 | LGALS13 | galectin 13 | HGNC:15449 | 19q13.2 |
| GCM1 | GCM1 | glial cells missing transcription factor 1 | HGNC:4197 | 6p12.1 |

The term "plurality" refers to more than one element. For example, the term is used herein in reference to a number of C-RNA molecules that serve as a signature indicative of preeclampsia.

A plurality may include any two, any three, any four, any five, any six, any seven, any eight, any nine, any ten, any eleven, any twelve, any thirteen, any fourteen, any fifteen, any sixteen, any seventeen, any eighteen, any nineteen, any twenty, any twenty-one, any twenty-two, any twenty-three, any twenty-four, any twenty-five, any twenty-six, any twenty-seven, any twenty-eight, any twenty-nine, any thirty, any thirty-one, any thirty-two, any thirty-three, any thirty-four, any thirty-five, any thirty-six, any thirty-seven, any thirty-eight, any thirty-nine, any forty, any forty-one, any forty-two, any forty-three, any forty-four, any forty-five, any forty-six, any forty-seven, any forty-eight, any forty-nine, any fifty, any fifty-one, any fifty-two, any fifty-three, any fifty-four, any fifty-five, any fifty-six, any fifty-seven, any fifty-eight, any fifty-nine, any sixty, any sixty-one, any sixty-two, any sixty-three, any sixty-four, any sixty-five, any sixty-six, any sixty-seven, any sixty-eight, any sixty-nine, any seventy, any seventy-one, any seventy-two, any seventy-three, any seventy-four, any seventy-five, any seventy-six, any seventy-seven, any seventy-eight, any seventy-nine, any eighty, any eighty-one, any eighty-two, any eighty-three, any eighty-four, any eighty-five, any eighty-six, any eighty-seven, any eighty-eight, any eighty-nine, any ninety, any ninety-one, any ninety-two, any ninety-three, any ninety-four, any ninety-five, any ninety-six, any ninety-seven, any ninety-eight, any ninety-nine, any one hundred, any one hundred and one, any one hundred and two, any one hundred and three, any one hundred and four, any one hundred and five, any one hundred and six, any one hundred and seven, any one hundred and eight, any one hundred and nine, any one hundred ten, any one hundred eleven, any one hundred twelve, any one hundred thirteen, any one hundred fourteen, any one hundred fifteen, any one hundred sixteen, any one hundred seventeen, any one hundred eighteen, any one hundred nineteen, any one hundred twenty, any one hundred twenty-one, or any one hundred twenty-two of the molecules recited in a list described herein. A plurality may include a least any of the numbers recited above. A plurality may include more than any of the numbers recited above. A plurality may include a range of any of those recited above. In some embodiments, a C-RNA signature indicative of preeclampsia includes just one of the biomarkers recited above.

The identification and/or quantification of one of these C-RNA signatures within a sample obtained from a subject can be used to determine that the subject suffers from preeclampsia or is at a risk of developing preeclampsia.

A sample may be a biological sample or biosample, including but not limited to blood, serum, plasma, sweat, tears, urine, sputum, lymph, saliva, amniotic fluid, a tissue biopsy, swab, or smear, including for example, but not limited to, a placental tissue sample. In some preferred embodiments, a biological sample is a cell free plasma sample. A biological sample may be a maternal sample obtained from a pregnant female subject.

As used herein, the term "subject" refers to a human subject as well as a non-human mammalian subject. Although the examples herein concern humans and the language is primarily directed to human concerns, the concept of this disclosure is applicable to any mammal, and is useful in the fields of veterinary medicine, animal sciences, research laboratories and such.

A subject may be a pregnant female, including a pregnant female in any gestational stages of pregnancy. The gestational stage of pregnancy may be, for example, the first trimester, the second trimester, including late second trimester, or the third trimester, including early third trimester. The gestational stage of pregnancy may be, for example, before 16 weeks of pregnancy, before 20 weeks of pregnancy, or after 20 weeks of pregnancy. The gestational stage of pregnancy may be, for example, 8-18 weeks of pregnancy, 10-14 weeks of pregnancy, 11-14 weeks of pregnancy, 11-13 weeks, or 12-13 weeks of pregnancy.

The discovery of cell-free fetal nucleic acids in maternal plasma has opened up new possibilities for noninvasive prenatal diagnosis. Over the last few years, a number of approaches have been demonstrated to allow such circulating fetal nucleic acids to be used for the prenatal detection of chromosomal aneuploidies. Any of the methods described for example in Poon et al., 2000, *Clin Chem;* 1832-4; Poon et al., 2001, *Ann N Y Acad Sci;* 945:207-10; Ng et al., 2003, *Clin Chem;* 49(5):727-31; Ng et al., 2003, *Proc Natl Acad Sci USA;*100(8):4748-53; Tsui et al., 2004, *J Med Genet;* 41(6):461-7; Go et al., 2004, *Clin Chem;* 50(8):1413-4; Smets et al., 2006, *Clin Chim Acta;* 364(1-2):22-32; Tsui et al., 2006, *Methods Mol Biol;* 336:123-34; Purwosunu et al., 2007, *Clin Chem;* 53(3):399-404; Chim et al., 2008, *Clin Chem;* 54(3):482-90; Tsui and Lo, 2008, *Methods Mol Biol;* 444:275-89; Lo, 2008, *Ann N Y Acad Sci;* 1137:140-143; Miura et al., 2010, *Prenat Diagn;* 30(9):849-61; Li et al., 2012, *Clin Chim Acta;* 413(5-6):568-76; Williams et al., 2013, *Proc Natl Acad Sci USA;* 110(11):4255-60; Tsui et al., 2014, *Clin Chem;* 60(7):954-62; Tsang et al., 2017, *Proc Natl Acad Sci USA;* 114(37):E7786-E7795, and US Patent Publication US 2014/0243212 may be used in the methods described herein.

The detection and identification of biomarkers of a C-RNA signature within the maternal circulation indicative of preeclampsia or a risk for developing preeclampsia may involve any of a variety of technologies. For example, biomarkers may be detected in serum by radioimmunoassay or the polymerase chain reaction (PCR) technique may be used.

In various embodiments, the identification of the biomarkers of a C-RNA signature within the maternal circulation indicative of preeclampsia or a risk for developing preeclampsia may involve sequencing the C-RNA molecules. Any of a number of sequencing technologies can be utilized, including, but not limited to, any of a variety of high-throughput sequencing techniques.

In some embodiments, the C-RNA population within a maternal biosample may be subject to enrichment of RNA sequences the include protein-coding sequences prior to sequencing. Any of a variety of platforms available for whole-exome enrichment and sequencing may be used, including but not limited to the Agilent SureSelect Human All Exon platform (Chen et al., 2015a, *Cold Spring Harb Protoc;* 2015(7):626-33. doi: 10.1101/pdb.prot083659); the Roche NimbleGen SeqCap EZ Exome Library SR platform (Chen et al., 2015b, *Cold Spring Harb Protoc;* 2015(7):634-41. doi: 10.1101/pdb.prot084855); or the Illumina TruSeq Exome Enrichment platform (Chen et al., 2015c, *Cold Spring Harb Protoc;* 2015(7):642-8. doi:10.1101/pdb.prot084863). See also "TruSeq™ Exome Enrichment Guide," Catalog #FC-930-1012 Part #15013230 Rev. B November 2010 and Illumina's "TruSeq™ RNA Sample Preparation Guide," Catalog #RS-122-9001DOC Part #15026495 Rev. F March 2014.

In particular embodiments, biomarkers of a C-RNA signature within the maternal circulation indicative of preeclampsia or a risk for developing preeclampsia may be detected and identified using microarray techniques. In this method, polynucleotide sequences of interest are plated, or arrayed, on a microchip substrate. The arrayed sequences are then hybridized with a maternal biosample, or a purified and/or enriched portion thereof. Microarrays may include a variety of solid supports including, but not limited to, beads, glass microscope slides, glass wafers, gold, silicon, microchips, and other plastic, metal, ceramic, or biological surfaces. Microarray analysis can be performed by commercially available equipment, following manufacturer's protocols, such as by using Illumina's technology.

With obtaining, shipping, storing, and/or processing blood samples for the preparation of circulating RNA, steps may be taken to stabilize the sample and/or prevent the disruption of cell membranes resulting in the release of cellular RNAs into the sample. For example, in some embodiments, blood samples may be collected, shipped, and/or stored in tubes that have cell- and DNA-stabilizing properties, such as Streck Cell-Free DNA BCT® blood collection tubes, prior to processing into plasma. In some embodiments, blood samples are not exposed to EDTA. See, for example, Qin et al., 2013, *BMC Research Notes;* 6:380 and Medina Diaz et al., 2016, *PLoS ONE;* 11(11):e0166354.

In some embodiments, blood samples are processed into plasma within about 24 to about 72 hours of the blood draw, and in some embodiments, within about 24 hours of the blood draw. In some embodiments, blood samples are maintained, stored, and/or shipped at room temperature prior to processing into plasma.

In some embodiments, blood samples are maintained, stored, and/or shipped without exposure to chilling (for example, on ice) or freezing prior to processing into plasma.

The disclosure includes kits for use in the diagnosis of preeclampsia and the identification of pregnant women at risk for developing preeclampsia. A kit is any manufacture (e.g. a package or container) including at least one reagent, e.g. a probe, for specifically detecting a C-RNA signature within the maternal circulation as described herein that is indicative of preeclampsia or a risk for developing preeclampsia. The kit may be promoted, distributed, or sold as a unit for performing the methods of the present disclosure.

The use of signatures of circulating RNA found in the maternal circulation specific to preeclampsia in noninvasive methods for the diagnosis of preeclampsia and the identification of pregnant women at risk for developing preeclampsia may be combined with appropriate monitoring and medical management. For example, further tests may be ordered. Such test may include, for example, blood tests to measure liver function, kidney function, and/or platelet and various clotting proteins, urine analysis to measure protein or creatinine levels, fetal ultrasound to measure monitor fetal growth, weight, and amniotic fluid, a nonstress test to measure how fetal heart rate with fetal movement, and/or a biophysical profile using ultrasound to measure your fetal breathing, muscle tone, and movement and the volume of amniotic fluid may be ordered. Therapeutic interventions may include, for example, increasing the frequency of prenatal visits, antihypertensive medications to lower blood pressure, corticosteroid medications, anticonvulsant medications, bed rest, hospitalization, and/or early delivery. See, for example, Townsend et al., 2016 "Current best practice in the management of hypertensive disorders in pregnancy," *Integr Blood Press Control;* 9: 79-94.

Therapeutic interventions may include the administration of low dose aspirin to pregnant women identified at risk of for developing preeclampsia. A recent multicenter, double-blind, placebo-controlled trial demonstrated that treatment of women at high risk for preterm preeclampsia with low-dose aspirin resulted in a lower incidence of this diagnosis compared to placebo (Rolnik et al., 2017, "Aspirin versus Placebo in Pregnancies at High Risk for Preterm Preeclampsia," *N Engl J Med;* 377(7):613-622). Dosages of low dose aspirin include, but are not limited to, about 50 to about 150 mg per day, about 60 to about 80 mg per day, about 100 or more mg per day, or about 150 mg per day. Administration may begin, for example, at or before 16 weeks of gestation or from 11 to 14 weeks of gestation. Administration may continue thru 36 weeks of gestation.

The present invention is illustrated by the following examples. It is to be understood that the particular examples, materials, amounts, and procedures are to be interpreted broadly in accordance with the scope and spirit of the invention as set forth herein.

EXAMPLES

Example 1

C-RNA Signatures Unique to Pregnancy

Figure 2:
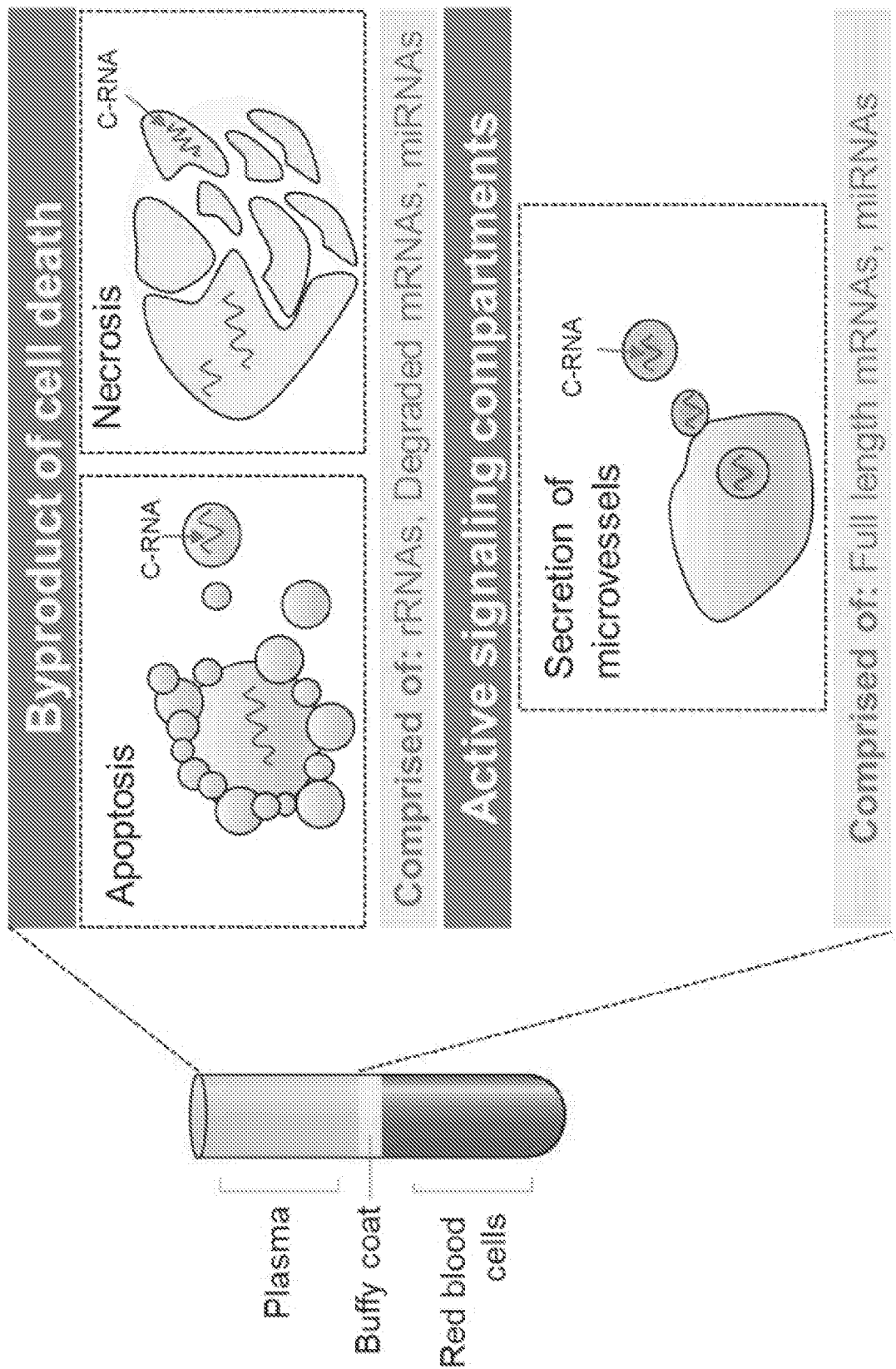
FIG. 2. Origins of circulating RNA (C-RNA).

The presence of circulating nucleic acid in maternal plasma provides a window into the progression and health of the fetus and the placenta (FIG. 1). Circulating RNA (C-RNA) is detected in maternal circulation and originates from two predominant sources. A significant fraction of C-RNA originates from apoptotic cells, which release vesicles containing C-RNA into the blood stream. C-RNA also enters maternal circulation through the shedding of active signaling vesicles such as exosomes and microvesicles from a variety of cell types. As shown in FIG. 2, C-RNA is therefore comprised of the byproducts of cell death as well as active signaling products. Characteristics of C-RNA include generation through common processes, release from cells throughout the body, and stable and contained in vesicles. It represents a circulating transcriptome that reflects tissue-specific changes in gene expression, signaling, and cell death.

C-RNA has the potential to be an excellent biomarker for at least the following reasons:
1) All C-RNA is contained within membrane bound vesicles, which protects the C-RNA from degradation, making it quite stable in the blood.
2) C-RNA originates from all cell types. For example, C-RNA has been shown to contain transcripts from both the placenta and the developing fetus. The diverse origins of C-RNA give it the potential to be a rich repository for accessing information on both fetal and overall maternal health.

Figure 3:
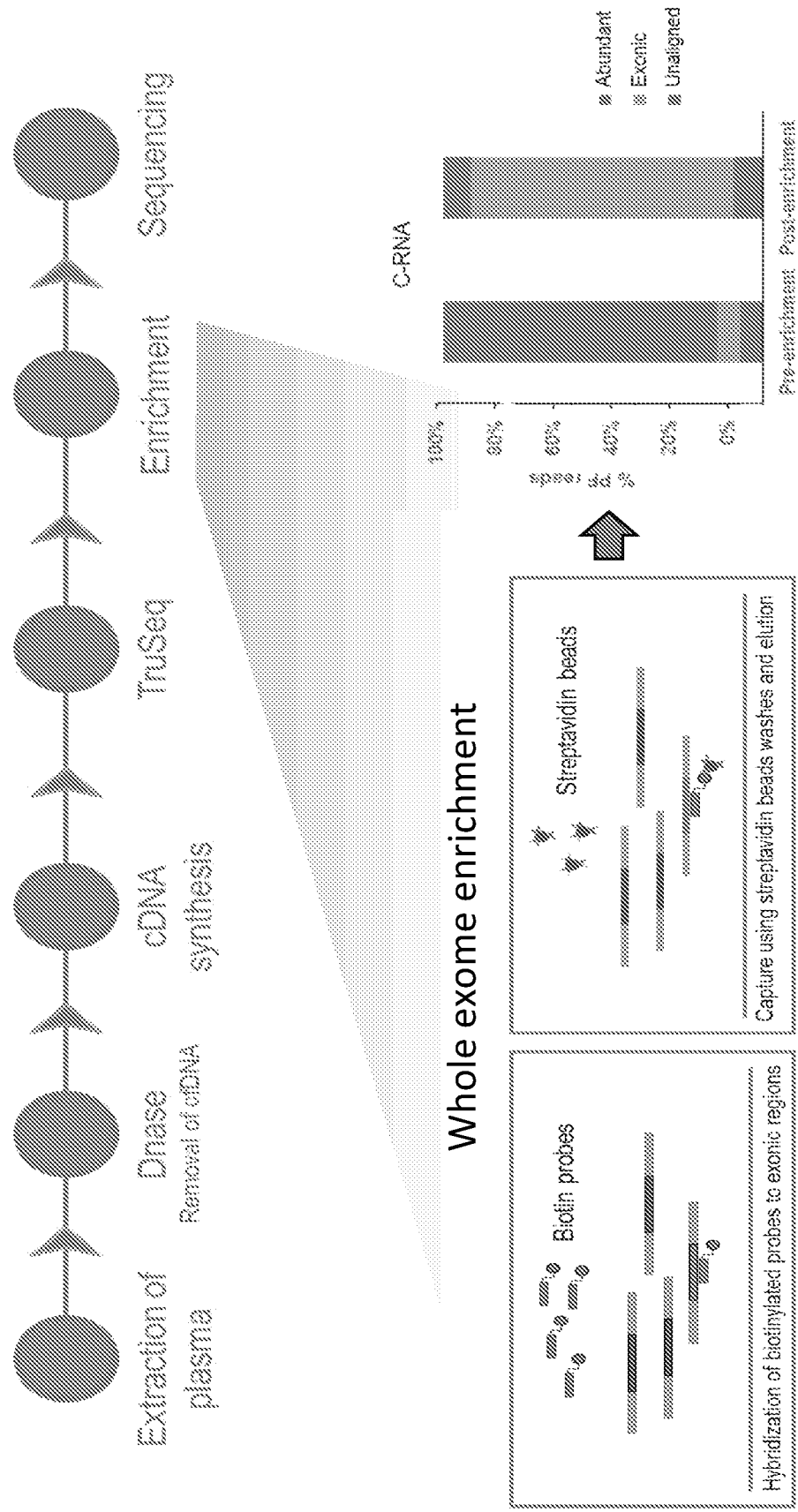
FIG. 3. Library prep workflow for C-RNA.
Figure 7:
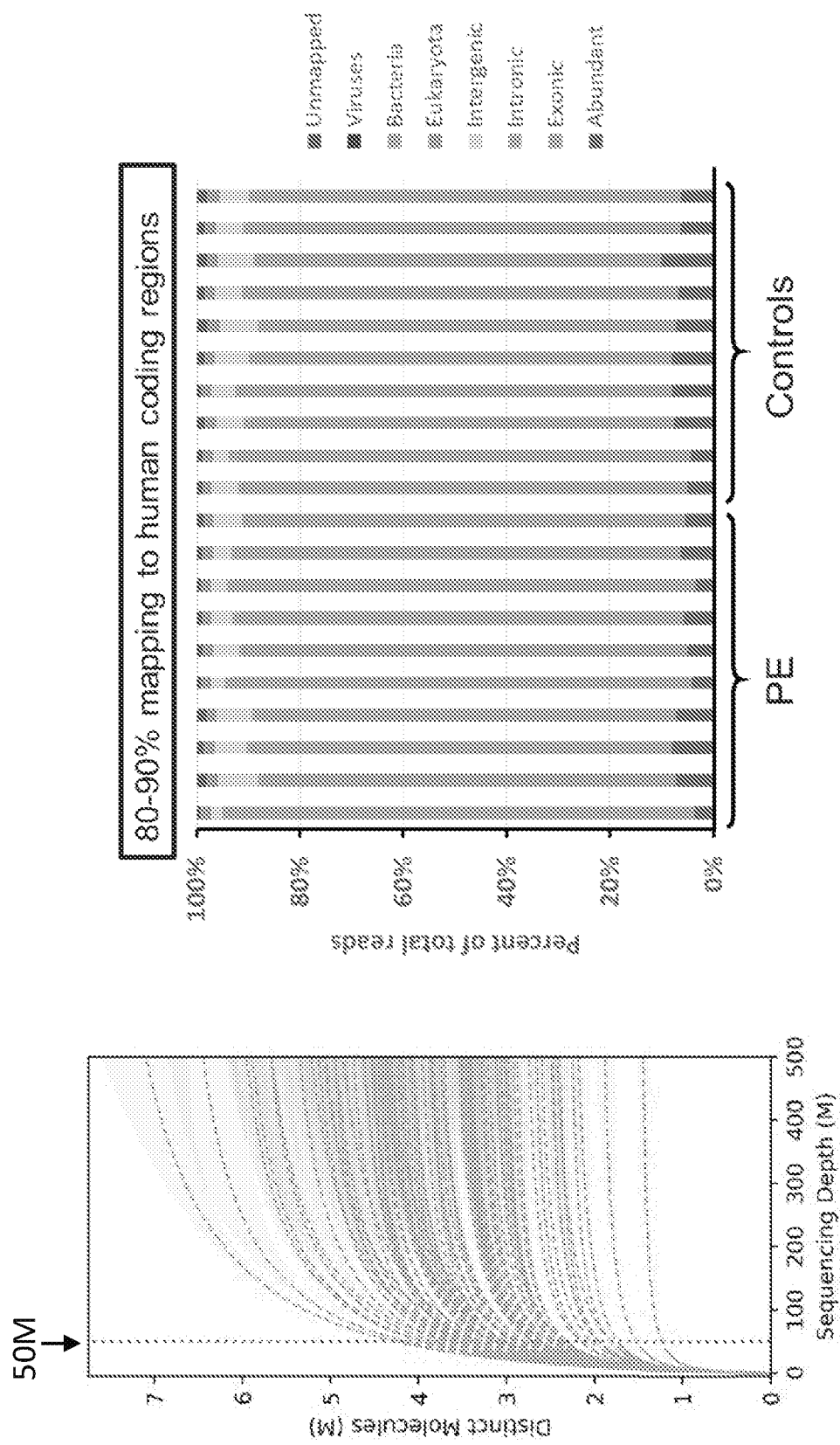
FIG. 7. Sequencing data characteristics.

C-RNA libraries were prepared from plasma samples using standard Illumina library prep and whole exome enrichment technology. This is shown in FIG. 3. Specifically, Illumina TruSeq™ library prep and RNA Access Enrichment were used. Using this approach, libraries were generated that have 90% of the reads aligning to the human coding region (FIG. 3 and FIG. 7). Samples were downsampled to 50 M reads and ≥40 M mapped reads were used for downstream analysis. Samples were processed using the C-RNA workflow shown in FIG. 3. Dual Indexed libraries. Sequenced 50λ50 on Hiseq2000

Figure 4:
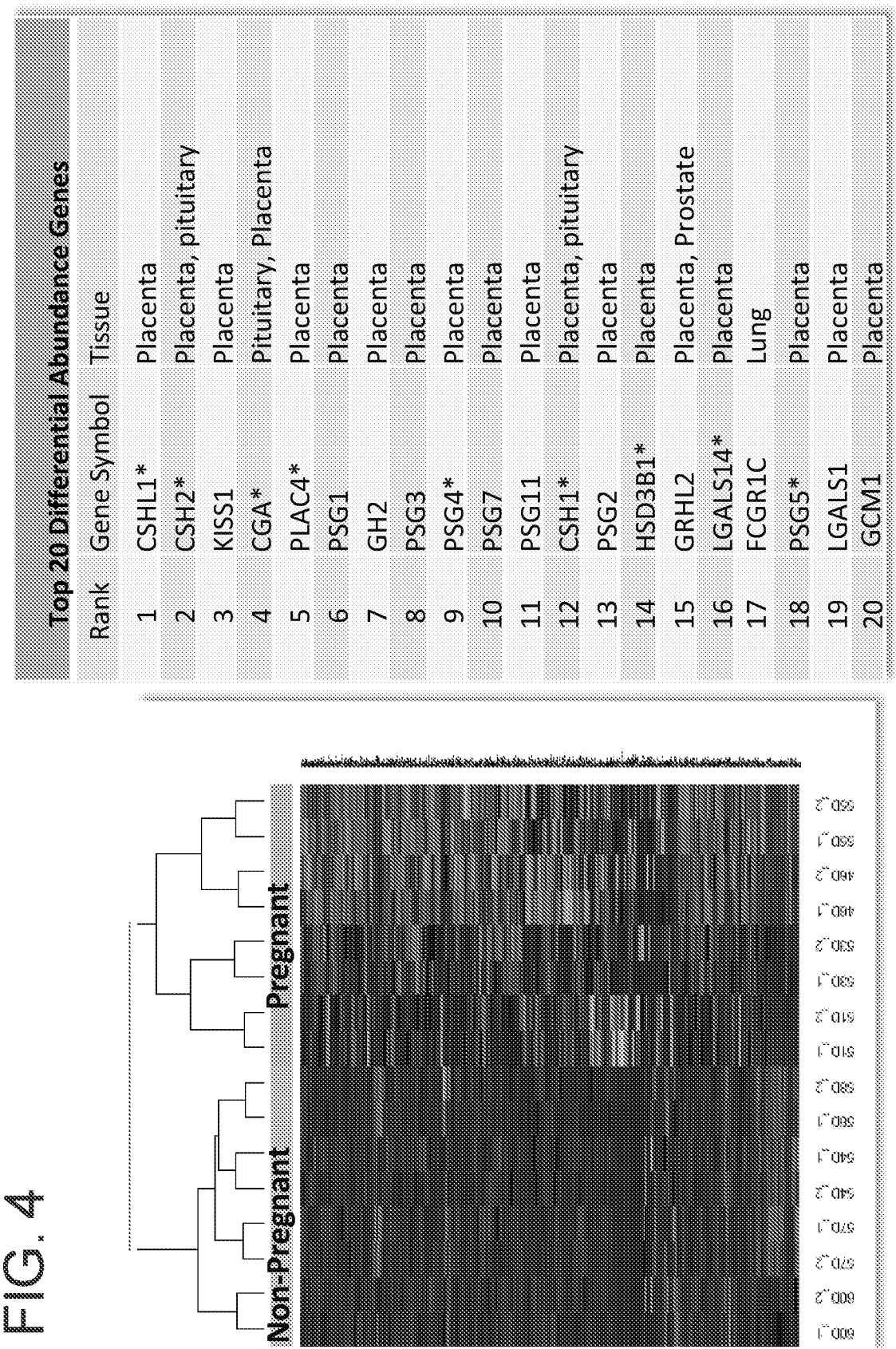
FIG. 4. Validation of C-RNA approach comparing 3rd trimester pregnant and non-pregnant samples.

As shown in FIG. 4, comparing results from plasma samples from third trimester pregnant women to plasma samples from non-pregnant women provides a clear signature unique to pregnancy. The top twenty differential abundance genes of this signature are CSHL1, CSH2, KISS1, CGA, PLAC4, PSG1, GH2, PSG3, PSG4, PSG7, PSG11, CSH1, PSG2, HSD3B1, GRHL2, LGALS14, FCGR1C, PSG5, LGALS13, and GCM1. The majority of the genes identified in the pregnancy signature are placentally expressed and also correlate with published data. These results also confirm that placental RNA can be accessed in in the maternal circulation.

Example 2

C-RNA Signatures Across Gestational Age

Figure 5:
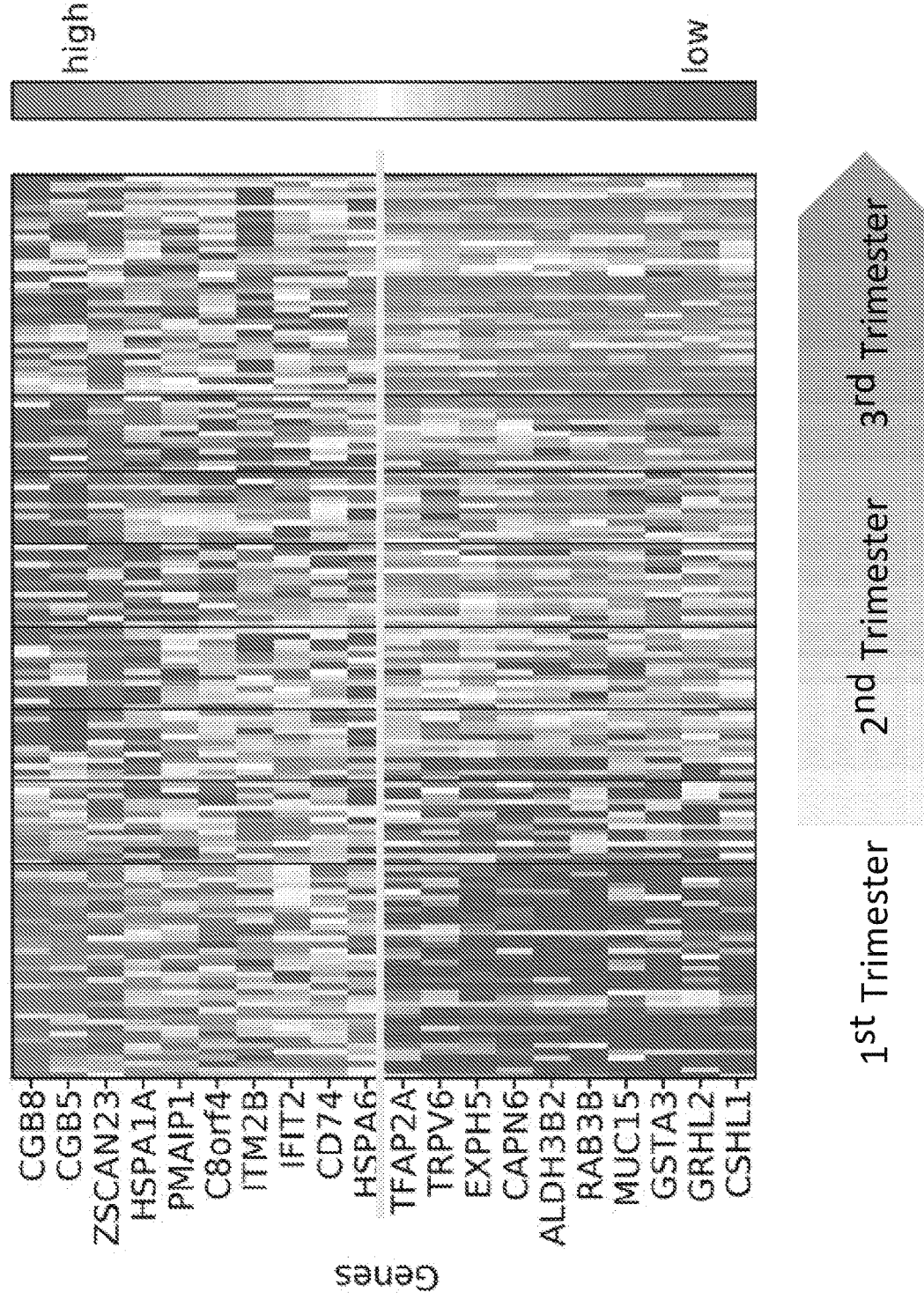
FIG. 5. Validation of C-RNA approach using longitudinal pregnancy samples.

This example characterized C-RNA signatures across different gestational ages throughout pregnancy. It is expected that the changes in C-RNA signatures at different time points longitudinally across pregnancy will be more subtle than the differences between C-RNA signatures of pregnant and non-pregnant samples noted in Example 1. As shown in FIG. 5, clear temporal changes in C-RNA profiles of the signature genes were observed as pregnancy progressed, with a clear group of genes upregulated in the first trimester and clear group of genes that increase in the third trimester.

These genes included CGB8, CGB5, ZSCAN23, HSPA1A, PMAIP1, C8orf4, ITM2B, IFIT2, CD74, HSPA6, TFAP2A, TRPV6, EXPH5, CAPN6, ALDH3B2, RAB3B, MUC15, GSTA3, GRHL2, and CSHL1, as listed in FIG. 5.

These genes may also include CSHL1, CSH2, KISS1, CGA, PLAC4, PSG1, GH2, PSG3, PSG4, PSG7, PSG11, CSH1, PSG2, HSD3B1, GRHL2, LGALS14, FCGR1C, PSG5, LGALS13, and GCM1.

These changes throughout the course of pregnancy correlate with published data from both Steve Quake and Dennis Lo. See, for example, Maron et al., 2007, "Gene expression analysis in pregnant women and their infants identifies unique fetal biomarkers that circulate in maternal blood," *J Clin Invest;* 117(10):3007-3019; Koh et al., 2014, "Noninvasive in vivo monitoring of tissue-specific global gene expression in humans," *Proc Natl Acad Sci USA;* 111(20):7361-6; and Ngo et al., 2018, "Noninvasive blood tests for fetal development predict gestational age and preterm delivery," *Science;* 360(6393):1133-1136. C-RNA signatures correlating with patterns of gene expression of the placenta were found. Thus, this approach is able to detect subtle changes within pregnancy and provides non-invasive means to monitor placental health.

Example 3

C-RNA Signatures of Preeclampsia

Figure 6:
FIG. 6. Description of clinical studies.

With this example, C-RNA signatures unique to preeclampsia were identified. C-RNA signatures were determined in samples collected from pregnant women diagnosed with preeclampsia from two studies, the RGH14 Study (registered with clinical trials.gov as NCT0208494) and the Pearl Study (also referred to herein as the Pearl Biobank; registered with clinical trials.gov as NCT02379832)), were assayed (FIG. 6). Two tubes of blood were collected at the time of diagnosis for preeclampsia. Eighty controls samples matched for gestational age were collected to minimize transcriptional variability not related to the preeclampsia disease state and to control for gestational age differences in C-RNA signatures. Samples from the RGH14 study were used to identify a set of biologically relevant genes, and the predictive value of these biomarkers was validated in an independent cohort of samples from the Pearl Biobank.

In the analysis of the RGH14 data, C-RNA signatures unique to preeclampsia (PE) were identified using four different methods, the TREAT method, a Bootstrap method, a jackknifing method, and the Adaboost method. Example 3 focuses on the first 3 analysis methods and Example four focuses on the Adaboost method.

The t-test relative to threshold (TREAT) statistical method utilizing the EDGR program allows researchers to formally test (with associated p-values) whether the differential expression in a microarray experiment is greater than a given (biologically meaningful) threshold. See McCarthy and Smyth, 2009 "Testing significance relative to a fold-change threshold is a TREAT," Bioinformatics; 25(6):765-71 for a more detailed description of the TREAT statistical method and Robinson et al., 2010, "edgeR: a Bioconductor package for differential expression analysis of digital gene expression data," Bioinformatics; 26:139-140 for a more detailed description of the EDGR program. See Freund and Schapire, 1997, "A Decision-Theoretic Generalization of On-Line Learning and an Application to Boosting," *Journal of Computer and Systems Sciences;* 55(1):119-139 and Pedregosa et al., 2011, "Scikit-learn: Machine Learning in Python," *JMLR;* 12:2825-2830 for a more detailed description of the Adaboost method. The Adaboost method will be discussed in Example 4.

In the first method, standard statistical testing (TREAT method) was used to identify genes that are statistically different in the RGH14 preeclampsia cohort of 40 patients as compared to a subset of matched controls (40 patients). 122 genes were identified as statistically different in the preeclampsia cohort (40 patients) as compared to a subset of matched controls (40 patients) (FIG. 8, right panel). These genes include CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMP5, PTGDR2, NOMO1, NXF3, PLD4, BPIFB3, PACSIN1, CUX2, FLG, CLEC4C, and KRT5.

Figure 15:
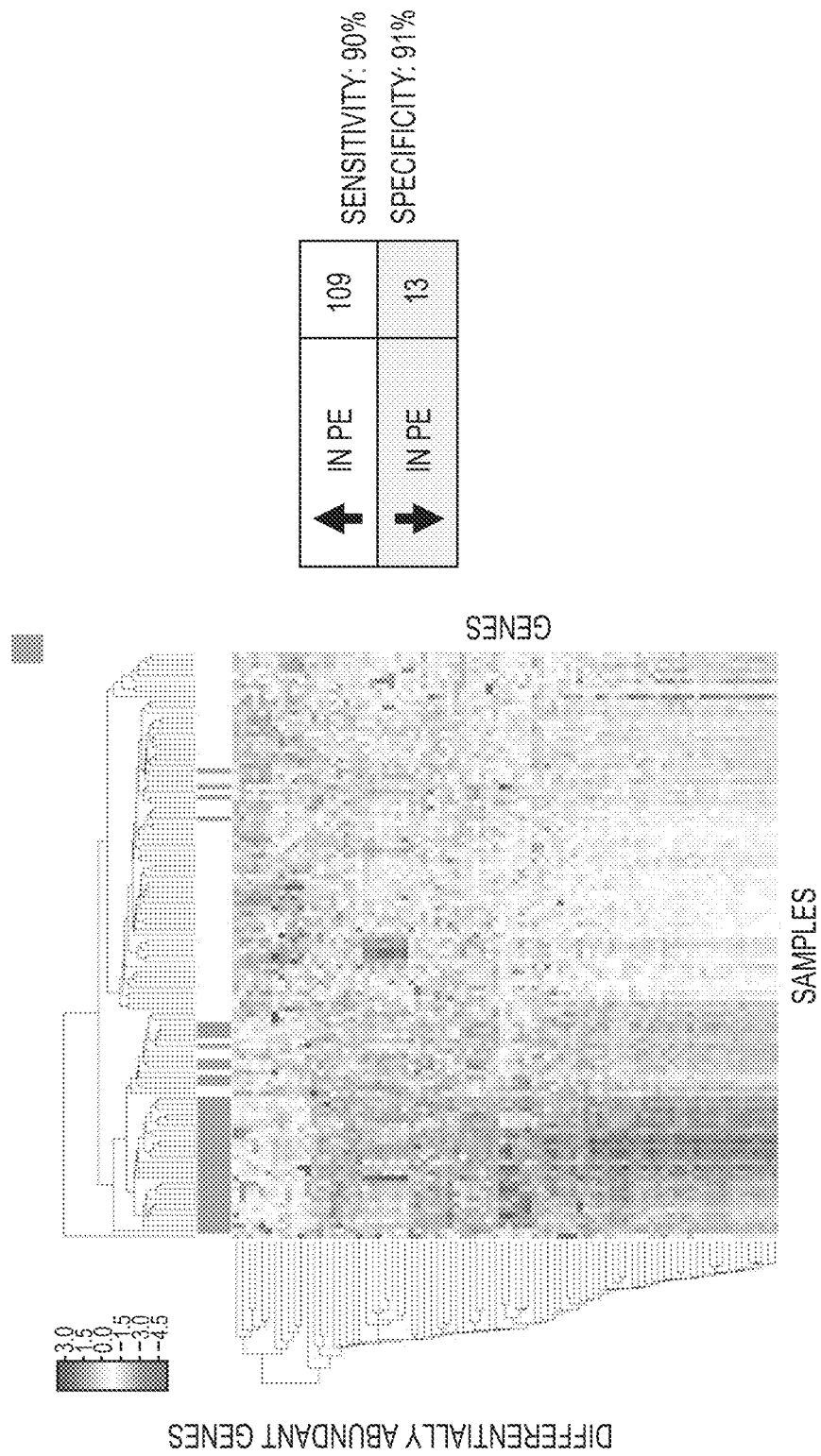
FIG. 15. Classification of preeclampsia with standard DEX TREAT analysis.

The TREAT method did not identify a set of genes that 100% accurately classifies the preeclampsia patients into a separate group (FIG. 15). However, focusing in on these identified genes did improve classification compared to using the entire data set of all measured genes (FIG. 8, left panel). This highlights the value of focusing in on a subset of genes for prediction. However, with the TREAT method, a significant amount of variability was observed in the genes identified depending on which controls were selected. To deal with this biological variability and further improve the predictive value of our gene list, a second bootstrapping approach was developed.

Figure 9:
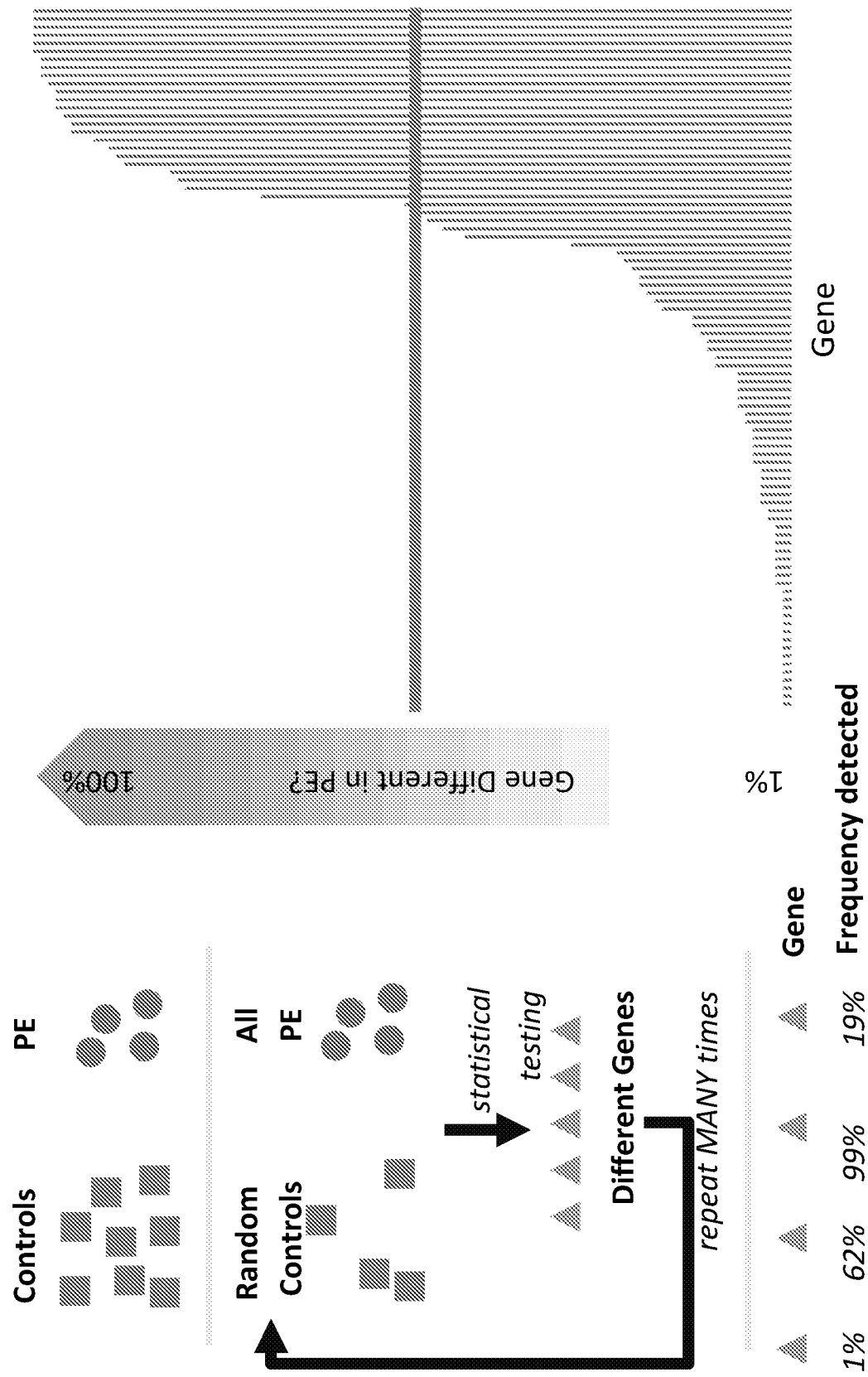
FIG. 9. Description of bootstrapping method.
Figure 10:
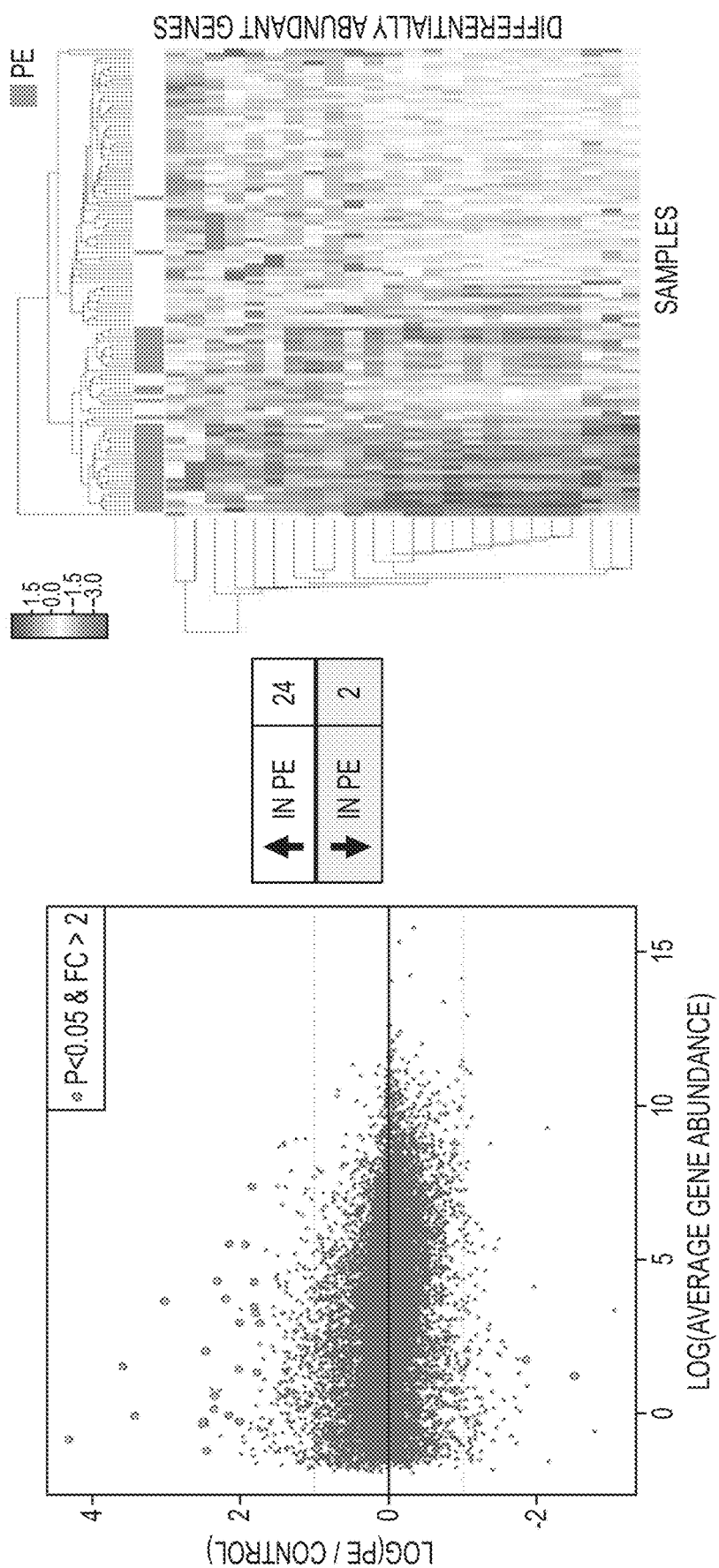
FIG. 10. Classification of preeclampsia samples with bootstrapping approach.

In the RGH14 study more control samples (80) are available than preeclampsia patient samples (40). Thus, the RGH14 cohort of 40 preeclampsia patient samples was compared to a random selection of 40 controls samples (still matched for gestational age) and a gene list that is statistically different in the preeclampsia cohort was identified. As shown in FIG. 9, this was then repeated 1,000 times, to identify how often a set of genes was identified. A significant subset of genes only show up less than 10 times out of the 1,000 iterations (less than 1% of the 1,000 iterations). These low frequency genes most likely are due to biological noise and may not reflect a gene that is universally specific to preeclampsia. So, the gene list was further downselected by requiring a gene to be considered as statistically different in the preeclampsia cohort only if identified in 50% of the 1,000 iterations performed (FIG. 9, right panel). As shown in FIG. 10, differential transcript abundance with the additional bootstrapping selection distinguishes preeclampsia samples from healthy controls. Using this additional requirement helped address biological variability and further improved the ability to classify preeclampsia samples correctly.

Figure 11:
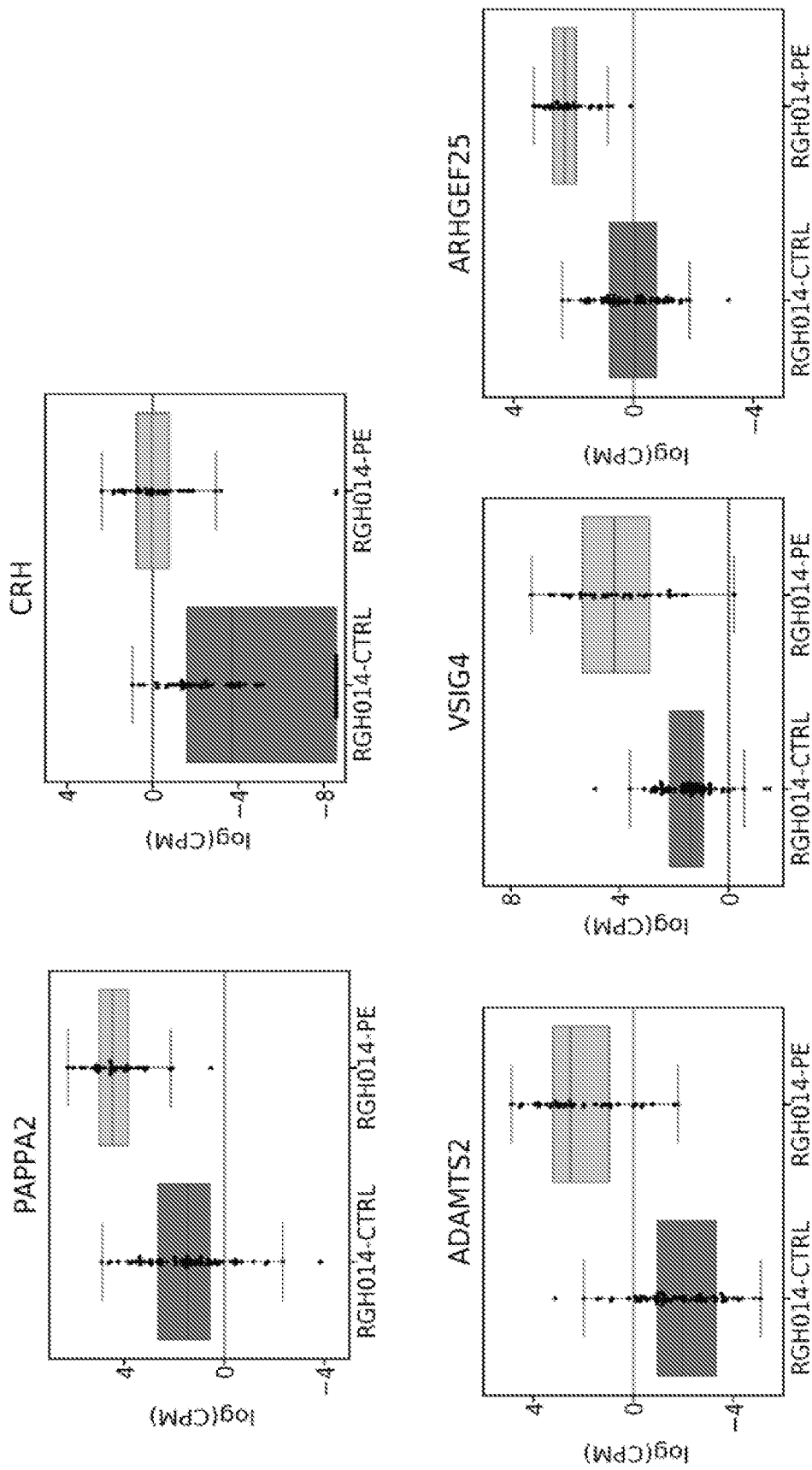
FIG. 11. Examination of over-abundant preeclampsia genes.

Using this Bootstrap method, 27 genes were identified as statistically associated with preeclampsia. These genes include TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4. The genes identified with this bootstrapping method had excellent concordance with published data. Approximately 75% of these genes are expressed by the placenta. As shown in FIG. 11, there is overlap with known markers of preeclampsia, including PAPPA and CRH. And, a significant number of these genes are involved in embryo development, extracellular matrix remodeling, immune regulation, and cardiovascular function, all pathways known to be dysregulated in preeclampsia.

A third jackknifing approach was also developed to capture the subset of genes with the highest predictive value. This approach is similar to the bootstrapping method. Patients from both preeclampsia and control groups were randomly subsampled and differentially abundant genes identified 1,000 times. Instead of using the frequency with which a gene is identified as statistically different, the jackknifing approach calculated confidence intervals (95%, one-sided) for the p-value of each transcript. Genes where this confidence interval exceeded 0.05 were excluded. (FIG. 16, left panel).

Using the jackknifing approach, 30 genes were identified as predictive of preeclampsia: VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, HTRA4.

Figure 16:
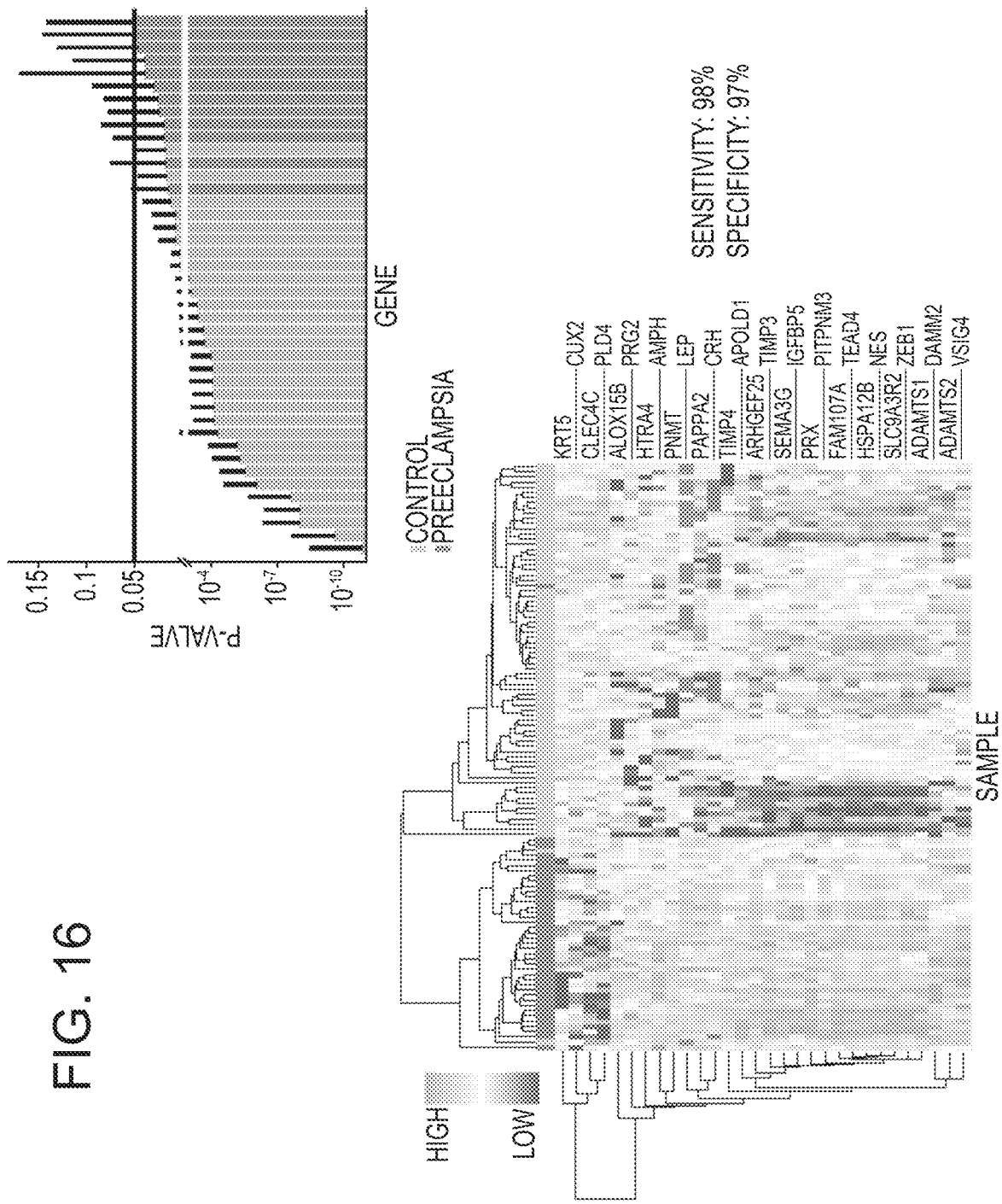
FIG. 16. Selection of genes and classification of preeclampsia with jackknifing approach.
Figure 17:
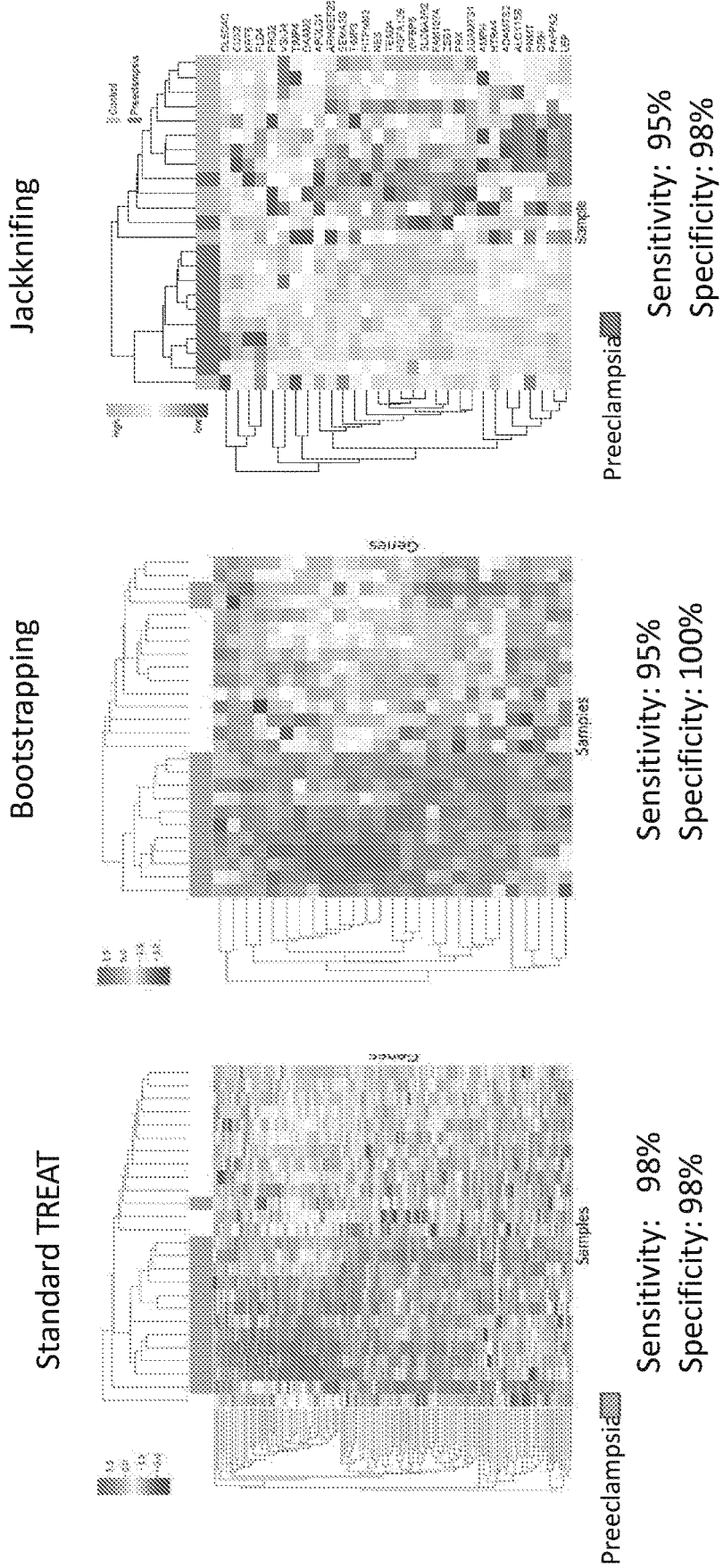
FIG. 17. Validation of TREAT, Bootstrapping, and Jackknifing approaches in independent PEARL biobank cohort.

As shown in FIG. 16 right panel, this approach gave good classification of preeclampsia patients in the RGH14 data set (compare FIG. 15 (TREAT), FIG. 10 (bootstrapping) and FIG. 16 (jackknifing)). Each identified gene list was also used to classify preeclampsia samples in the independent Pearl Biobank dataset. As shown in FIG. 17, each gene list was able to classify preeclampsia samples.

All genes identified by the bootstrapping and jackknifing methods are represented in the 122 TREAT method genes (Table 2, DEX analysis, TruSeq library prep method). The bootstrapping and jackknifing approach gene lists are highly concordant, with over 70% of genes in common. Nearly 90% of transcripts identified by any approach exhibit increased transcript abundance in preeclampsia patients, consistent with elevated signaling and/or cell death in this disease.

Example 4

Identification of C-RNA Signatures with Adaboost

Figure 12:
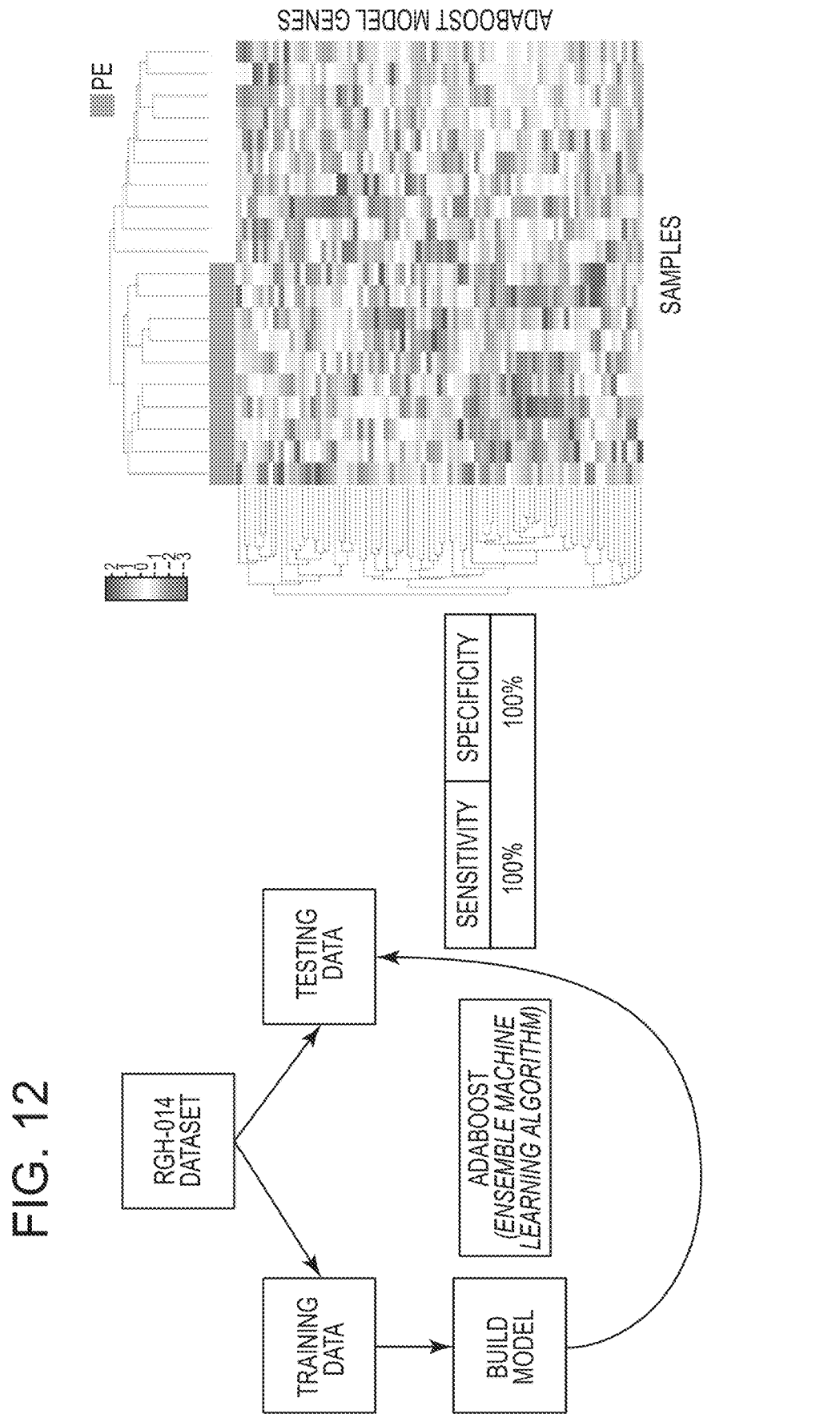
FIG. 12. Standard Adaboost Model.
Figure 13:
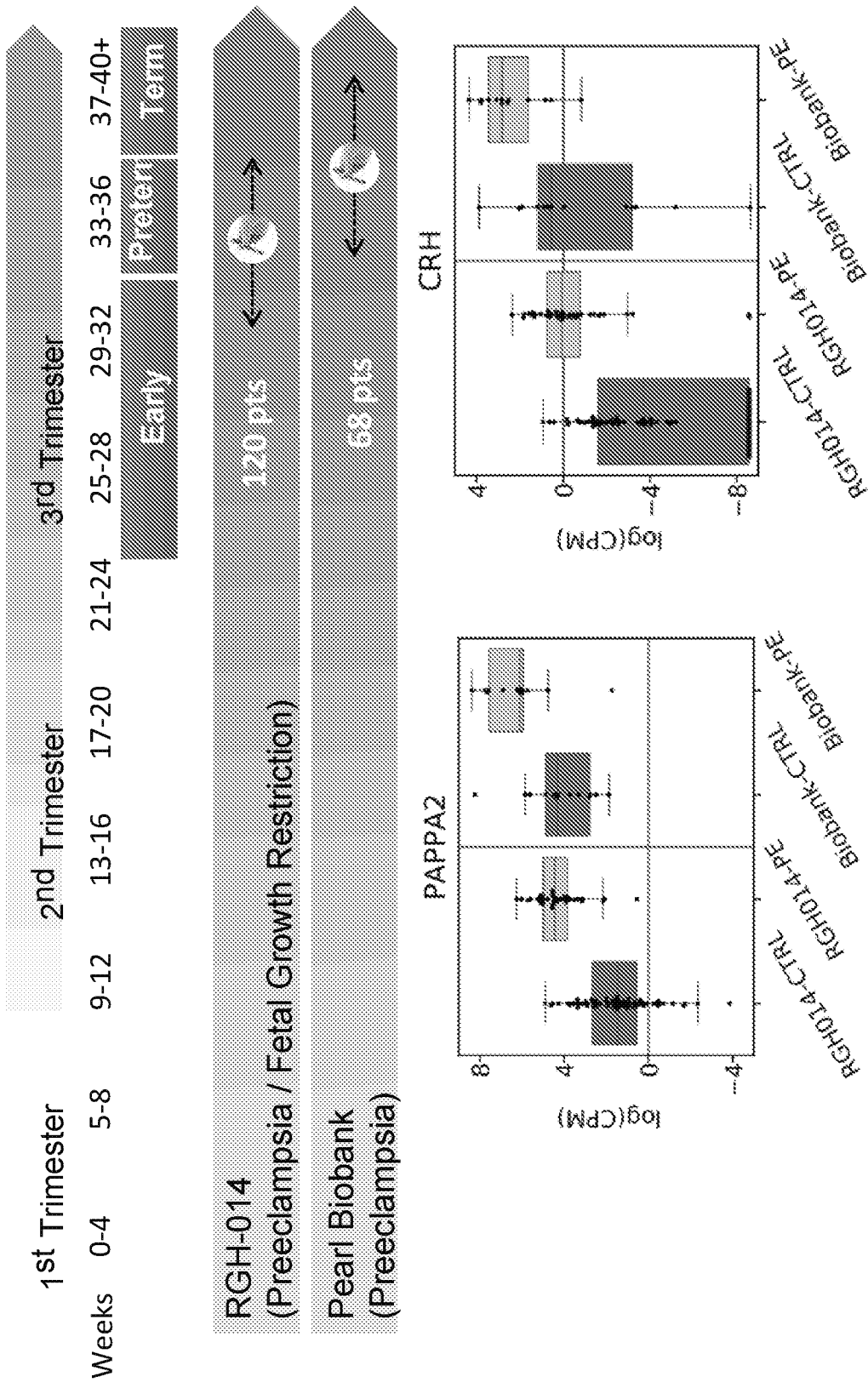
FIG. 13. Independent cohort allows further validation of preeclampsia signature.
Figure 14:
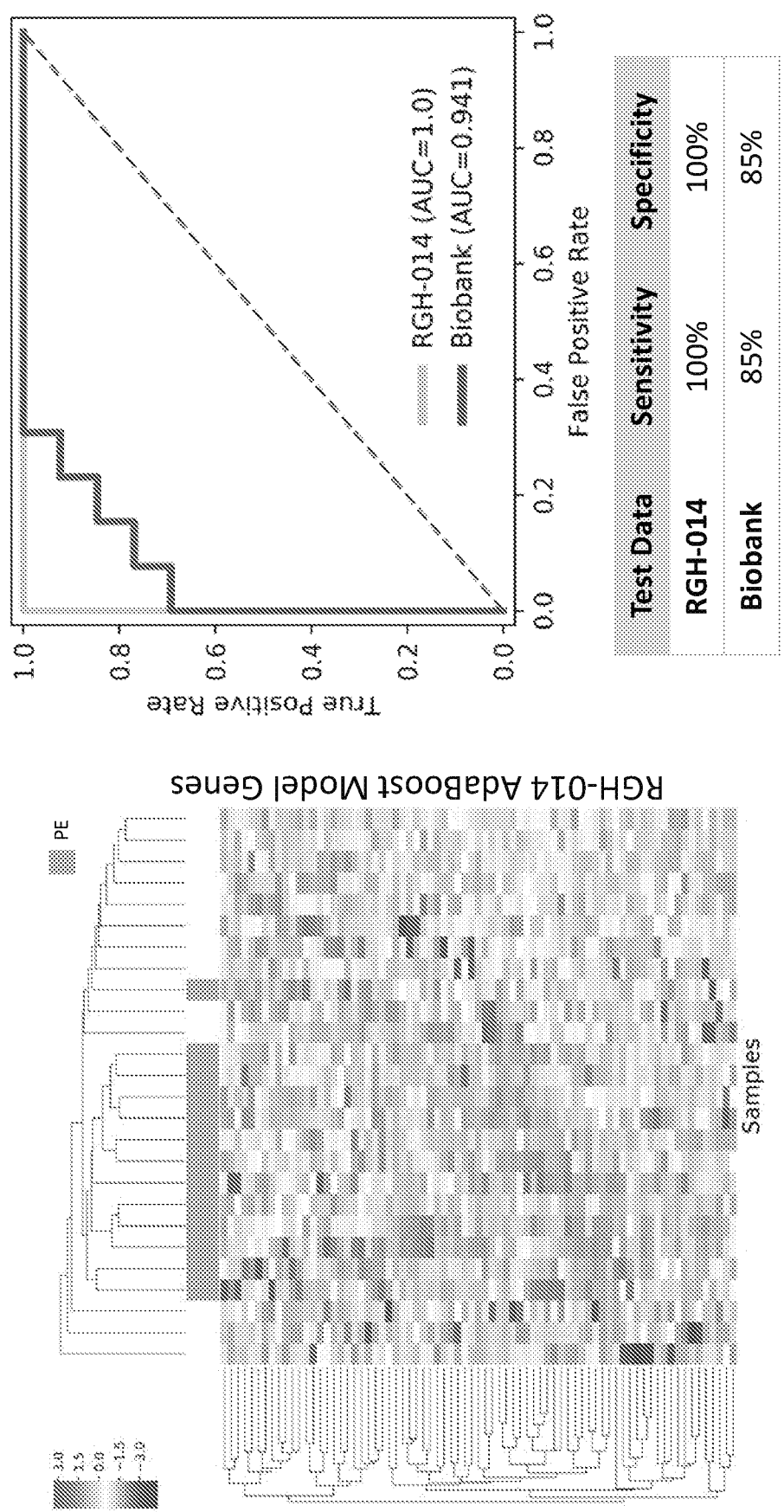
FIG. 14. Performance of standard adaboost model in classification of preeclampsia.

With this example an alternative approach, a publicly available machine learning algorithm called adaboost, was used to identify a specific C-RNA signature associated with preeclampsia. As shown in FIG. 12, this approach identifies a set of genes that has the most predictive power to classify a sample as preeclampsia (PE) or normal. Using this gene list, the clearest separation of a preeclampsia cohort from healthy controls was observed. However, this approach can also be very susceptible to overtraining to the samples used to build the model. Thus, the predictive model was validated using a completely independent data set from the PEARL study (FIG. 13). Using this Adaboost gene list, 85% of the preeclampsia samples were accurately classify with 85% specificity (FIG. 14). Overall, the Adaboost machine learning approach built the most accurate predictive model for preeclampsia.

Using the Adaboost method, 75 genes were identified as statistically associated with preeclampsia (Table 3, AdaBoost Analysis, TruSeq library prep method). These genes include ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3.

Figure 18:
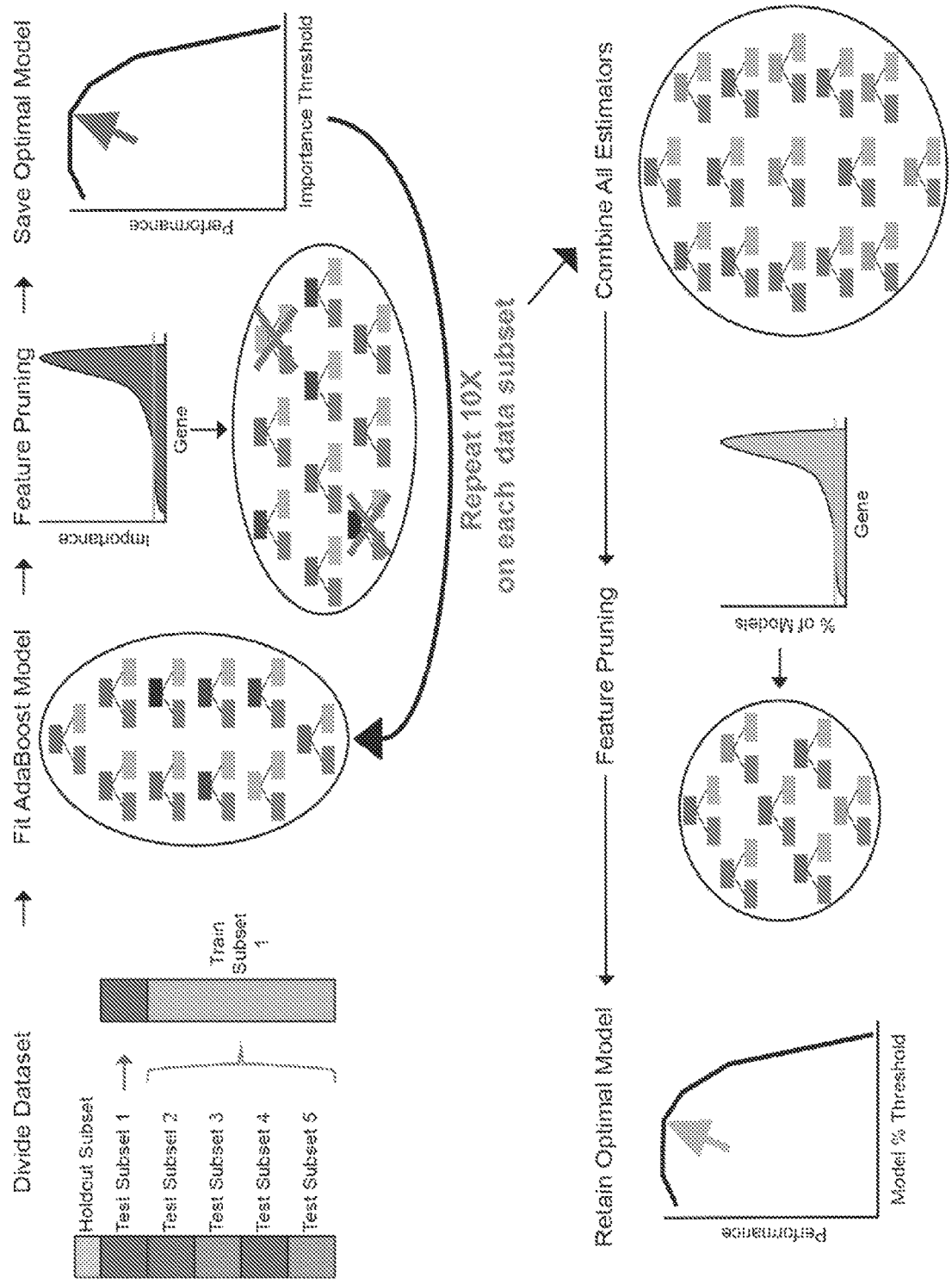
FIG. 18. A diagram of the bioinformatic approach to build AdaBoost Refined models.

A refined AdaBoost model was also developed for robust classification of PE samples. In order to create a generalized machine learning model that could accurately predict new samples, we used a rigorous approach that avoided overfitting to a single dataset and validated the final classifier with samples not used for model building. As illustrated in FIG. 18, the RGH14 dataset was divided into 6 pieces by random selection: a holdout subset with 12% of samples which was excluded from model building, and 5 evenly sized test subsets. For each iteration subsets were designated as training data or test samples. This process, starting at building the AdaBoost model was repeated for a minimum of 10 times on this data subset. After 50 high performing models were built for the 5 test-train subsets, the estimators from all models were merged into a single AdaBoost model.

Figure 19:
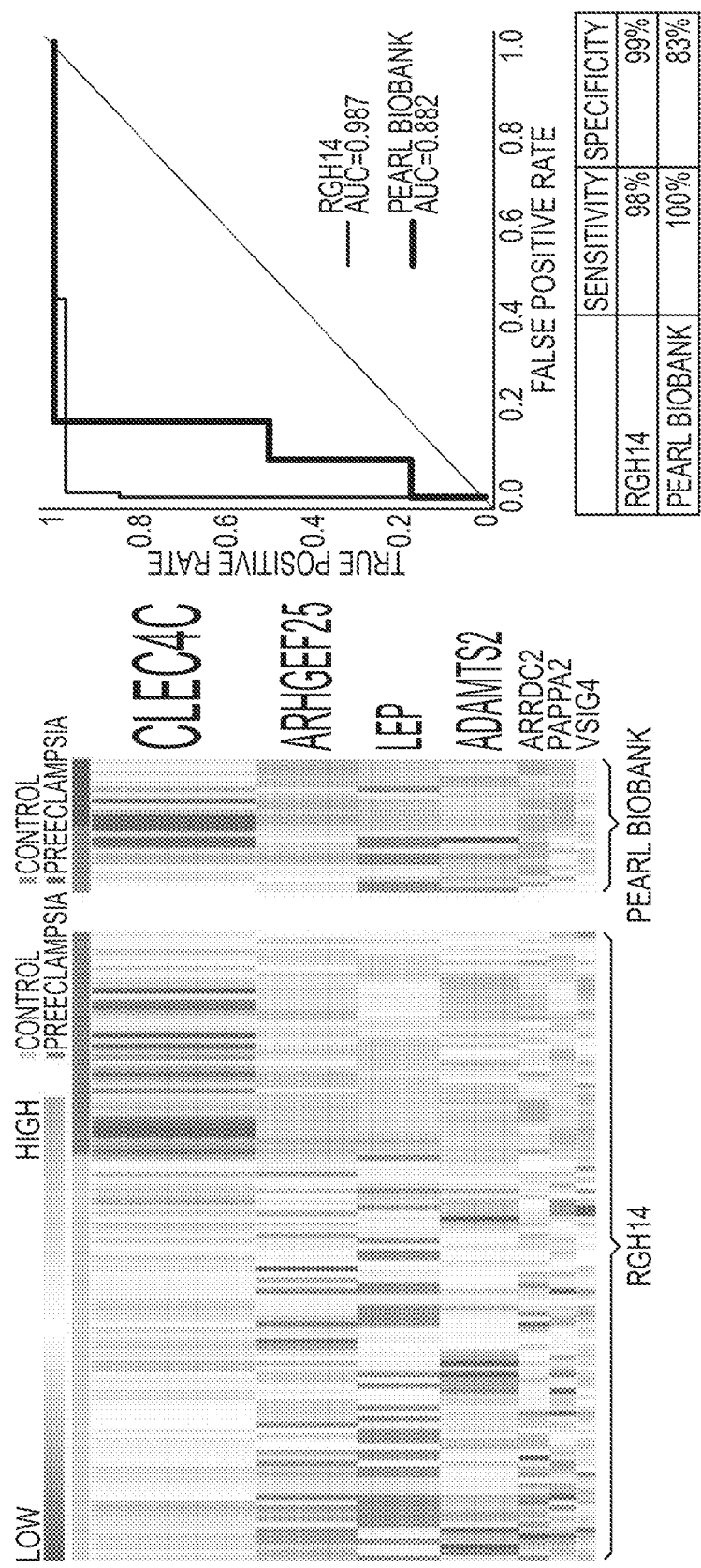
FIG. 19. Relative abundance of genes utilized by AdaBoost Refined model and their predictive capability on independent datasets.

Using the refined AdaBoost model, 11 genes were identified as statically associated with preeclampsia. These genes include CLEC4C, ARHGEF25, ADAMTS2, LEP, ARRDC2, SKIL, PAPPA2, VSIG4, ARRDC4, CRH and NES. The performance of this predictive model was validated using the hold out data set from RGH14 as well as in the completely independent Pearl Biobank cohort (FIG. 19).

AdaBoost Model Creation Description. The AdaBoost classification approach was refined in order to obtain more specific gene sets (AdaBoost Refined 1-7) by the following approach, also illustrated in FIG. 18. The RGH14 dataset was divided into 6 pieces by random selection: a holdout subset with 12% of samples which was excluded from model building, and 5 evenly sized test subsets.

For each of the test subsets, training data was assigned as all samples in neither the holdout or test samples. Gene counts for the test and training samples were TMM-normalized in edgeR, then standardized such that the training data has mean of 0 and standard deviation of 1 for each gene. An AdaBoost model with 90 estimators and 1.6 learning rate was then fit to the training data. Feature pruning was then performed by determining the feature importance of each gene in the model and testing the impact of eliminating estimators using genes with importance below a threshold value. The threshold resulting in the best performance (as measured by Matthew's correlation coefficient on test data classification) with the fewest genes was selected, and that model retained. This process, starting at building the AdaBoost model was repeated for a minimum of 10 times on this data subset.

After all 50 plus models were built for the 5 test-train subsets, the estimators from all models were merged into a single AdaBoost model. Feature pruning was performed again, this time using the percent of models incorporating a gene to for threshold values and assessing performance with the average negative log loss value for the classification of each test subset. The model which obtained the maximal negative log loss value with the fewest genes was selected as the final AdaBoost model.

AdaBoost Gene Lists. Upon repetition of this process, slight variations were observed in the genes selected for the final model, due to innate randomization in the AdaBoost algorithm implementation, however performance remained high for predicting the test data, holdout data, and independent (Pearl) datasets.

Eleven total genes were observed in at least one of 14 AdaBoost Refined models generated: ADAMTS2, ARHGEF25, ARRDC2, ARRDC4, CLEC4C, CRH, LEP, NES, PAPPA2, SKIL, VSIG4 (AdaBoost Refined 1), although no models were generated that included all simultaneously.

Two observed gene sets offered the highest performance on classification of independent data. These are AdaBoost Refined 2: ADAMTS2, ARHGEF25, ARRDC2, CLEC4C, LEP, PAPPA2, VSIG4 and AdaBoost Refined 3: ADAMTS2, ARHGEF25, ARRDC2, CLEC4C, LEP, PAPPA2, SKIL, VSIG4.

Four additional gene sets performed almost as highly as AdaBoost Refined 2-3. These are AdaBoost Refined 4: ADAMTS2, ARHGEF25, ARRDC4, CLEC4C, LEP, NES, SKIL, VSIG4; AdaBoost Refined 5: ADAMTS2, ARHGEF25, ARRDC2, ARRDC4, CLEC4C, CRH, LEP, PAPPA2, SKIL, VSIG4; AdaBoost Refined 6: ADAMTS2, ARHGEF25, ARRDC2, CLEC4C, LEP, SKIL; and AdaBoost Refined 7: ADAMTS2, ARHGEF25, ARRDC2, ARRDC4, CLEC4C, LEP, PAPPA2, SKIL.

Example 5

Identification of C-RNA Signature with Transposome Based Library Prep

The RGH14 samples were also processed through the Illumina Nextera Flex for Enrichment protocol, enriched for whole exome and sequenced to >40 million reads. This approach is more sensitive and robust for low inputs, thus likely to identify additional genes predictive of preeclampsia. This dataset was run through three analysis methods, standard differential expression analysis (TREAT), jackknifing, and the refined Adaboost model. See Example 3 and Example 4 for detailed description of these analysis methods.

Changing the method for generating libraries altered the genes detected in all three analysis methods. For the TREAT method, 26 genes were identified as differentially abundant in preeclampsia, with the majority again showing elevated abundance in preeclampsia (See Table 2, DEX Analysis, Nextera Flex for Enrichment library prep method). These genes include ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, VSIG4. FIG. 20 shows classification of the RGH14 samples with this gene list.

Applying the jackknifing analysis method downselected the TREAT list to 22 genes identified as differentially abundant in preeclampsia. These genes included ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, VSIG4. The improved performance of this list is shown in FIG. 20.

Figure 21:
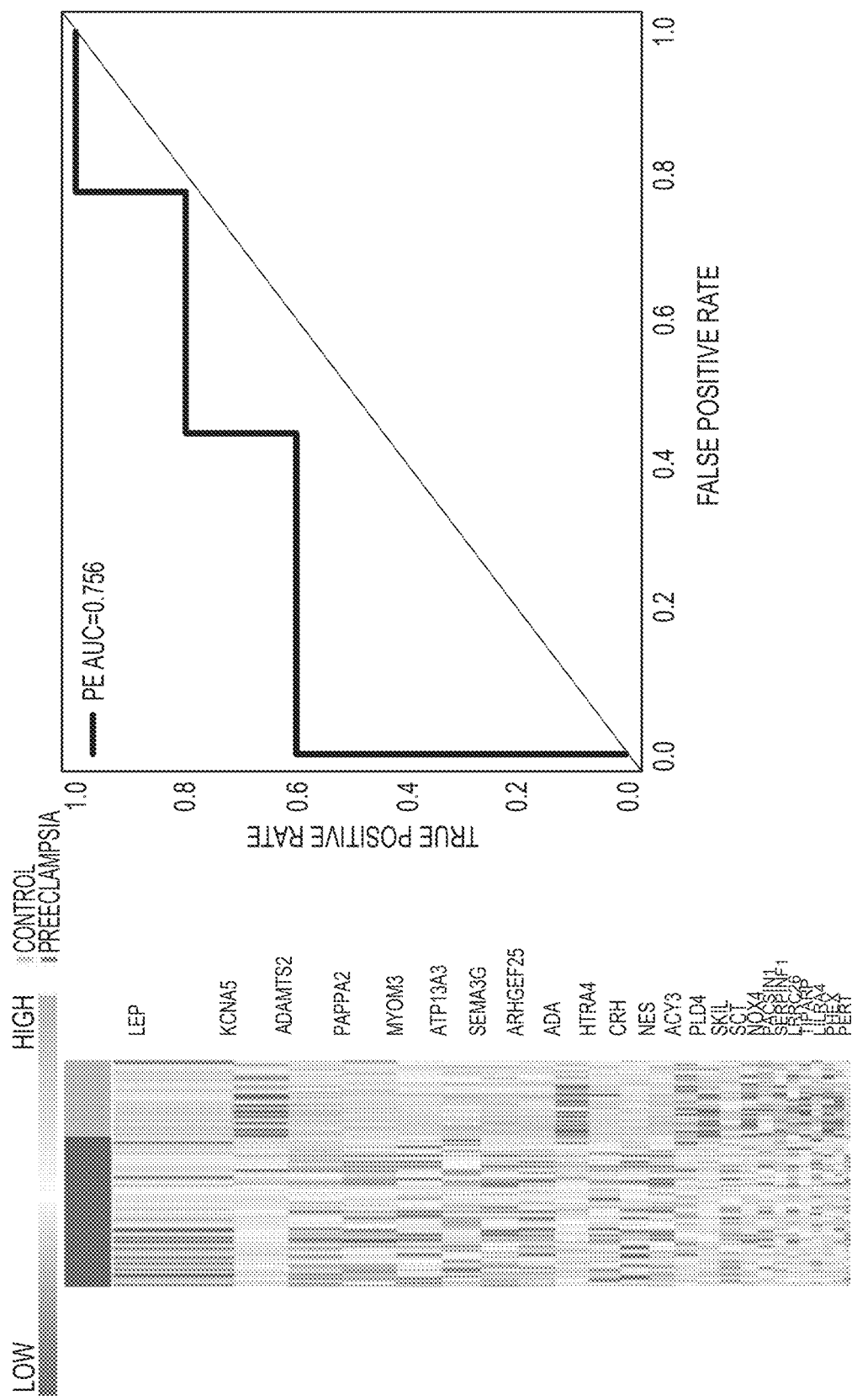
FIG. 21. Relative abundance of genes utilized by AdaBoost Refined model on Nextera Flex generated libraries and their predictive power in RGH14 dataset.

The refined AdaBoost model approach was applied to this data, as described in Example 4. Using this method, 24 genes are identified as statically associated with preeclampsia (Table 3, AdaBoost Analysis, Nextera Flex for Enrichment library prep method). These genes include LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMAG3, TIPARP, LRRC26, PHEX, LILRA4, and PER1. The performance of this predictive model is indicated in FIG. 21.

Example 6

Circulating Transcriptome Measurements from Maternal Blood Detects Early-Onset Preeclampsia Signature Molecular tools to non-invasively monitor pregnancy health from conception to birth would enable accurate detection of pregnancies at risk for adverse outcomes. Circulating RNA (C-RNA) is released by all tissues into the bloodstream, offering an accessible, comprehensive measurement of placental, fetal and maternal health (Koh et al., 2014, *Proceedings of the National Academy of Sciences;* 111:7361-7366; and Tsui et al., 2014, *Clinical Chemistry;* 60:954-962). Preeclampsia (PE), a prevalent and potentially fatal pregnancy complication, is placental in origin but gains a substantial maternal component as the disease progresses (Staff et al., 2013, *Hypertension;* 61:932-942; and Chaiworapongsa et al., 2014, *Nature Reviews Nephrology;* 10, 466-480). Yet purported biomarkers have shown limited clinical utility (Poon and Nicolaides, 2014, *Obstetrics and Gynecology International;* 2014:1-11; Zeisler et al., 2016, *N Engl J Med;* 374:13-22; and Duhig et al., 2018, F1000Research; 7:242). Hypothesizing that characterization of the circulating transcriptome may identify better biomarkers, C-RNA was analyzed from 113 pregnancies, 40 at the time of early-onset PE diagnosis. Using a novel workflow, differences were identified in the abundance of 30 transcripts which are consistent with the biology of PE and represent placental, fetal, and maternal contributions. Further, a machine learning model was developed, demonstrating that only seven C-RNA transcripts are required to classify PE in two independents cohorts (92-98% accuracy). The global measurements of C-RNA disclosed in this example highlight the utility in monitoring both maternal and fetal health and hold great promise for the diagnosis and prediction of at-risk pregnancies.

Figure 22A:
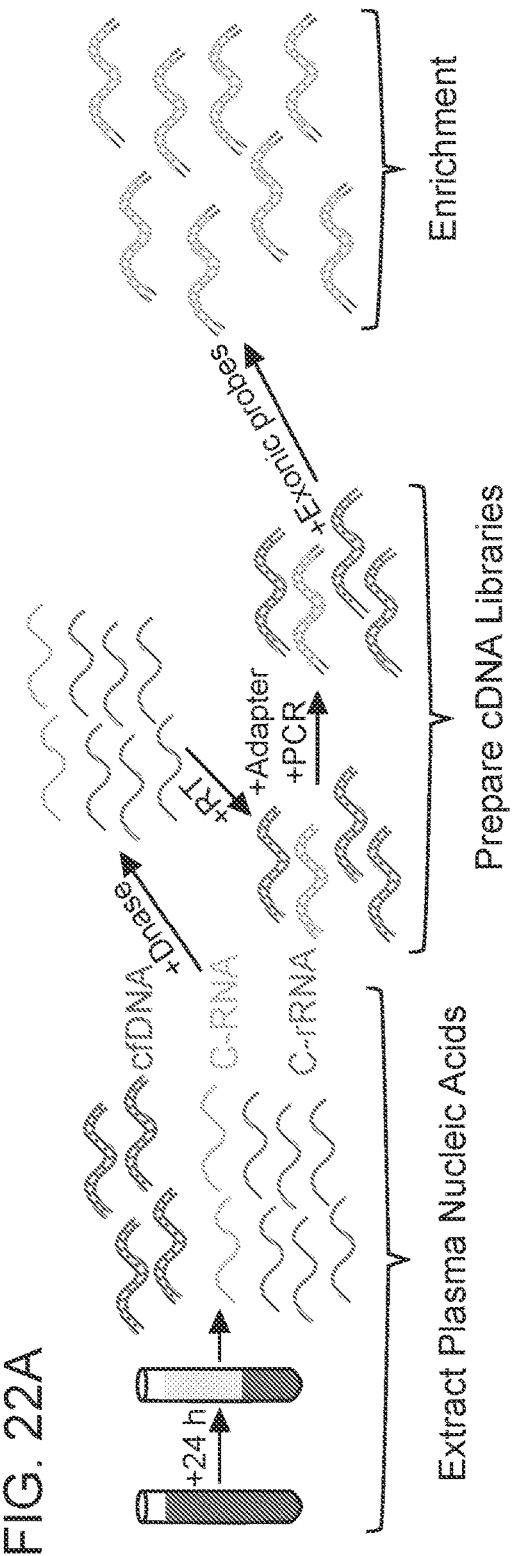
FIGS. 22A-22D. Validation of a clinic-friendly, whole-exome C-RNA analysis method.

Several studies have begun to investigate and identify potential biomarkers in C-RNA for a range of pregnancy complications (Pan et al., 2017, *Clinical Chemistry;* 63:1695-1704; Whitehead et al., 2016, *Prenatal Diagnosis;* 36:997-1008; Tsang et al., 2017, *Proc Natl Acad Sci USA;* 114: E7786-E7795; and Ngo et al., 2018, *Science;* 360:1133-1136). However, these studies have involved few patients and have been limited to monitoring small numbers of genes—almost exclusively placental and fetal derived transcripts. Measurements of the entire circulating transcriptome are difficult to perform because they require specific upfront sample collection and processing to minimize variability and contamination from cell lysis (Chiu et al., 2001, *Clinical Chemistry;* 47:1607-1613; and Page et al., 2013, *PLoS ONE;* 8: e77963). This complex workflow makes large clinical sample collections difficult to achieve because the labor required for immediate processing of blood samples is infeasible for many clinics (Marton and Weiner, 2013, *BioMed Research International;* 2013:891391). Therefore, with this example, a method was established that allows overnight shipment of blood to a processing lab where every step of sample preparation is performed in a controlled environment, providing a scalable platform for clinical trial level assessments (FIG. 22A).

The lynchpin of this method is the ability to ship blood overnight to a processing lab. The C-RNA pregnancy signal was assessed after overnight, room-temperature shipping in several tube types (FIGS. 26A-26C). Blood stored in EDTA tubes, the gold standard used by prior C-RNA studies, exhibited a reduction in the abundance of pregnancy-associated transcripts and overall instability of the transcriptomic profile (Qin et al., 2013, *BMC Research Notes;* 6:380). In contrast, the predominant tube type used for Non-Invasive Prenatal Testing (NIPT), Cell-Free DNA BCT (Streck), retained the signal from placental transcripts and had improved technical reproducibility (FIG. 26B) (Medina Diaz et al., 2016, *PLoS ONE;* 11:e0166354).

Figures 27A, 27B:
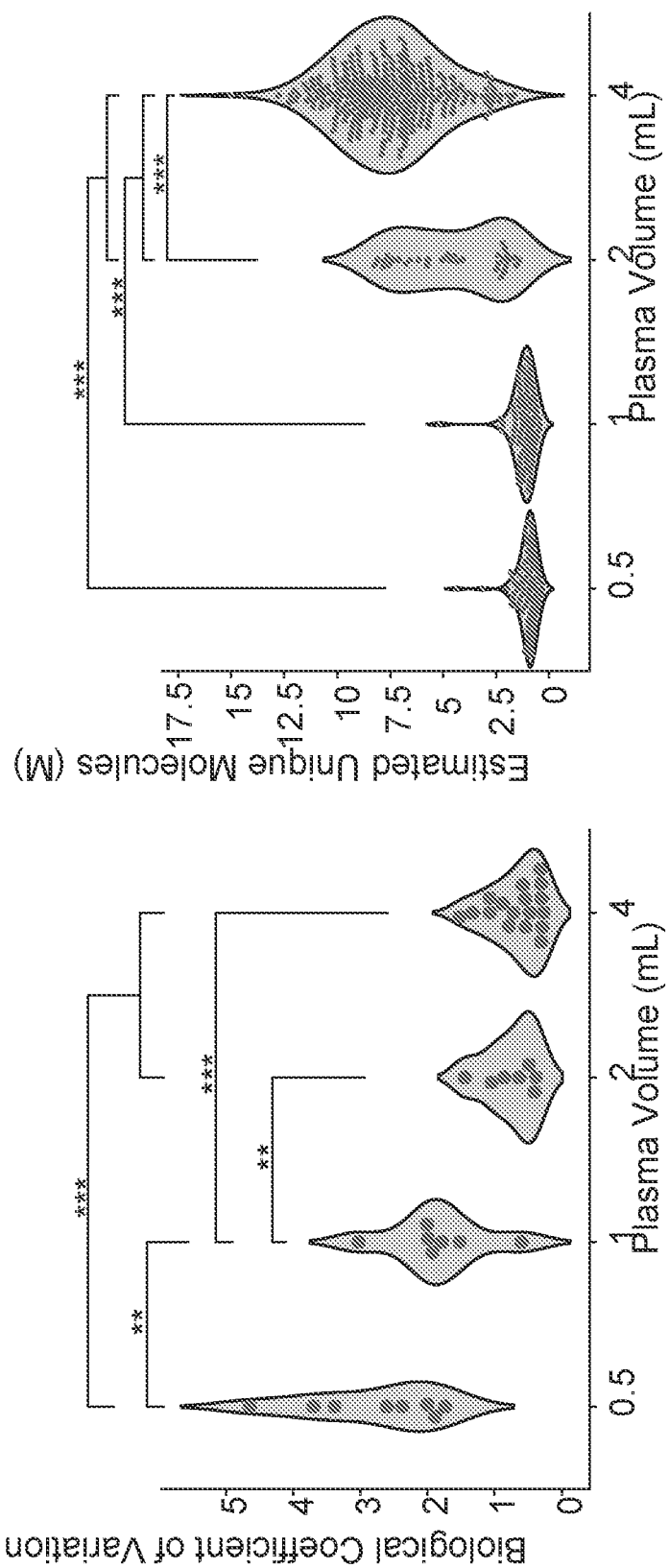
FIGS. 27A and 27B. The effect of plasma volume on C-RNA data quality. A meta-analysis was performed with data from nine independent studies to determine the appropriate plasma input for the protocol. Noise (biological coefficient of variation, EdgeR) was calculated from biological replicates within each study (FIG. 27A). Library complexity (bound population, Preseq) was calculated for each sample (FIG. 27B).  p<0.01, * p<0.001 by ANOVA with Tukey's HSD correction, with study as a blocking variable.

Shipment of blood allowed us to easily obtain an average of 5 mL plasma per patient from a single tube of blood. The difference in C-RNA data quality was assessed when using varying plasma volumes and determined that using <2 mL plasma significantly increased noise and decreased library complexity (FIGS. 27A and 27B). Thus 4 mL of plasma was used for the studies of this example to maximize confidence in data quality.

Figure 22B:
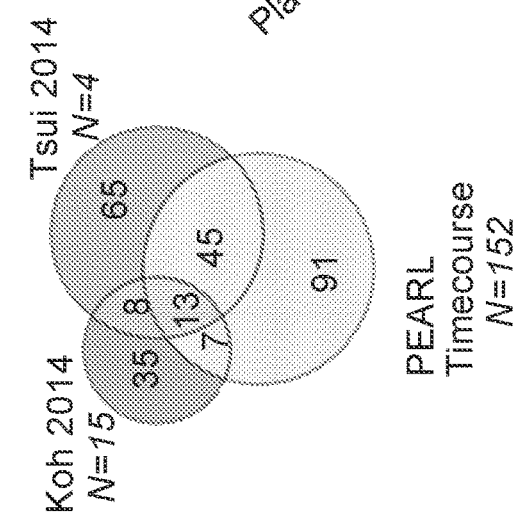
Figure 22C:
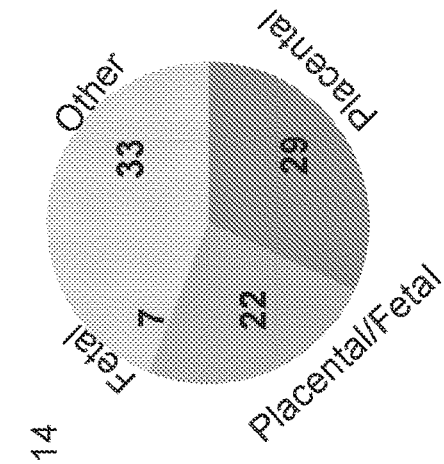
Figure 22D:
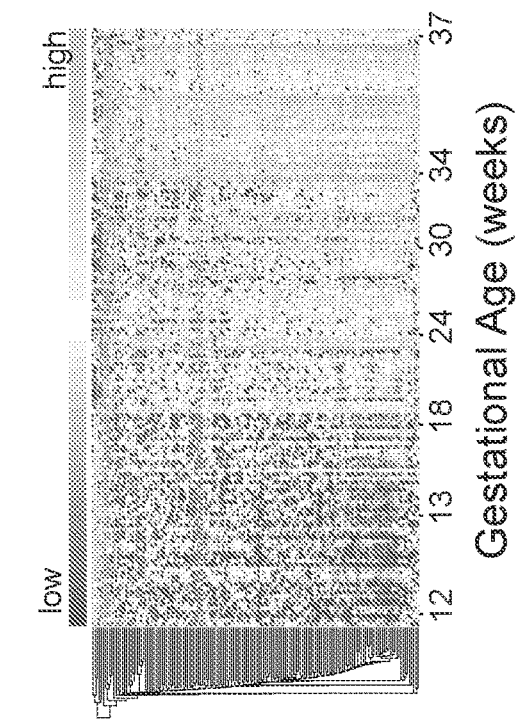

This novel workflow was validated by recapitulating previous work monitoring C-RNA dynamics of >10,000 transcripts per healthy pregnancy from first to third trimester. Using 152 samples collected serially from 45 healthy pregnancies (Pre-Eclampsia and Growth Restriction Longitudinal Study Control Cohort—PEARL; NCT02379832; Table 5), 156 significantly altered transcripts were identified, with the majority increasing in abundance as pregnancy progresses (FIG. 22B). 42% of the altered genes were identified in prior C-RNA studies (FIG. 22C) (Koh et al., 2014, *Proceedings of the National Academy of Sciences;* 111:7361-7366; and Tsui et al., 2014, *Clinical Chemistry;* 60:954-962). Of the 91 transcripts identified only in this study, 64% are expressed by placental and/or fetal tissues (FIGS. 22D and 28A-28C). Presumably, the remaining genes reflect the maternal response to pregnancy.

Study Design

For the next phase of investigation, the workflow was applied on clinical samples to measure C-RNA changes in PE (iPC, Illumina Preeclampsia Cohort). PE is a heterogeneous disorder and associated with different severity and patient outcomes based on whether it manifests before (early-onset) or after (late-onset) 34 gestational weeks (Staff et al., 2013, *Hypertension;* 61:932-942; Chaiworapongsa et al., 2014, *Nature Reviews Nephrology;* 10, 466-4803; and Dadelszen et al., 2003, *Hypertension in Pregnancy;* 22:143-148). This study to focused on the more severe early-onset form of PE and defined strict diagnostic criteria with clear inclusion and exclusion requirements—most critically excluding any individuals with a history of chronic hypertension—in order to obtain a clean cohort (Table 6) (Nakanishi et al., 2017, *Pregnancy Hypertension;* 7:39-43; and Hiltunen et al., 2017, *PLoS ONE;* 12:e0187729). Maternal characteristics, pregnancy outcomes, and medications in use were recorded throughout the study (Table 7). 113 samples were collected across 8 sites (Table 8), 40 at the time of PE diagnosis, and 73 controls gestationally-age matched within 1 week (FIG. 23A). All but one woman with PE gave birth prematurely, in contrast to 9.5% of controls, confirming these diagnostic criteria as identifying individuals severely impacted by this disease (FIG. 23C).

All samples were randomly distributed across multiple processing batches, then sequenced to ≥40 M reads. Standard differential expression analysis using the full cohort identified 42 altered transcripts, with 37 increased in PE (FIG. 24A, blue and orange). However, of concern was the high variability observed in the genes detected as altered when different subsets of controls were selected for analysis.

To address this discrepancy, a jackknifing approach was incorporated which allowed the identification of the genes that are most consistently altered (FIGS. 24A and 24B, orange). 1,000 iterations of differential analysis with randomly selected sample subsets were performed, which allowed the construction of confidence intervals for the p-values associated with each putatively altered transcript (FIG. 29A). 12 genes whose confidence interval exceeded 0.05 were excluded (FIG. 24B). These genes would not have been excluded by simply setting a threshold for baseline abundance or biological variance (FIG. 29B), however it was observed that these transcripts have lower predictive value (FIG. 29C). Hierarchical clustering indicates these genes are not altered universally in the PE cohort, and thus lack sensitivity (73%) for accurate classification of this condition (FIG. 29D).

The analysis then focused on the refined 30 gene set, 60% of which have previously been associated with PE (Namli et al., 2018, *Hypertension in Pregnancy;* 37: 9-17; Than et al., 2018, *Frontiers in Immunology;* 9:1661; Kramer et al., 2016, *Placenta;* 37:19-25; Winn et al., 2008, Endocrinology; 150: 452-462; and Liu et al., 2018, *Molecular Medicine Reports;* 18:2937-2944). qPCR analysis confirmed 19 of 20 genes as significantly altered in PE (FIG. 24C, Table 9). Strikingly, 40% of these genes encode for extracellular or secreted protein products. Additionally, nearly all genes are involved in PE relevant processes, including extracellular matrix (ECM) remodeling, pregnancy duration, placental/fetal development, angiogenesis, and hypoxia response (Table 10). 67% of these transcripts were expressed by the placenta and/or fetus (FIG. 24D). In the remaining maternally expressed transcripts, cardiovascular and immune functions were well represented (Table 10). Hierarchical clustering of these genes effectively segregated PE and control samples with 98% sensitivity and 97% specificity (FIG. 24E). Intriguingly, clinical data for the two misidentified controls indicated potentially confounding health problems, as suggested by their use of hypertensive medication (Table 7).

Using the genes identified in iPC, the ability to cluster a cohort of samples obtained from an independent biobank was assessed—the Pre-Eclampsia and Growth Restriction Longitudinal Study (PEARL; NCT02379832; FIGS. 23B and 23C, Table 11). This cohort consisted of both early- (diagnosed at <34 weeks); and late-onset PE with gestationally age-matched controls. Early-onset PE samples clustered separately from matched controls with 83% sensitivity and 92% specificity, further validating the relevance of these transcripts (FIG. 24F). In contrast, no clustering was observed for the late-onset PE and matched control samples (FIG. 24G).

The iPC data was then used to build an AdaBoost model for robust classification of PE samples. In order to create a generalized machine learning model that could accurately predict new samples, a rigorous approach was used that avoided overfitting to a single dataset and validated the final classifier with samples not used for model building (FIGS. 30A-30D and FIGS. 31A-31E). Surprisingly, the final model only utilized 7 genes, 3 of which have not been previously reported (FIG. 25A). For the entire iPC cohort, this model classified samples with extremely high accuracy (AUC=0.99, sensitivity=98%, specificity=99%; FIGS. 25B and 25C, blue). Early-onset PE PEARL samples were also accurately classified (AUC=0.88, sensitivity=100%, specificity=83%; FIGS. 25B and 25C, pink). Unexpectedly, late-onset PE PEARL samples were also classified with reasonable accuracy (AUC=0.74, sensitivity=75%, specificity=67%; FIGS. 25B and 25C, green).

This gene set was highly concordant with transcripts identified by differential abundance analysis (FIG. 25D; Table 10). The classifier relied on both placentally and maternally expressed transcripts (FIG. 25E). All genes used by the model form protein products that are either extracellular or membrane bound. Despite the small number of genes selected by AdaBoost, a diversity of PE-relevant functions was observed, specifically cardiovascular function and angiogenesis, immune regulation, fetal development, and ECM remodeling.

Methods

Prospective Clinical Sample Collection. Pregnant patients were recruited in an Illumina sponsored clinical study protocol in compliance with the International Conference on Harmonization for Good Clinical Practice. Following informed consent, 20 mL whole blood samples were collected from 40 pregnant women with a diagnosis of preeclampsia before 34 weeks gestation with severe features defined per ACOG guidelines (Table 6). Samples from 76 healthy pregnancies were also collected and were matched for gestational age to the preeclampsia group. Three control samples developed term preeclampsia after blood collection and were excluded from data analysis. For detailed inclusion and exclusion criteria, see Table 6. Patient clinical history, treatment and birth outcome information were also recorded (Table 7).

Patients were recruited across 8 different clinical sites, including University of Texas Medical Branch (Galveston, Texas), Tufts Medical Center (Boston, MA), Columbia University Irving Medical Center (New York, NY), Winthrop University Hospital (Mineola, NY), St. Peter's University Hospital (New Brunswick, NJ), Christiana Care (Newark, DE), Rutgers University Robert Wood Johnson Medical School (New Brunswick, NJ) and New York Presbyterian/Queens (New York, NY). The clinical protocol and informed consent were approved by each clinical site's Institutional Review Board. See Table 8 for patient distribution across clinical sites.

PEARL Validation Cohort Study Design. Illumina obtained plasma samples from the Preeclampsia and Growth Restriction Longitudinal study (PEARL; NCT02379832) to be used as an independent validation cohort. Plasma samples were obtained after the study had reached completion. PEARL samples were collected at the Centre hospitalier universitaire de Québec (CHU de Québec) with principal investigator Emmanual Bujold, MD, MSc. A group of 45 control pregnancies and 45 case pregnancies were recruited in this study and written informed consent was obtained for all patients. Only participants above 18 years of age were eligible, and all pregnancies were singleton.

Preeclampsia Group. The criteria for preeclampsia was defined based on the Society of Obstetricians and Gynecologists of Canada (SOGC) June 2014 criteria for preeclampsia, with a gestational age requirement between 20 and 41 weeks. A blood sample was taken once at the time of diagnosis.

Control Group. 45 pregnant women who were expected to have a normal pregnancy were recruited between 11 and 13 weeks gestational age. Each enrolled patient was followed longitudinally with blood drawn at 4 timepoints throughout pregnancy until birth. The control women were divided into three subgroups and subsequent follow up blood draws were staggered to cover the entire range of gestational ages throughout pregnancy (Table 5).

The PEARL control samples were used for two purposes. 153 longitudinal samples from 45 individual women were used to monitor placental dynamics throughout pregnancy. Additionally, control samples were selected for comparison to the preeclampsia cohort, which were matched for gestational age and used to validate the model.

Study Sample Processing. All samples from the Illumina prospective collection and the PEARL samples were processed identically by investigators blinded to disease status. Two tubes of blood were collected per patient in Cell-Free DNA BCT tubes (Streck) following the manufacturer instructions. Blood samples were stored and shipped at room temperature overnight and processed within 72 hours. Blood was centrifuged at 1,600×g for 20 minutes at room temperature, plasma transferred to a new tube and centrifuged additional 10 minutes at 16,000×g to remove residual cells. Plasma was stored at −80° C. until use. Circulating RNA was extracted from 4.5 mL of plasma using the Circulating Nucleic Acid Kit (Qiagen) followed by DNAse I digestion (Thermofisher) according to manufacturer's instructions.

cDNA Synthesis and Library Prep. Circulating RNA was fragmented at 94° C. for 8 minutes followed by random hexamer primed cDNA synthesis using the Illumina TruSight Tumor 170 Library Prep kit (Illumina). Illumina sequencing library prep was carried out according to TST170 Tumor Library Prep Kit for RNA, with the following modifications to accommodate low RNA inputs. All reactions were reduced to 25% of original volume and the ligation adaptor was used at 1 in 10 dilution. Library quality was assessed using High Sensitivity DNA Analysis kits on the Agilent Bioanalzyer 2100 (Agilent).

Whole Exome Enrichment. Sequencing libraries were quantified using Quant-iT PicoGreen dsDNA Kit (ThermoFisher Scientific), normalized to 200 ng input and pooled to 4 samples per enrichment reaction. Whole exome enrichment was carried out according to the TruSeq RNA Access Library Prep guide (Illumina). Additional blocking oligos lacking the 5' biotin designed against hemoglobin genes HBA1, HBA2, and HBB were included in the enrichment reaction to reduce enrichment of these genes in the sequencing libraries. Final enrichment libraries were quantified using Quant-IT Picogreen dsDNA Kit (ThermoFisher Scientific), normalized and pooled for paired end 50 by 50 sequencing on Illumina HiSeq 2000 platforms to a minimum depth of 40 million reads per sample.

Data Analysis. Unless otherwise noted, all statistical testing was two-sided. Non-parametric testing was used when data were not normally distributed. Sequencing reads were mapped to human reference genome (hg19) with tophat (v2.0.13), and transcript abundance quantified with featureCounts (subread-1.4.6) against RefGene coordinates (obtained Oct. 27, 2014). Tissue expression data were obtained from Body Atlas (CorrelationEngine, BaseSpace, Illumina, Inc) (Kupershmidt, et al., 2010, *PLoS ONE* 5; 10.1371/journal.pone.0013066). vGenes with expression ≥2-fold higher than the median expression across all tissues in the placenta or any of the fetal tissues (brain, liver, lung, and thyroid) were assigned to that group. Subcellular localization was obtained from UniProt.

Differential expression analysis was performed in R (v3.4.2) with edgeR (v3.20.9), after exclusion of genes with a CPM ≤0.5 in <25% of samples. The dataset was normalized by the TMM method, and differentially abundant genes identified by the glmTreat test for a log fold change ≥1 followed by Bonferroni-Holm p-value correction. The same process was used for each jackknifing iteration, using 90% of samples in each group selected by random sampling without replacement. After 1,000 jackknifing iterations, the one-sided 95% confidence interval for gene-wise p-values was calculated with statsmodels (v0.8.0). Hierarchical clustering analysis was performed with squared Euclidean distance and average linkage.

AdaBoost was performed in python with scikit-learn (v0.19.1, sklearn.ensemble. AdaBoostClassifier). Optimal hyperparameter values (90 estimators, 1.6 learning rate) were determined by grid search, using Matthew's correlation coefficient to quantify performance. The overall AdaBoost model development strategy is illustrated in FIGS. 31A-31E. Datasets (TMM-normalized log CPM values of genes with a CPM ≤0.5 in <25% of samples) were standardized (sklearn.preprocessing. StandardScaler) prior to fitting classifiers. The same scaler fit on training data was applied to the corresponding testing dataset; all 5 scalers for the 5 training datasets were averaged for use with the final model. The decision function score was used to construct ROC curves and determine sample classification.

RT-qPCR validation assay and analysis. C-RNA was isolated and converted to cDNA from 2 mls of plasma from 19 Preeclampsia (PE) and 19 matched control samples, which were selected randomly. The cDNA was pre-amplified using the TaqMan Preamp master Mix (cat: 4488593) for 16 cycles and diluted 10-fold to a final volume of 500 µL. For qPCR, the reaction mixture contained 5 µL of diluted pre-amplified cDNA, 104, of TaqMan gene expression master mix (cat: 4369542), 1 µL of TaqMan Probe, and 44, of water using the manufacturer's instructions. For each TaqMan probe (Table 9), three qPCR reactions were carried out per diluted cDNA sample and the Cq values were determined using Bio-Rad CFX manager software. To determine gene abundance for each target gene, the $\Delta\Delta Cq = 2^{\wedge}-$ (target Cq−ref $Cq_{avg}$) was calculated using the mean Cq values between five reference gene probes (ref $Cq_{avg}$). To determine the fold change (PE/CTRL) for each probe, the ΔΔCq values for each sample was divided by the average ΔΔCq value for the matched control group.

Tube type study. To assess the effects of tube type and overnight shipping on circulating RNA quality, blood was drawn from pregnant and non-pregnant females in the following tube types: K2 EDTA (Beckton Dickinson), ACD (Beckton Dickinson), Cell Free RNA BCT tube (Streck), and 1 Cell Free DNA BCT tube (Streck). 8 mL of blood was drawn into each tube and shipped overnight either on ice packs (EDTA and ACD) or shipped at room temperature (Cell Free RNA and DNA BCT tubes). All shipped blood tubes were processed into plasma within 24 hours of the blood draw. As a reference, 8 mL of blood was also drawn into K2 EDTA tubes and processed within 4 hours into plasma on site and shipped as plasma on dry ice. All plasma processing and circulating RNA extraction was carried out as described in the methods section. 3 mL of plasma was used per condition to generate sequencing libraries for enrichment using Illumina protocols as described.

Reproducibility Study. Plasma was obtained from 10 individuals and split into 4 mL, 1 mL, and 0.5 mL volumes, with 3 replicates for each volume. Circulating RNA extraction (Qiagen Circulating Nucleic Acid Kit) and random primed cDNA synthesis were carried out on all samples as previously described. For libraries using 4.5 mL plasma inputs, sequencing libraries were generated using the TST170 Tumor Library Prep Kit as described above. For 1 mL and 0.5 mL inputs, the Accel-NGS 1S Plus DNA Library Kit (Swift Biosciences) was used to generate libraries. Whole exome enrichment and sequencing was carried out on all samples using as described above.

Discussion

This study focused on identifying differences that are universal to early-onset PE, supporting the ultimate goal of clinically actionable biomarker discovery. This required tailoring the analysis methods to account for the variability observed in the data. This variance stems from both the substantial biological noise in C-RNA measurements as well as the phenotypic diversity of PE. C-RNA is inherently more variable than single tissue transcriptomics because it represents a combination of cell death, signaling, and gene expression across all organs. Furthermore, PE exhibits a wide range of maternal and fetal outcomes which may be associated with different underlying molecular causes. While the genes that were eliminated may be biologically relevant in PE, they were not universal in the cohort. Interestingly, the excluded transcripts were elevated in specific women, who may represent a molecular subset of PE. Larger cohorts will help elucidate if C-RNA can delineate PE subtypes, which is crucial to understanding the diverse pathophysiology of this condition.

The most universal set of transcripts was identified by AdaBoost. The success of this method was underscored by highly accurate classification of an independent early-onset PE cohort (PEARL). These samples were collected from a different population with significantly relaxed inclusion and exclusion criteria, for instance including women in the control group who had chronic hypertension, gestational diabetes, or Alport syndrome—none of which were misidentified as having PE. In contrast to hierarchical clustering, 17 of 24 individuals from the late-onset PE cohort were correctly classified by machine learning model of this example, surprising given the suggestion that early- and late-onset PE are distinct conditions. The findings of this example suggest there may be some pathways universally altered in all PE.

In every assessment, C-RNA revealed changes in placental, fetal, and maternally expressed transcripts. One of the most striking trends observed in PE samples was the increased abundance of myriad ECM remodeling and cell migration/invasion proteins (FAM107A, SLC9A3R2, TIMP4, ADAMTS1, PRG2, TIMP3, LEP, ADAMTS2, ZEB1, HSPA12B), tracking with dysfunctional extravillous trophoblast invasion and remodeling of maternal vessels characteristic in this disease. The maternal side of early-onset PE manifests as cardiovascular dysfunction, inflammation, and preterm birth (PNMT, ZEB1, CRH), all of which show molecular signs of aberrant behavior in the data of this example.

TABLE 5

PEARL Control Cohort Gestational Age Distribution for 45 healthy pregnancies

| Control Groups | Recruitment | Follow up visit #1 | Follow up visit #2 | Follow up visit #3 |
| --- | --- | --- | --- | --- |
| Group 1 (n = 15) | $11^{0/7}$-$13^{6/7}$ weeks | $14^{0/7}$-$17^{6/7}$ weeks | $26^{0/7}$-$28^{6/7}$ weeks | $35^{0/7}$-$37^{6/7}$ weeks |
| Group 2 (n = 15) | $11^{0/7}$-$13^{6/7}$ weeks | $18^{0/7}$-$21^{6/7}$ weeks | $29^{0/7}$-$31^{6/7}$ weeks | $35^{0/7}$-$37^{6/7}$ weeks |
| Group 3 (n = 15) | $11^{0/7}$-$13^{6/7}$ weeks | $22^{0/7}$-$25^{6/7}$ weeks | $32^{0/7}$-$34^{6/7}$ weeks | $35^{0/7}$-$37^{6/7}$ weeks |

TABLE 6

Diagnostic Criteria for Preeclampsia with Severe Features and Inclusion/Exclusion Criteria

| | |
| --- | --- |
| Blood Pressure | 1) Systolic BP ≥160 mmHG or diastolic BP ≥110 mmHg measured on at least 2 occasions 4 hours apart while on bedrest but before the onset of labor or measured on 1 occasion only, if antihypertensive therapy is initiated due to severe hypertension |
| | Measured by one of the following: |
| Proteinuria | 1) Excretion of ≥300 mg of protein in a 24 hr period |
| | 2) Protein/creatinine value of at least 0.3 |
| | 3) qualitative determination with urine dipstick of ≥1+ |
| | OR |

TABLE 6-continued

Diagnostic Criteria for Preeclampsia with Severe Features and Inclusion/Exclusion Criteria

| | |
|---|---|
| Blood Pressure | 1) Systolic BP ≥140 mmHg or diastolic ≥90 mmHG |
| With one of the following features | 1) Thombocytopenia (<100,000 platelets/mL) |
| | 2) Impaired liver function |
| | 3) Newly developed renal insufficiency |
| | 4) Pulmonary edema |
| | 5) New onset cerebral disturbances or scotomata |

Preeclampsia Cohort

| Inclusion Criteria | Exclusion Criteria |
|---|---|
| 1. Women 18 years of age or older | 1. Known Malignancy |
| 2. Pregnant women with a viable singleton gestation | 2. History of maternal organ or bone marrow transplant |
| 3. Gestational age between 20 0/7 and 33 6/7 weeks determined by ultrasound and/or LMP per ACOG guidelines. | 3. Maternal blood transfusion in the last 8 weeks |
| 4. Preeclampsia diagnosed with severe features per ACOG guidelines | 4. Chronic Hypertension diagnosed prior to current pregnancy |
| | 5. Type I, II or gestational diabetes |
| | 6. Fetal anomaly or known chromosome abnonnality |
| | 7. Active Labor |

Control Cohort

| Inclusion Criteria | Exclusion Criteria |
|---|---|
| 1. Women 18 years of age or older | 1. Known Malignancy |
| 2. Pregnant women with a viable singleton gestation | 2. History of maternal organ or bone marrow transplant |
| 3. Gestational age between 20 0/7 and 33 6/7 weeks determined by ultrasound and/or LMP per ACOG guidelines. | 3. Maternal blood transfusion in the last 8 weeks |
| | 4. Chronic Hypertension diagnosed prior to current pregnancy |
| | 5. Type I, II or gestational diabetes |
| | 6. Fetal anomaly or known chromosome abnormality |
| | 7. Active Labor |
| | 8. Thrombocytopenia (<100,000 plts/mL) |
| | 9. Impaired liver function |
| | 10. Newly developed renal insufficiency (serum creatine >1.1 mg/dL) |
| | 11. Pulmonary edema |
| | 12. New Onset cerebral disturbances or scotomata |
| | 13. Preeclampsia in prior or current pregnancy |
| | 14. Fetal growth restriction |

TABLE 7

Study characteristics for Illumina Preeclampsia Cohort

| | | Early Onset PE Cohort | Control Cohort |
|---|---|---|---|
| Sample Size | | n = 40 | n = 73 |
| Gestational Age at Sample Collection (weeks · days) | | 30.5 (+/−2.6) | 30.5 (+/−2.6) |
| Maternal Characteristics | | | |
| Ethnicity | (% Hispanic) | 35% (n = 14) | 41.1% (n = 30) |
| Race | % Caucasian | 35% (n = 14) | 46.6% (n = 34) |
| | % African American | 27.5% (n = 11) | 17.8% (n = 13) |
| | % Asian | 7.5% (n = 3) | 13.7% (n = 10) |
| | % Unknown | 30% (n = 12) | 20.5% (n = 15) |
| | % Other | 0.0% | 1.4% (n = 1) |
| Maternal Age (years, mean +/− SD) | | 30.4 (+/−5.7) | 29.7 (+/−5.3) |
| Maternal BMI (kg/m2, mean +/− SD) | | 34.2 (+/−5.8) | 30.1 (+/−5.6) |
| Gravida (% Nulliparous) | | 32.5% (n = 13) | 38.4% (n = 28) |
| Chronic Hypertension | | 0% (n = 0) | 0% (n = 0) |
| Type I, II Diabetes | | 0% (n = 0) | 0% (n = 0) |
| Gestational Diabetes | | 0% (n = 0) | 0% (n = 0) |

TABLE 7-continued

Study characteristics for Illumina Preeclampsia Cohort

|  |  | Early Onset PE Cohort | Control Cohort |
|---|---|---|---|
| Birth Outcomes | | | |
| Gestational Age at Birth (weeks · days) | | 31.5 (+/−3.1) | 38.9 (+/−1.8) |
| Full Term | | 2.5% (n = 1) | 90.4% (n = 66) |
| Preterm (<37 weeks) | | 97.5% (n = 39) | 9.6% (n = 7) |
| Sex (% male) | | 37.5% (n = 15) | 42.5% (n = 31) |
| Birth Weight (kg) | | 1.4 (+/−0.52) | 3.2 (+/−0.55) |
| Small for Gestational Age* | | 45% (n = 18) | 9.6% (n = 7) |
| Stillbirth | | 2.5% (n = 1) | 0% (n = 0) |
| Medications for treatment of: | | | |
| PE/Hypertension | MgSO4 | 82.5% (n = 33) | 4.1% (n = 3) |
|  | Antenatal Steroids | 95.0% (n = 38) | 6.8% (n = 5) |
|  | Anti-Hypertensive | 75.0% (n = 30) | 5.3% (n = 4) |
|  | Aspirin | 20.0% (n = 8) | 0% (n = 0) |
| Other Conditions | Analgesics | 60.0% (n = 24) | 11.8% (n = 9) |
|  | Antimicrobials | 12.5% (n = 5) | 5.5% (n = 4) |
|  | Antihistamines | 32.5% (n = 13) | 13.7% (n = 10) |
|  | Asthma | 10.0% (n = 4) | 2.7% (n = 2) |
|  | Psychoactive | 15.0% (n = 6) | 5.5% (n = 4) |
|  | Hypothyroidism | 7.5% (n = 3) | 2.7% (n = 2) |
|  | Antiemetics | 25.0% (n = 10) | 5.5% (n = 4) |
| Pregnancy Symptoms | Antacids | 27.5% (n = 11) | 8.2% (n = 6) |
|  | Anti-constipation | 15.0% (n = 6) | 11.8% (n = 9) |
|  | Prenatal Vitamins | 17.5% (n = 7) | 31.5% (n = 23) |
|  | Iron Supplement | 10% (n = 4) | 12.3% (n = 9) |

*Defined as birthweight <10% of population for male or female fetus

TABLE 8

Medical Center Collection Site Patient Distribution

| Clinical Site | Location | Number PE patients | Number of controls |
|---|---|---|---|
| University of Texas Medical Branch | Galveston, Texas | 4 | 11 |
| Tufts Medical Center | Boston, MA | 10 | 17 |
| Columbia University Irving Medical Center | New York, NY | 4 | 9 |
| Winthrop University Hospital | Mineola, NY | 5 | 9 |
| St. Peter's University Hospital | New Brunswick, NJ | 3 | 6 |
| Christiana Care | Newark, DE | 7 | 13 |
| Rutgers University Robert Wood Johnson Medical School | New Brunswick, NJ | 5 | 8 |
| New York Presbyterian/Queens | New York, NY | 2 | 3 |
| Total Samples collected | | 40 | 76 |

TABLE 9

Genes validated by TaqMan qPCR

| Gene Name | Assay ID | Type | RefSeq |
|---|---|---|---|
| ABHD12 | Hs01018050_m1 | Reference | NM_001042472.2 |
| ABHD12 | Hs01018050_m1 | Target | NM_001042472.2 |
| ADAMTS2 | Hs01029111_m1 | Target | NM_014244.4 |
| ALOX15B | Hs00153988_m1 | Target | NM_001039130.1 |
| ARHGEF25 | Hs00384780_g1 | Target | NM_001111270.2 |
| ARRDC2 | Hs01006434_g1 | Target | NM_001286826.1 |
| CLEC4C | Hs01092460_m1 | Target | NM_130441.2 |
| DAAM2 | Hs00322497_m1 | Target | NM_001201427.1 |
| FAM107A | Hs00200376_m1 | Target | NM_001076778.2 |
| HSPA12B | Hs00369554_m1 | Target | NM_001197327.1 |
| HTRA4 | Hs00538137_m1 | Target | NM_153692.3 |
| IGFBP5 | Hs00181213_m1 | Target | NM_000599.3 |
| KRBOX4 | Hs01063506_gH | Reference | NM_001129898.1 |
| KRT5 | Hs00361185_m1 | Target | NM_000424.3 |
| LEP | Hs00174877_m1 | Target | NM_000230.2 |
| NES | Hs00707120_s1 | Target | NM_006617.1 |
| NME3 | Hs01573872_g1 | Reference | NM_002513.2 |
| PAPPA2 | Hs01060983_m1 | Target | NM_020318.2 |
| PITPNM3 | Hs01107787_m1 | Target | NM_001165966.1 |
| PLD4 | Hs00975488_m1 | Target | NM_001308174.1 |
| PRG2 | Hs00794928_m1 | Target | NM_001243245.2 |
| TIMP3 | Hs00165949_m1 | Target | NM_000362.4 |
| TIMP4 | Hs00162784_m1 | Target | NM_003256.3 |
| VSIG4 | Hs00907325_m1 | Target | NM_001184830.1 |
| WNT7A | Hs00171699_m1 | Reference | NM_004625.3 |
| ZEB1 | Hs01566408_m1 | Target | NM_001128128.2 |
| ZNF138 | Hs00864088_gH | Reference | NM_001271638.1 |

TABLE 10

| Gene Symbol | Analysis | Previous Literature Reports | Change in PE | Tissue Expression Category | Sub-Cellular Location | Function(s) |
|---|---|---|---|---|---|---|
| ARRDC2 | AdaBoost | No | Increase* | Other (Skeletal Muscle; Globus Pallidus; Lung) | Membrane | Protein Trafficking |
| ALOX15B | DEX | Yes | Increase | Fetal | Nucleus; Cytoskeleton; Cytosol; Membrane | Cell Cycle; Immune Function; Cardiovascular Function |
| AMPH | DEX | No | Increase | Fetal | Cytoskeleton; Membrane | Synaptic Vesicle Endocytosis |
| CUX2 | DEX | No | Decrease | Fetal | Nucleus | Cell Cycle; Fetal Development; DNA Damage Response |
| FAM107A | DEX | No | Increase | Fetal | Cytoskeleton; Membrane; Nucleus | Cell Migration/Invasion; Cell Cycle; ECM Regulation |
| IGFBP5 | DEX | Yes | Increase | Fetal | Extracellular or Secreted | Fetal Development; IGF Signaling |
| NES | DEX | Yes | Increase | Fetal | Cytoskeleton | Fetal Development; Cell Cycle |
| PITPNM3 | DEX | No | Increase | Fetal | Membrane | Phosphatidylinositol Regulation |
| PRX | DEX | Yes | Increase | Fetal | Membrane | Cell Structure/Composition |
| TEAD4 | DEX | Yes | Increase | Fetal | Nucleus | Placental Development |
| PNMT | DEX | Yes | Increase | Other (Adrenal Gland Cortex; Adrenal Gland; Skeletal Muscle Psoas) | Cytosol | Epinephrine Synthesis; Cardiovascular Function; Pregnancy Duration |
| DAAM2 | DEX | Yes | Increase | Other (Corpus Callosum; Globus Pallidum External; Nodose Nucleus) | Extracellular or Secreted | Fetal Development |
| SLC9A3R2 | DEX | No | Increase | Other (Heart Ventricle; Liver; Parotid Gland) | Membrane; Nucleus | ECM Regulation; Cell Structure/Composition |
| HSPA12B | DEX | No | Increase | Other (Heart Ventricle; Lung; Spleen) | unknown | Angiogenesis; Cardiovascular Function; Cell Migration/Invasion; Hypoxia Response |
| PLD4 | DEX | No | Decrease | Other (Nodose Nucleus; Subthalamic Nucleus; Corpus Callosum) | Membrane | Phosphatidylinositol Regulation; Immune Function |
| TIMP4 | DEX | No | Increase | Other (Omental Adipose Tissue; Subcutaneous Adipose Tissue; Joint Synovium) | Extracellular or Secreted | ECM Regulation; Immune Function |
| KRT5 | DEX | Yes | Decrease | Other (Oral Mucosa; Pharyngeal Mucosa; Esophagus) | Cytoskeleton | Cell Structure/Composition |
| ZEB1 | DEX | No | Increase | Other (Synovial Membrane; Aorta; Myometrium) | Nucleus | Immune Function; Cell Migration/Invasion; Fetal Development; Pregnancy Duration |
| APOLD1 | DEX | Yes | Increase | Placental | Plasma Membrane | Angiogenesis; Cardiovascular Function; Hypoxia Response; Fetal Development |
| HTRA4 | DEX | Yes | Increase | Placental | Extracellular or Secreted | IGF Signaling; Placental Development |
| SEMA3G | DEX | No | Increase | Placental | Extracellular or Secreted | Cell Migration/Invasion |
| ADAMTS1 | DEX | Yes | Increase | Placental/Fetal | Extracellular or Secreted | ECM Regulation; Fetal Development; Angiogenesis |
| CRH | DEX | Yes | Increase | Placental/Fetal | Extracellular or Secreted | Pregnancy Duration; Fetal Development; Cardiovascular Function |
| PRG2 | DEX | Yes | Increase | Placental/Fetal | Extracellular or Secreted | Immune Function; ECM Regulation; IGF Signaling |
| TIMP3 | DEX | Yes | Increase | Placental/Fetal | Extracellular or Secreted | ECM Regulation; Immune Function; Angiogenesis |
| ARHGEF25 | DEX & AdaBoost | No | Increase | Other (Hippocampus; Myometrium; Cerebellum) | Membrane; Sarcomere | |
| CLEC4C | DEX & AdaBoost | Yes | Decrease | Other (Rectum Colon; Ascending Colon; Substantia Nigra Reticulata) | Membrane | Immune Function |
| LEP | DEX & AdaBoost | Yes | Increase | Placental | Extracellular or Secreted | Energy Homeostasis; Immune Function; Angiogenesis; Fetal Development; ECM Regulation |

TABLE 10-continued

| Gene Symbol | Analysis | Previous Literature Reports | Change in PE | Tissue Expression Category | Sub-Cellular Location | Function(s) |
|---|---|---|---|---|---|---|
| PAPPA2 | DEX & AdaBoost | Yes | Increase | Placental | Extracellular or Secreted | Fetal Development; IGF Signaling |
| VSIG4 | DEX & AdaBoost | Yes | Increase | Placental | Membrane | Immune Function |
| ADAMTS2 | DEX & AdaBoost | No | Increase | Placental/Fetal | Extracellular or Secreted | ECM Regulation; Angiogenesis; Fetal Development |

Key
Increase* indicates the change was not statistically different
CorrelationEngine Body Atlas was used to find the 3 top tissues expressing genes in the "Other" category
UniProt was used to determine sub-cellular localization . . . as a note; I merged all "membrane" classifications to one category (so Plasma Membrane; ER Membrane; etc are not distinct)

TABLE 11

Study characteristics for Illumina Preeclampsia Cohort

| | | Early Onset PE | Early Onset Control | Late Onset PE | Late Onset Control |
|---|---|---|---|---|---|
| Sample Size | | n = 12 | n = 12 | n = 12 | n = 12 |
| Gestational Age at Sample Collection (weeks · days) | | 29.2 (+/−2.3) | 29.3 (+/−2.3) | 35.6 (+/−1.3) | 35.9 (+/−0.8) |
| Maternal Characteristics | | | | | |
| Ethnicity | (% Hispanic) | 0% (n = 0) | 0% (n = 0) | 0% (n = 0) | 0% (n = 0) |
| Race | % Caucasian | 91.7% (n = 11) | 100% (n = 12) | 100% (n = 12) | 100% (n = 12) |
| | % African | 8.3% (n = 1) | 0% (n = 0) | 0% (n = 0) | 0% (n = 0) |
| Maternal Age (years, mean +/− SD) | | 29.3 (+/−3.5) | 30.1 (+/−3.8) | 30.2 (+/−4.8) | 29.4 (+/−3.2) |
| Maternal BMI (kg/m2, mean +/− SD) | | 33.6 (+/−9.0) | 28.5 (+/−7.0) | 32.2 (+/−4.9) | 27.9 (+/−4.5) |
| Gravida (% Nulliparous) | | 60% (n = 6) | 58.3% (n = 7) | 75% (n = 9) | 75% (n = 9) |
| Chronic Hypertension | | 13.3% (n = 2) | 8.3% (n = 1) | 8.3% (n = 1) | 0% (n = 0) |
| Type I, II Diabetes | | 13.3% (n = 2) | 0% (n = 0) | 25.0% (n = 3) | 0% (n = 0) |
| Gestational Diabetes | | 13.3% (n = 2) | 33.3% (n = 4) | 8.3% (n = 1) | 16.7% (n = 2) |
| Other Health Condition | | 0% (n = 0) | 8.3% (n = 1) | 0% (n = 0) | 0% (n = 0) |
| Birth Outcomes | | | | | |
| Gestational Age at Birth (weeks · days) | | 30.3 (+/−3.4) | 39.0 (+/−1.5) | 37.0 (+/−1.4) | 39.7 (+/−1.6) |
| Full Term | | 0% (n = 0) | 91.7% (n = 11) | 75.0% (n = 9) | 91.7% (n = 11) |
| Preterm (<37 weeks) | | 100% (n = 12) | 8.3% (n = 1) | 25.0% (n = 3) | 8.3% (n = 1) |
| Sex (% male) | | 75% (n = 9) | 58.3% (n = 7) | 66.7% (n = 8) | 58.3% (n = 7) |
| Birth Weight (kg) | | 1.3 (+/−0.54) | 3.2 (+/−0.40) | 2.7 (+/−0.55) | 3.4 (+/−0.54) |
| Fetal Growth Restriction | | 50.0% (n = 6) | 0% (n = 0) | 8.3% (n = 1) | 0% (n = 0) |
| Small for Gestational Age* | | 25% (n = 3) | 0% (n = 0) | 33.3% (n = 4) | 25% (n = 3) |
| Stillbirth | | 0% (n = 0) | 0% (n = 0) | 0% (n = 0) | 0% (n = 0) |
| HELLP | | 25.0% (n = 3) | 0% (n = 0) | 0% (n = 0) | 0% (n = 0) |
| Medications for treatment of: | | | | | |
| PE/Hypertension | MgSO4 | 83.3% (n = 10) | 0% (n = 0) | 33.3% (n = 4) | 0% (n = 0) |
| | Antenatal Steroids | 100% (n = 12) | 0% (n = 0) | 25.0% (n = 3) | 0% (n = 0) |
| | Anti-Hypertensive | 100% (n = 12) | 8.3% (n = 1) | 75% (n = 9) | 0% (n = 0) |
| | Aspirin | 8.3% (n = 1) | 25.0% (n = 3) | 25.0% (n = 3) | 8.3% (n = 1) |

*Defined as birthweight <10% of population for male or female fetus

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of detecting and treating preeclampsia in a pregnant female, the method comprising:
   obtaining a biosample from the pregnant female;
   wherein the biosample comprises blood, plasma, or serum;
   removing intact cells from the biosample;
   treating the biosample with a deoxyribonuclease (DNase) to remove cell free DNA (cfDNA);
   synthesizing complementary DNA (cDNA) sequences from RNA molecules in the biosample;
   enriching the cDNA sequences for cDNA sequences that encode proteins;
   sequencing the resulting enriched cDNA sequences;
   identifying protein coding sequences encoded by the enriched cDNA sequences; and
   wherein identifying protein coding sequences of a protein selected from the group consisting of C-type lectin domain family 4 member C (CLEC4C), Rho guanine nucleotide exchange factor 25 (ARHGEF25), α disintegrin and metallopeptidase with thrombospondin type 1 motif 2 (ADAMTS2), arrestin domain containing 2 (ARRDC2), ski like proto-oncogene (SKIL), arrestin domain containing 4 (ARRDC4) and combinations thereof indicates the presence of preeclampsia in the pregnant female; and
   providing the pregnant female with a therapeutic intervention for the treatment of preeclampsia selected from the group consisting of antihypertensive medication, corticosteroid medication, anticonvulsant medication, preterm delivery by cesarean delivery or induced labor, and combinations thereof and/or treating the pregnant female with a low dose of aspirin, wherein a low dose of aspirin comprises about 50 to about 150 milligrams (mg) per day.

2. The method of claim 1, wherein the sequencing comprises clonal amplification and massively parallel sequencing of clonally amplified molecules.

3. The method of claim 1, wherein the biosample comprises plasma.

4. The method of claim 1, wherein the biosample is obtained from a pregnant female at less than 20 weeks gestation.

5. The method of claim 1, wherein the biosample is obtained from a pregnant female at greater than 20 weeks gestation.

6. A method of detecting and treating preeclampsia in a pregnant female, the method comprising:
   obtaining a biosample from the pregnant female;
   wherein the biosample comprises blood, plasma, or serum;
   removing intact cells from the biosample;
   treating the biosample with a deoxyribonuclease (DNase) to remove cell free DNA (cfDNA);
   synthesizing complementary DNA (cDNA) sequences from RNA molecules in the biosample;
   enriching the cDNA sequences for cDNA sequences that encode proteins;
   sequencing the resulting enriched cDNA sequences;
   identifying protein coding sequences encoded by the enriched cDNA sequences;
   wherein identifying protein coding sequences of each of:
   α disintegrin and metallopeptidase with thrombospondin type 1 motif 2 (ADAMTS2), Rho guanine nucleotide exchange factor 25 (ARHGEF25), arrestin domain containing 2 (ARRDC2), C-type lectin domain family 4 member C (CLEC4C), leptin (LEP), pappalysin 2 (PAPPA2), and V-set and immunoglobulin domain containing 4 (VSIG4); or
   ADAMTS2, ARHGEF25, ARRDC2, CLEC4C, LEP, PAPPA2, ski like protooncogene (SKIL), and VSIG4; or
   ADAMTS2, ARHGEF25, arrestin domain containing 4 (ARRDC4), CLEC4C, LEP, nestin (NES), SKIL, and VSIG4; or
   ADAMTS2, ARHGEF25, ARRDC2, ARRDC4, CLEC4C, corticotropin releasing hormone (CRH), LEP, PAPPA2, SKIL, and VSIG4; or
   ADAMTS2, ARHGEF25, ARRDC2, CLEC4C, LEP, and SKIL; or
   ADAMTS2, ARHGEF25, ARRDC2, ARRDC4, CLEC4C, LEP, PAPPA2, and SKIL indicates the presence of preeclampsia in the pregnant female; and
   providing the pregnant female with a therapeutic intervention for the treatment of preeclampsia selected from the group consisting of antihypertensive medication, corticosteroid medication, anticonvulsant medication, preterm delivery by cesarean delivery or induced labor, and combinations thereof and/or treating the pregnant female with a low dose of aspirin, wherein a low dose of aspirin comprises about 50 to about 150 mg per day.

7. The method of claim 1, wherein the biosample is a blood sample and further comprising:
   processing the blood sample into plasma without exposure to ethylenediaminetetraacetic acid (EDTA);
   processing the blood sample into plasma within about 24 to about 72 hours;
   storing and shipping the blood sample at room temperature prior to processing into plasma.

8. The method of claim 6, wherein the sequencing comprises clonal amplification and massively parallel sequencing of clonally amplified molecules.

9. The method of claim 6, wherein the biosample comprises plasma.

10. The method of claim 6, wherein the biosample is obtained from a pregnant female at less than 20 weeks gestation.

11. The method of claim 6, wherein the biosample is a blood sample and further comprising:
    processing the blood sample into plasma without exposure to ethylenediaminetetraacetic acid (EDTA);
    processing the blood sample into plasma within about 24 to about 72 hours;
    storing and shipping the blood sample at room temperature prior to processing into plasma.

12. The method of claim 6, wherein the biosample is obtained from a pregnant female at greater than 20 weeks gestation.

* * * * *